(12) United States Patent
Myette

(10) Patent No.: US 8,198,050 B2
(45) Date of Patent: *Jun. 12, 2012

(54) HEPARAN SULFATE GLYCOSAMINOGLYCAN LYASE AND USES THEREOF

(75) Inventor: James Myette, Waltham, MA (US)

(73) Assignee: Momenta Pharmaceuticals, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/974,786

(22) Filed: Dec. 21, 2010

(65) Prior Publication Data

US 2011/0104814 A1 May 5, 2011

Related U.S. Application Data

(60) Division of application No. 12/436,751, filed on May 6, 2009, now Pat. No. 7,888,072, which is a division of application No. 11/948,561, filed on Nov. 30, 2007, now Pat. No. 7,691,613, which is a division of application No. 11/592,622, filed on Nov. 3, 2006, now Pat. No. 7,691,612, which is a continuation-in-part of application No. 11/265,908, filed on Nov. 3, 2005, now Pat. No. 7,767,420.

(51) Int. Cl.
*C12P 19/28* (2006.01)
*C12N 9/00* (2006.01)
*C12N 9/88* (2006.01)
*C12N 1/20* (2006.01)
*C12N 15/00* (2006.01)
*C07H 21/04* (2006.01)

(52) U.S. Cl. ....... 435/85; 435/183; 435/232; 435/252.3; 435/320.1

(58) Field of Classification Search .................. None
See application file for complete search history.

(56) References Cited

U.S. PATENT DOCUMENTS

| | | | |
|---|---|---|---|
| 5,145,778 A | 9/1992 | Bellamy et al. | |
| 5,455,162 A | 10/1995 | Bellamy et al. | |
| 5,714,376 A | 2/1998 | Sasisekharan et al. | |
| 5,830,726 A | 11/1998 | Sasisekharan et al. | |
| 5,997,863 A | 12/1999 | Zimmermann et al. | |
| 6,217,863 B1 | 4/2001 | Godavarti et al. | |
| 6,841,375 B2 | 1/2005 | Su et al. | |
| 6,869,789 B2 | 3/2005 | Liu et al. | |
| 7,056,504 B1 | 6/2006 | Sasisekharan et al. | |
| 7,767,420 B2 * | 8/2010 | Myette | 435/85 |
| 2001/0006635 A1 | 7/2001 | Bennett et al. | |
| 2001/0034043 A1 | 10/2001 | Su et al. | |
| 2004/0018187 A1 | 1/2004 | Denholm et al. | |
| 2005/0153398 A1 | 7/2005 | Su et al. | |
| 2005/0191288 A1 | 9/2005 | Bennett et al. | |
| 2005/0233402 A1 | 10/2005 | Liu et al. | |
| 2006/0067928 A1 | 3/2006 | Liu et al. | |
| 2006/0105430 A1 | 5/2006 | Sasisekharan et al. | |
| 2006/0140928 A1 | 6/2006 | Bennett et al. | |
| 2006/0182734 A1 | 8/2006 | Liu et al. | |
| 2006/0183713 A1 | 8/2006 | Liu et al. | |
| 2007/0134226 A1 | 6/2007 | Myette | |

FOREIGN PATENT DOCUMENTS

| | | |
|---|---|---|
| CN | 1429913 A | 7/2003 |
| CN | 1699424 A | 11/2005 |
| CN | 1712418 A | 12/2005 |
| CN | 1757739 A | 4/2006 |
| DE | 10207708 A1 | 9/2003 |
| EP | 0370958 A2 | 5/1990 |
| EP | 0610408 A1 | 8/1994 |
| EP | 0769961 A1 | 5/1997 |
| EP | 0852491 A1 | 7/1998 |
| EP | 1552846 A2 | 7/2005 |
| KR | 100206182 B1 | 7/1999 |
| KR | 100257168 B1 | 5/2000 |
| KR | 20010055115 | 7/2001 |
| KR | 20020046293 | 6/2002 |
| WO | 9308289 A1 | 4/1993 |
| WO | 9716556 A1 | 5/1997 |
| WO | 0012726 A2 | 3/2000 |
| WO | 0153474 A2 | 7/2001 |
| WO | 0166772 A2 | 9/2001 |
| WO | 2007056218 A2 | 5/2007 |

OTHER PUBLICATIONS

Ahn et al., "Characterization of a bacteroides species from human intestine that degrades glycosaminoglycans", Canadian Journal of Microbiology, 1998, vol. 44, No. 5, pp. 423-429.
Blain et al., "Expression system for high levels of GAG lyase gene expression and study of the hepA upstream region in *Flavobacterium heparinum*", J. Bacteriology, 2002, vol. 184, No. 12, pp. 3242-3252.
Chica et al., "Semi-rational approaches to engineering enzyme activity: combining the benefits of directed evolution and rational design", Curr. Opinion in Biotechnology, Aug. 2005, vol. 16, pp. 378-384.
Extended European Search Report from corresponding European Application No. 506836937.0 dated Aug. 20, 2009.
Gen Bank accession No. AAO79762, (Priority Date:: Mar. 28, 2003); 2 pages.
GenBank accession No. AAO79780, (Priority Date:: Mar. 28, 2003); 2 pages.
GenBank accession No. AE015928, (Priority Date:: Mar. 28, 2003); 905 pages.
GenBank Accession No. AE016946, (Priority Date:: Mar. 28, 2003); now replaced by AE015928.
Hedner, "Development of tinzaparin: a heparinase-digested low-molecular-weight heparin", Seminars in Thrombosis and Hemostasis, 2000, vol. 26 (Suppl 1.), pp. 23-29.
Kim et al., "Purification and characterization of a novel heparinase from *Bacteroides stercoris* HJ-15", J. Biochem., 2000, vol. 128, No. 2, pp. 323-328, Tokyo.
Kim et al., "Purification and characterization of acharan sulfate lyases, two novel heparinases, from *Bacteroides stercoris* HJ-15", Eur. J. Biochem., 2001, vol. 268, No. 9, pp. 2635-2641.
Kim et al., "Purification and characterization of heparin lyase I from *Bacteroides stercoris* HJ-15" J. Biochem. Mol. Biol., 2004, vol. 37, No. 6, pp. 684-690.

(Continued)

*Primary Examiner* — Christian Fronda
(74) *Attorney, Agent, or Firm* — Lando & Anastasi, LLP

(57) ABSTRACT

The invention provides recombinant *B. thetaiotaomicron* GAG lyase polypeptides. The invention also provides nucleic acid molecules encoding such polypeptides, recombinant expression vectors containing *B. thetaiotaomicron* GAG lyase nucleic acid molecules, and host cells into which the expression vectors have been introduced. Characterization, diagnostic and therapeutic methods utilizing compositions of the invention are also provided.

14 Claims, 21 Drawing Sheets

OTHER PUBLICATIONS

Myette et al., "The heparin/heparan sulfate 2-0-sulfatase from *Flavobacterium heparinum*. Molecular, cloning, recombinant expression, and biochemical characterization", Apr. 4, 2003, vol. 278, No. 14, pp. 12157-12166.

Pojasek et al., "Histidine 295 and Histidine 510 are curcial for enzymatic degradation of heparan sulfate by heparinase III", Biochemistry, 2000, vol. 39, No. 14, pp. 4012-4019.

Rieger et al., Glossary of Genetics, 5th Ed., 1991, pp. 16-17.

Riley et al., "Heparinase production by anaerobic bacteria", Apr. 1987, vol. 40, No. 4, pp. 384-386.

Riley et al., "Heparinase production by bacteroides", SPP, 1984, vol. 25, No. 99-100, pp. 141-148.

Sasisekharan et al., "Cloning and expression of heparinase I gene from *Flavobacterium heparinum*", Proc. Natl. Acad. Sci., 1993, vol. 90, No. 8, pp. 3660-3664.

Seffernick et al., "Melamine deaminase and atrazine chlorohydrolase: 98 percent identical but functionally different", J. Bacteriology, 2001, vol. 183, No. 8, pp. 2405-2410.

Sen et al., "Developments in directed evolution for improving enzyme functions", Appl. Biochem. Biotechnol., Dec. 2007, vol. 143, No. 3, pp. 212-223.

Sonnenburg et al., "Glycan foraging in vivo by an intestine-adapted bacterial symbiont", Science, 2005, vol. 307, No. 5717, pp. 1955-1959.

Venkataraman et al., "Sequencing Complex Polysaccharides", Science, 1999, vol. 286, No. 5439, pp. 537-542.

Witkowski et al., "Conversion of a b-ketoacyl synthase to a malonyl decarboxylase by replacement of the active-site cysteine with glutamine", Biochemistry, 1999, vol. 38, No. 36, pp. 11643-11650.

Written Opinion received in PCT/US06/43092, dated Feb. 27, 2008.

Xu et al., "A genomic view of the human—*Bacteroides thetaiotaomicron* symbiosis", Science, 2003, vol. 299, No. 5615, pp. 2074-2076.

Xu et al., accession Q89YQ6, Jun. 1, 2003.
Xu et al., accession Q89YS4, Jun. 1, 2003.
Xu et al., accession Q89YS9, Jun. 1, 2003.

* cited by examiner

```
   1 GACAAACGAAAGGCAGCCGTAAGGGTTGCCTTTCGTATTTTTGCACCGTCGATAAACTTAATACCGGATAGAATGAAAAA
  81 ATACATTTGGTTATTATATGATGGCGGCAGGATGCTGACTGCTGACTGCTAAAATACGCAAACACTGATGC
 161 CACTCACCGAACGGGTAAACGTACAGGCTGACTCTGCACGTATCAACCAGATTATTGACGGTTGCTGGGTAGCTGTCGGG
 241 ACGAATAAACCTCATGCCATTCAGCGTGATTTACCAACCTGTTGATGGCAAGCCCTCCTATCGCTTGAACTCAAAAC
 321 TGAAGACAATACACTGGAAGTTATGCCGAGTTATGCCGACTACTGCCGAGTTATGCGAAAGGAGACGTGCCGAGTTTCATATTGCTAGCAACTTCCG
 401 ACGATTCAGGGGATTACCTGCCGACTTTACAGAGACGTTTATTCCTTCTCTTTAGACAGCAATGTCCCACCATCTT
 481 TGTCCGCAAGGAAGTTCCCGCGACTATGAGTTTCGTTTATATTCCTTCTCTTCAGGGCGAGGTGAAGAAACTGACGTTGACGAAT
 561 TGCCCAATGGCACCGAATGCCCGACCGCTGGTCCAGACTCCGACAAAGAATGTCGGACACGCAGAAAACCCAACGATGGTTGTTGAACAGGAGGATACCC
 641 TTGTAGAACTGAAAGATAAAAATGGAAAAACGACCTTCTCAAAAGAATCTGTATATAAGGCAGGAAAAGATGGGCCAGACTGGTTGTTGAACAGGAGGATACCC
 721 CCGGTGAAAGATAAAAATGGAAAAACGACCTTCTCTGATTTATATCAAAGCAAACTCCGACCGTAAATGCTGACAGACAAGATG
 801 GCCATTGGCATTCGGATTTTCCGGAAGACTGTTTTATATCAAAGCAAACTCCGACCGTAAATGCTGACAGACAAGATG
 881 ACCGTTGCAATGCAAACCCGGGAAAGACGCCCGTTATGAACCGCTGACTTCTGAATACAAGGCATCCACCATTGCCTAC
 961 AAATTACCTTTTGCCGATTTCCCGAAAGACTGCTGGATTACTTCCGTGTCCATATCGACTGGACGGTCATGGCAAGGA
1041 AGCGGAAACGATTGTGAGAAGATTCTGATTGGACGTAACGACGAAGACGGGTATTACTTTAAGTTCGGAATTACCGCGTAGGT
1121 TTGTCGATAATGAGAAGATTCTGATTGGACGTAACGACGAAGACGGGTATTACTTTAAGTTCGGAATTACCGCGTAGGT
1201 GATAGTACCGTTCCCGTTCCCGTTTGCTACAATCTCGCAGGATATTCGGAAAGATAA
```

FIG. 1A

```
  1 MKKVI-VIYM MAAGCTMLTA QTKNTQTIMP LTERVNVQAD SARINQIIDG CWVAVGTNKP
 61 HAIQRDFTNL FDGKPSYRFE LKTEDNTLEG YAKGETKGRA EFSYCYATSD DFRGLPADVY
121 QKAQITKTVY HHGKGACPQG SSRDYEFSVY IPSSLDSNVS TIFAQWHGMP DRTLVQTPQG
181 EVKKLTVDEF VELEKTTFFK KNVGHEKVAR LDKQGNPVKD KNGKPVYKAG KPNGWLVEQG
241 GYPPLAFGFS GGLFYIKANS DRKWLTDKDD RCNANPGKTP VMKPLTSEYK ASTIAYKLPF
301 ADFPKDCWIT FRVHIDWTVY GKEAETIVKP GMLDVRMDYQ EQGKKVSKHI VDNEKILIGR
361 NDEDGYYFKF GIYRVGDSTV PVCYNLAGYS ER
```

FIG. 1B

```
BT Hlyase I    1   MKYXVXYXAAGCTMXIAQTKXTQTLMPXTE              XINQXXGCX       IX
FH heparinaseI 1   XXXQXXYXIXXQQ---LFXCSAYAXQKKSGNXPYXXXXXXXXKQKAXXNKXXXXIXX
consensus      1   MKK-IL-i-mm--gc--L-----n------i---RVNVQADSAr---IID--WVAVG-NKF BT Hlyase I    61  HXXXRXFTNLXD              XT         XK        XAXFXCXXXDXXKGLXADX
FH heparinaseI 59  YXXXYXDKLRXN XXXXXXXAXXXXXAXXXXXXTXLXXSXXXXNXXKFXPSX
consensus      61  -AiQ-D----F-GKPSYRFELK-EDNtLEGYA-GETKGR-E-SY-YATS-DFr--P--VY BT Hlyase I    121 XKXXITXXXXHXXAXPXXXXDXEXXXXXLDSXVXXXXXXMDXXXXQXXQX
FH heparinaseI 119 XNXXKLXXXXYXXIXEXXXXSXTXXXXXXFPDXAXXXXXARSXXXAXXEX
consensus      121 Q-AQ--KTVYH-GKG-C-QGSSR-Y-FSVYJPSS---N-STIFAQWHG-P-RTLV-TP-C BT Hlyase I    181 XXKXIXXXXXE

| | |
|---|---|
| 1 | ATGAAAAAATACATTTGGTTATTTATATGATGGCGGCAGGATGCACGATCCTGACTGCTCAGACTAAAAATACGCAAAC |
| 81 | ACTGATGCCACTCACCGAACGGGTAAACGTACAGGCTGACTCTCGCACGTATCAACCAGATTATTGACGGTTGCTGGGTAG |
| 161 | CTGTCGGGACGAATAAACCTCATGCCATTCAGCGTGATTTACCAACCTGTTTGATGCAAGCCCTCCTATCGCTTTGAA |
| 241 | CTCAAAACTGAAGACAATACACTGGAAGGTTATGCCGACGTTATCCGACGACTATGCTGCCGAGTTTCATAATTGCTATGC |
| 321 | AACTTCCGACGATTCAGGGGATTACCTGCCGCGACTATGAGTTTCGGTTTATATTCCTTCTCTTAGACAGCAATGTCTCC |
| 401 | AGGGAGCTTGTCGCCAAGGAAGTTCCCGCGAATGCCGGACGCCTGGTCCAGACTCCTCAGGGCGAGGTGAAGAAACTGACTGT |
| 481 | ACCATCTTTGCCAATGGCACGGAATGCCGACCTTCTTCAAAAGAATGTCGGACGAGAAAAGTGGCCAGACTGGTTGAACAGGGA |
| 561 | TGACGAATTTGTAGAACTGGAAAAAATGGAAAGATAAGGCAGGAGAAAACCCAAACTCCGACCGTTGGTTAAATGCTGACAGA |
| 641 | AAGGTAATCGGTGAAAGATAATCGGATTTTCCGGAGGACTGTTTTATATCAAAGCAAACTCCGACTTCTGAATACAAGGCATCCACCA |
| 721 | GGATAACCCGCCATGGCATTGACGACCGTGCAATGCAAACCCGGGAAAGACGCCCGTTATGAAACCGCTGACTTCCGTGTCCATATCGACTGCGTCTAT |
| 801 | CAAAGATGACCGTGCAATGCAAACCCGGGAAAGACGCCCGTTATGAAACCGCTGACTTCCGTGTCCATATCGACGCGTCTAT |
| 881 | TTGCCTACAAATACCTTTTGCCGAAACGATTGTGAAGATTCTGATAATGAAGAATTCGATGATTATCGGATGAAGACGAAGACGGGTATTACTTTAAGTTCGAATTACC |
| 961 | GGCAAGGAAGCGGAAACGATTGTGAAGATTCTGATAATGAAGAATTCGATGATTATCGGATGAAGACGAAGACGGGTATTACTTTAAGTTCGAATTACC |
| 1041 | CAAACACATTGTCGATAGTACCGTTCCCGTTTGCTACAATCTCGCAGGATATTCGGAAAGATAA |
| 1121 | GCGTAGGTGATAGTACCGTTCCCGTTTGCTACAATCTCGCAGGATATTCGGAAAGATAA |

FIG. 3A

```
MLTAQTKNTQ  TLMPLTERVN  VQADSARINQ  IIDGCWVAVG  TNKPHAIQRD  FTNLFDGKPS  YRFELKTEDN
TLEGYAKGET  KGRAEFSYCY  ATSDDFRGLP  ADVYQKAQIT  KTVYHHGKGA  CPQGSSRDYE  FSVYIPSSLD
SNVSTIFAQW  HGMPDRTIVQ  TPQGEVKKLT  VDEFVELEKT  TFFKKNVGHE  KVARLDKQGN  PVKDKNGKPV
YKAGKPNGWL  VEQGGYPPLA  FGFSGGLFYI  KANSDRKWLI  DKDDRCNANP  GKTPVMKPLT  SEYKASTIAY
KLPFADFPKD  CWITFRVHID  WTVYGKEAET  IVKPGMLDVR  MDYQEQGKKV  SKHIVDNEKI  LIGRNDEDGY
YFKFGIYRVG  DSTVPVCYNL  AGYSER
```

FIG. 3B

```
   1 CAAACACTGATGCCACTCACCGAACGGGTAAACGTACAGGCTGACTCTGCACGTATCAACCAGATTATTGACGGTTGCTG
  81 GGTAGCTGTCGGGACGAATAAACCTCATGCCATTCAGCGTGATTTTACCAACCTGTGATTTGATGCAAGCCCTCCTATCGCT
 161 TTGAACTCAAAACTGAAGACAATACACTGGAAGGTTATGCGACGTTATCAGAAAGGAGAAACGAAAAGGACGTGCCGAGTTTCATATTGC
 241 TATGCAACTTCCGACGATTTCAGGGGATTACCTGCCGACTATGAGTTTCGGTTTATCAGAAGACACAGATCACAAAGCAAAGACAGTTATCATCA
 321 CGGGAAGGGAGCTGTCCGCAAGGAAGTTCCGACGAATGCCGACGGACGCTGGTCCAGACGTTTATATTCTTCTTTAGACAGCAATG
 401 TCTCCACCATCTTGCCCAATGGCACGGATGAACTGGAAAAAACGACCTTCTCAAAAGAATGTCGGACACGGAAAAAGTGGCCAGACTGGA
 481 ACTGTTGACGTAATTGTAGAACGTAACCGGTGAAAGATAAAGAAATGCAGGAGAACCCGATGGTTGTTGAAC
 561 TAAACAAGTAACCGGTGCCATTGGCATTCGGATTTCCGGAGAAGACGCCCGTTGATCGGGAAAAGACGCCCGTTATGAAAGACTGCTGAAGCTG
 641 AGGGAGGATACCCGCCATTGCAATGCAAATGACCGTTGCAATACCTTTTGCCGATTTCCCGAAAGACTGCTGGATGCATGCGTGAAACCGGGCATC
 721 ACAGACAAAGATGACCGTTGCAATGCAAATGACCGTTGCAATACCTTTTGCCGATTCTGAAAGACTGCTGGACTTCTGATACAAGGCATC
 801 CACCATTGCCTACAAATTACCTTTTGCCGATTTCCCGAAAACGGGCATGCGTGAAACCGGGCATGCGTGAAACCGGGCATC
 881 TCTATGGCAAGGAAGCGGAAACGAT-GTGAAAGAAGCGGAAACGATGTGAAAGAAGAATTCTGATAATGAGAAGATTCTGATGAACGAAGGTAAGAAA
 961 GTGAGCAAACACATTGTCGATAATGAGAAGATTCTGATAATGAGAAGATTCTGATGATGGACGTAACGACGAAGACGGGTATTACTTTAAGTTCGAAT
1041 TTACCGCGTAGG-GATAGTACCGTTCCCGTTGCTACACAATCTCGCAGGATATTCGGAAAGATAA
```

FIG. 4A

QTIMPLTERV NVQADSARIN QIIDGCWVAV GTNKPHAIQR DFTNLFDGKP SVRFELKTED NTLEGYAKGE
TKGRAEFSYC YATSDDFRGL PADVYQKAQI TKTVYHHGKG ACPQGSSRDY EFSVYIPSS

```
   1 atgaataaaa ccctgaaata tatcgtcctg ctgacatttg cttgtttcgt aggcaaaggc
  61 tatgcccaag agttgaaaag cgaggtattc tcgcttctca acctggacta ccccggattg
 121 gagaaagtaa aagccttaca tcaggaaggc aaagatgagg atgccgcaaa agcactgctc
 181 gactactacc gtgcacgtac gaatgtgaag acgccggata ttaatctgaa aaagatcact
 241 atcggcaaag aagaacagca atgggcggat gacggattga agcatacatt ctttgttcac
 301 aaaggctatc agccttctta caactacgga gaagatatca actggcaata ctggccgtg
 361 aaagacaatg aactccgctg gcagttgcac cgtcataaat ggtttactcc gatgggtaag
 421 gcataccgtg tatcgggtga cgagaaatat gccaaagaat gggcatacca atacatcgac
 481 tggattaaaa agaatccgtt ggtgagatgc gacaaactcg atcagttcac ggaagtcagt
 541 ggtagcatta aaccatcagt ggaaaatgta cgtttcgcat ggcgtccgct ttctttcact
 601 aatcgtctgc aggatcagac tacccagttc cagttgttcc tatcataaac atgccgtaca
 661 ccggatttcc tgactgaatt tctggtgaac tcacttgttg ttcgaagccc acgtatgat tatctggct
 721 aattactctg atcagggtaa tcacttgttg agaagctccg gcctggagaa aaagcggtat ttatgcaggt
 781 gcattcttcc cggaatttaa agaagctccg gcctggagaa aaagcggtat cgacattctg
 841 aaccgtgaag taaacgtaca ggtttacaac gatggcggcc agtttgaact tgacccgcat
 901 tatcatcttg ctgctatcaa tatcttctgc aaggcattgg gtatcgcgga tgttaacgga
 961 ttccgtaatg agttcccaca tatctcttca ggaatatctg gatactatcg aaaagatgat catgttctat
1021 gccaatatt cttcccgga ttacacaaat ccgtgtttca gtgatgctaa aatcacagaa
1081 aagaaagaaa tgctgaagaa tgctcgtgca ctatcgtgca tgatgcaaac tgttcccgaa aaacgaaact
1141 atcaagtatt tgcaacagaa cggcaaagaa cggcgcgttac tgttccgtac ccgattatat gtcgaaaagt
1201 ttcctgaaat cagtttctt tgtgttccgc aattcctggg gaatgatgc ccgattatat tacacaaatg
1261 gtagtaaaag ccggtccgaa aggtttctga cactgtcagc cggataacgg tactttcgaa
1321 atgtggttta acggcaagaa cctgttccca gactccggtt cgtatgtgta tgccggtgaa
1381 ggcgaagtga tggaacaacg tggaacaacg caactggcat cgtcagactt ccgtacacaa caccgtgact
1441 ctggacaata agatctgga accaaccgaa tctgttacta actgtggca gccgaaggc
1501 aatatccaga ccttggttac agaaaaccca agctacaaga acttcaagca cgccgttcg
1561 gtcttcttcg tagacaatac ctactttgtc attgtagatg aagtatcagg cagcgccaaa
1621 ggttctgtca acctgcacta tcagatgccg aaaggtgaga tagccaacag ccgtgaagac
1681 atgacattcc tgactcaatt cgaagatgga agcaacatga aacttcaatg cttcggcct
1741 gaaggcatga gcatgaaaaa cgaagccggga tgtgttccta ctgcatatcg caagcgctac
1801 atgtggttta acggcaagaa caacgtaaag aaagacaatg agaatgcggt acgttacatc
1861 aaacagttac atgttttcatt acccagtcaa gatgcccta aatttgacgc taagttcaag
1921 aacaaaacgt tcgatgaaaa gaagagcgca ataaagtga aagtaaacgg caagaaacag
1981 tcattaaaat ataattata a
```

FIG. 5A

```
  1    mnktlkyivl ltfacfvgkg yaqelksevf sllnldypgl ekvkalhqeg kdedaakall
 61    dyyrartnvk tpdin-kkit igkeeqqwad dglkhtffvh kgyqpsynyg edinwqywpv
121    kdnelrwq-h rhkwftpmgk ayrvsgdeky akewayqyid wikknplvkm dkkevevysd
181    gsvkgvevnv rfawrplevs nrlqddqttqf qlfipspsft pdfltefivn yhkhavhila
241    nysdqgnh-l feaqrmiyag affpefkeap awrksgidil nrevnvqvyn dgqqfeldph
301    yhlaainifc kalgiadvng frnefpqeyl dtiekmimfy anisfpdytn pcfsdakite
361    kkemlknyra wsklfpknet ikylatdgke galpdymskg flksgffvfr nswgmdatqm
421    vvkagpkgfw hcqpdngtfe mwfngknlfp dsgsyvyage gevmeqrnwh rqtsvhntvt
481    ldnknlette svtklwqpeg niqtlvtenp syknfkhrrs vffvdntyfv ivdevsgsak
541    gsvnlhyqmp kgeiansred mtfltqfedg snmklqcfgp egmsmkkepg wcstayrkry
601    krmnvsfnvk kdnenavryi tviypvkksa dapkfdakfk nktfdengle ievkvngkkq
661    slkykl
```

1
ATGATGAAACAACGATATTATATTTTCCTGTTATTTGTAGCTATGCTTTCCTATAGTGGATATGCG<u>CAG</u>AAAAGCATCCT
81
GCGTCTGAGTCAGCAGACGCTGATGCATGAAGTCCGCGAAACACCTTCTCCACTGGGCGGTCAGCACATAGCAGTCAATC
161
CGCCGCGTTTCATGTGGCCGGATAAGTTCCCCCACCTCGGACCTGTGCTTGACGGAGTGGAAGAAGAAGATCACAAACCG
241
GAAGTGACATACCGCATCCGTATCGCACGTGATCCTGAGTTTAAATCGGAAGTAATGACCGCCGAAAGAAACTGGGCTTT
321
CTTCAATCCTTTCAAACTCTTTGAAAAAGGGAAATGGTATTGGCAGCACGCCTACCTTGATAAGGACGGCAAAGAAGAAT
401
GGTCGCCCGTCTATCATTTCTATGTGGACGAGCAGACACGTACGTTCAATCCTCCCTCCTTGCAAGAAGTGCTGGCGAAG
481
TTCTCTCAAAGCCATCCCCGTATCCTGCTCGATGCCAAAGACTGGGATCAGATCATCGAGCGGAACAAGAATAATCCGGA
561
AGCGCAGCTCTATATTCAGAAAGCAAGGAAATGCCTCAATCATCCATTGAAACATCTGGAGGAGGAAATCGATACCACCC
641
AAGTAGTCAAATTGACGAACATCGTACAATATCGCTCGGCATTGATTCGGGAAAGCCGCAAGATAGTAGACCGCGAAGAA
721
GCGAACATAGAAGCTATGGTACGCGCTTATCTGCTGACGAAAGACGAAGTGTACTACAAAGAAGGTATCAAACGTCTTTC
801
CGAAATTCTTTCGTGGAAAGACAGTAAGTACTTCGCAGGAGATTTCAACCGCTCCACGATTCTGTCCATGAGTACTTCCG
881
CTTATGATGCATGGTACAATCTGTTAACGCCTGCCGAGAAACAGTTGCTTCTCGAAACGATCAGCGAAAACGCCCATAAG
961
TTTTATCATGAATATGTGAATCATCTGGAAAACCGTATTGCCGACAATCATGTATGGCAGATGACTTTCCGTATTCTGAA
1041
TATGGCAGCTTTTGCTACATACGGTGAATTGCCGATGGCTTCCACTTGGGTAGATTATTGCTATAACGAATGGGTATCCC
1121
GTCTGCCGGGACTCAACACCGACGGAGGATGGCACAACGGTGACTCTTATTTCCATGTCAACCTTCGTACATTGATCGAA
1201
GTTCCCGCTTTCTATTCACGTATCAGCGGTTTCGATTTCTTTGCCGATCCCTGGTATAACAACAATGCGCTCTATGTAAT
1281
CTATCATCAGCCTCCGTTCTCCAAATCTGCGGGACACGGCAACTCCCATGAAACGAAAATGAAACCGAACGGGACACGGG
1361
TCGGCTATGCGGATGCTTTAGCACGTGAATGCAATAATCCGTGGGCAGCCGCCTACGCACGTACCATTCTGGAGAAAGAA
1441
CCGGATATCATGAAAAAGTCTTTTCTTGGAAAAGCAGGTGATCTGACCTGGTATCGCTGCATTACTGACAAGGCACTCCC
1521
GAAAGAAGAACACTCATTGGCAGAGTTGCCGATGACGAAAGTATTTAATGAAACGGGAATTGCTACGATGCATACTTCGT
1601
TGGGGGATATAGAAAAGAACACAATGTTGTCATTCCGTTCCAGTCCATACGGTTCAACTTCGCACGCATTGGCCAATCAG
1681
AATGCATTTAATACCTTCTATGGAGGCAAGGCGATCTTCTATAGCAGCGGACATCGTACCGGTTTTACCGATGACCATTG
1761
TATGTATTCCTATCGAAACACCCGTGCGCACAATAGTATTCTGGTCAACGGAATGACTCAGACTATAGGAACGGAAGGTT
1841
ACGGATGGATTCCCCGTTGGTATGAAGGAGAAAAGATTTCGTATATGGTGGGAGACGCTTCCAATGCTTACGGAAAGATC
1921
ACAGCTCCTATCTGGTTGAAACGTGGTGAACTTTCCGGCACGCAGTACACTCCCGAAAAGGGATGGGATGAGAACAAACT
2001
GAAGATGTTCCGTCGGCACACATCATTCAATTAGGCAATACGGGAGTGTATGTGATTTATGATGAACTGGAAGGAAAAGAAG
2081
CGGTCACATGGAGCTATCTGCTGCATACGGTAGAACTTCCGATGGAAATGCAGGAACTTCCTGATGAAGTGAAAGTTACG

Fig. 8

```
2161
GGAAAGAATAAGGATGGAGGCATCTCTGTTGCTCATCTTTTCAGTTCGGCAAAGACGGAACAGGCCATCGTAGATACCTT
2241
CTTCTGCGCTCCAACCAACTGGAAGAATGTAACCAATGCCCAAGGAAAAGCTGTGAAGTATCCCAATCACTGGCATTTTT
2321
CGTCTACTACCATTCCATGTAAAACTGCCCGTTTCCTCACCGTTATGGATACACATGGAAATAACCGTGCGGATATGAAA
2401
GTGGTTCGCCAAGGCAATACCGTACAAGTAGGCGACTGGATTATTACCTGCAATCTGACGGAGAAAGGGAAAGCGGCAAT
2481
CAGCGTCACCCATCAAGCGGAAAAGGTTTCTTTGAAATACGATGCCGGCAAGAAGGAAGGTGCGACTATCATCACAGATC
2561 AAGTACAAGGGAAACAGGTCAATAAGGTTCTGACTGACTATTACCGGATTTTGAGATATAA
```

Fig. 8 (cont'd)

```
  1  mkqryyifll fvamlsysqy aqksilrlsq qtlnhevret psplggqhia vnpprfmwpd
 61  kfphlgpvld gveeedhkpe vtyririard pefksevmta ernwaffnpf klfekgkwyw
121  qhayldkdgk eewspvyhfy vdeqtrtfnp pslqevlakf sqshprilld akdwdqiier
181  nknnpeaqly iqkarkclnh plkhleeeid ttqvvkltni vqyrsalire srkivdreea
241  nieamvrayl ltkdevyyke gikrlseils wkdskyfagd fnrstilsms tsaydawynl
301  ltpaekqlll etisenahkf yheyvnhlen riadnhvwqm tfrilnmaaf atygelpmas
361  twvdycynew vsrlpglntd ggwhngdsyf hvnlrtliev pafysrisgf dffadpwynn
421  nalyviyhqp pfsksaghgn shetkmkpng trvgyadala recnnpwaaa yartilekep
481  dimkksflgk agdltwyrci tdkalpkeeh slaelpmtkv fnetgiatmh tslgdieknt
541  mlsfrsspyg stshalanqn afntfyggka ifyssghrtg ftddhcmysy rntrahnsil
601  vngmtqtigt egygwiprwy egekisymvg dasnaygkit apiwlkrgel sgtqytpekg
661  wdenklkmfr rhiiqlgntg vyviydeleg keavtwsyll htvelpmemq elpdevkvtg
721  knkdggisva hlfssakteq aivdtffcap tnwknvtnaq gkavkypnhw hfssttipck
781  tarfltvmdt hgnnradmkv vrqgntqvg dwiitcnlte kgkaaisvth qaekvslkyd
841  agkkegatii tdqvqgkqvn kvltdylpdf ei
```

```
   1 - ATGAAGAACATCTTCTTTATTTGCTTTTGTGCGCTATTCGCATTTAGTGGATGCGCAGAC -   60
  61 - GATGATGATGATCTATTAACCGGAGGGAATGTAGATATAGATCTGCTTCCTGATGCCAAA -  120
 121 - CCAAACGATGTTGTTGATCCTCAAGTATTCGAGGCTATCAACCTCAACTACCCCGGTCTG -  180
 181 - GAAAAAGTTAAAGAATTCTACGAGGCAGGCGAACATTATTATGCAGCCAATGCTTTATTG -  240
 241 - GAATACTATAGAACGAGAACCAATGTTACAAATCCGAACTTATCTTTAATTAATGTGACG -  300
 301 - ATCTCAGAAGCAGAGCAGGCAAAAGCTGATTATGCACTGGTAGATTATCGCTTTCATGTT -  360
 361 - AACAACTTCTATGAAGATAAGGAAACCCTGAAACCCTATTCAGTAAAACAAGACGGAGGT -  420
 421 - ATAAACTGGGAGTATTCACCGAAAGATGCATCTGATGAATATCAGAAACAACTTCATCGC -  480
 481 - CATCAGTGGTTCATCCCCCAAGCCAAAGCTTACCGTGTAAGTGGAGATGAGAAATACATT -  540
 541 - CAATCATGGATTGAGGTATATAAGAATTGGATAGAAAACAATCCGAAGCCTACAACAGGA -  600
 601 - CCTAATACTACCTCATGGTGGCAGTTACAGGTATCTACCCGTATCGGTGACCAAGTACAA -  660
 661 - TTGCTTGAATACTTCAAGAACTCTGTTAATTTTACTCCGGAATGGCTTTCTACATTCTTG -  720
 721 - GTAGAATTTGCAGAACAAGCAGACTTTCTCGTAGATTATCCGTATGAATCAGGAGGTAAC -  780
 781 - ATACTTATATCACAAGCGAATGCATTGGCTACTGCCGGAACGTTAATGCCGGAATTTAAG -  840
 841 - AATGCGGAGAAATGGATGAATACAGGATATCAGATACTTAGCGAAGAAGTACAAAATCAA -  900
 901 - ATTATGAGTGACGGATGGCACAAGGAAATGTCGCTCCACTATCATATCGGTATCGTTGCG -  960
 961 - GATTTCTACGAGGCAATGAAATTAGCAGAGGCAAACCAACTCTCCAGTAAATTGCCGTCA - 1020
1021 - GATTTTACAGAACCACTGCGTAAAGCAGCAGAAGTAGTGATGTACTTCACATATCCTAAT - 1080
1081 - TACTTTATCAAGGGTTCCGATAATGTGGTCCCAATGTTCAACGACTCATGGAGCCGGACA - 1140
1141 - CGTAATGTCCTTAAAAATACGAACTTTAAGCAATATGTGGAAATGTTCCCGGATAGTGAA - 1200
1201 - GAATTGAAATATATGCAAACTGCCGGAAATGGTGGAACAGCACAGGGACGTACCCCCAAT - 1260
1261 - AATGATATGAAGCTATTCGACCAGGCAGGATATTATGTATTACGAAATGGTTGGACACCG - 1320
1321 - GCTTCTACAGTCATGATTTTAAGCAATAACAAGAGTAATGATGCTTCTAATTCACTTAGT - 1380
1381 - GCTTATAGTCATAACCAGCCAGATAATGGAACTTTCGAACTTTACCATAACGGACGAAAT - 1440
1441 - TTTTTCCCTGATTCAGGTGTGTGTACTTATTATACCAGCGGTGGAGACAATGACTTACGT - 1500
1501 - TACTGGTTCCGTGGTATCGATAAACACAATACTTTATCAATCGGAAAACAGAATATCAAA - 1560
1561 - AAGGCAGCAGGCAAACTGTTGAAATCAGAGGAAGGAGCGACTGAATTAGTTGTATTTGAG - 1620
1621 - AATCAAGGATATGATAACTTAAAGCACCGTCGTGCAGTCTTTTACGTAAACAAAAAATTC - 1680
1681 - TTTGTATTAGTAGATGAAGGTATTGGAAATGCAGAAGGTACTATTAATCTAAGTTTCAAT - 1740
1741 - CTTTGCGAAGGCACTGCCAGCGAAGTTGTTATGGATACAGATAAAAATGGAGTCCATACA - 1800
1801 - GCATTCAGCAATAATAACATTATAGTCCGCACTTTTGCCAATAAAGCAGTAACCTGT - 1860
1861 - TCTCCATTCACGGGGCGTATAGCCTATCTCGTAGACGGGGCTTACAACACACGTCAATCT - 1920
1921 - TATACCATCGATATGAATAAGAGTGCTGATGAAACCGCACGTTACATTACAGTTATTCTT - 1980
1981 - CCAGTCAATGGAAGTACTGATACGTCCAGTATCTCAGCCAAATTCATAGATAGCGGATAT - 2040
2041 - TCCGAAAACAGCGCTTCTGTAGAAGTAAGTGTGAATGGAGAGACACATACATTATCTTAT - 2100
2101 - ACCTTATAA - 2109
```

FIG. 13

```
  1 mknifficfc alfafsqca dddd lltggn vdidllpdak pndvvdpqvf eainlnypgl
 61 ekvkefyeag ehyyaanall eyyrtrtnvt npnlslinvt iseaeqakad yalvdyrfhv
121 nnfyedketl kpysvkqdgg inweyspkda sdeyqklhr hqwfipqaka yrvsgdekyi
181 qswievyknw iennpkpttg pnttswwqlq vstrigdqvq lleyfknsvn ftpewlstfl
241 vefaeqadfl vdypyesggn ilisqanala tagtlmpefk naekwmntgy qilseevqnq
301 imsdgwhkem slhyhigiva dfyeamklae anqlssklps dfteplrkaa evvmyftypn
361 yfikgsdnvv pmfndswsrt rnvlkntnfk qyvemfpdse elkymqtagn ggtaqgrtpn
421 ndmklfdqag yyvlrngwtp astvmilsnn ksndasnsls ayshnqpdng tfelyhngrn
481 ffpdsgvcty ytsggdndlr ywfrgidkhn tlsigkqnik kaagkllkse egatelvvfe
541 nqgydnlkhr ravfyvnkkf fvlvdegign aegtinlsfn lcegtasevv mdtdkngvht
601 afsnnnniiv rtfankavtc spftgriayl vdgayntrqs ytidmnksad etaryitvil
661 pvngstdtss isakfidsgy sensasvevs vngethtlsy tl
```

HEPARAN SULFATE GLYCOSAMINOGLYCAN LYASE AND USES THEREOF

CROSS-REFERENCE TO RELATED APPLICATIONS

This application is a divisional of U.S. application Ser. No. 12/436,751 filed May 6, 2009 now U.S. Pat. No. 7,888,072, which is a divisional of U.S. application Ser. No. 11/948,561 filed Nov. 30, 2007 now U.S. Pat. No. 7,691,613, which is a divisional of U.S. application Ser. No. 11/592,622 filed Nov. 3, 2006 now U.S. Pat. No. 7,691,612, which is a continuation-in-part application of and claims priority to U.S. application Ser. No. 11/265,908, filed on Nov. 3, 2005 now U.S. Pat. No. 7,767,420.

BACKGROUND OF THE INVENTION

Heparin and heparan sulfate represent a class of glycosaminoglycans characterized by a linear polysaccharide of D-glucosamine linked to hexuronic acid (Linhardt, R. J. (1991) Chem. Ind. 2, 45-50; Casu, B. (1985) Adv. Carbohydr. Chem. Biochem. 43, 51-134). Heparin and heparan sulfate are complex carbohydrates that play an important functional role in the extracellular matrix of mammals. These polysaccharides modulate and regulate critical biochemical signaling pathways which impinge on normal physiological processes such as cell and tissue morphogenesis, cell-cell interactions, and growth and differentiation. These polysaccharides also play a critical role in various pathologies including wound healing, tumor growth and metastasis, certain neurodegenerative disorders and microbial pathogenesis, to name a few.

Much of the current understanding of heparin and heparan sulfate sequence has relied on studies of their biosynthesis (Linhardt, R. J., Wang, H. M., Loganathan, D., and Bae, J. H. (1992) Biol. Chem. 267, 2380-2387; Lindahl, U., Feingold, D., and Roden, L. (1986) Trends Biochem. Sci. 11, 221-225; Jacobson, I., and Lindahl U. (1980) J. Biol. Chem. 255, 5094-5100; Lindahl, U., and Kjellen, L. (1987) in The Biology of Extracellular Matrix Proteoglycans (Wight, T. N., and Mecham R., eds) pp. 59-104, Academic Press, New York).

Heparan sulfate, which is chemically related to heparin, is present on the cell surface and within the extracellular matrix (ECM) of virtually every mammalian cell type. These heparin-like glycosaminoglycans (HLGAGs) are present in this extracellular environment as protein-polysaccharide conjugates known as proteoglycans. It is increasingly recognized that HLGAGs play much more than a mere structural role as they interact in a functional manner with numerous proteins of the extracellular matrix, such as laminin, fibronectin, integrins, and collagen. As such, HLGAGs (as part of proteolycans) help to define the biological properties of the matrix. These HLGAGs also interact with an array of cytokine-like growth factors and morphogens present within the extracellular matrix by facilitating their biochemical interaction with receptors and by protecting them from proteolytic degradation. For example, heparin potentates the biological activity of aFGF, as reported by Thornton, et al., Science 222, 623-625 (1983), possibly by potentiating the affinity of aFGF for its cell surface receptors, as reported by Schreiber, et al., Proc. Natl. Acad. Sci. USA 82, 6138-6142 (1985). Heparin protects aFGF and bFGF from degradation by heat, acid and proteases, as reported by Gospodarowicz and Cheng, J. Cell Physiol. 128, 475-4 84 (1986); Rosengart, et al., Biochem. Biophys. Res. Commun 152, 432-440 (1988); and Lobb Biochem. 27, 2572-2578 (1988). bFGF is stored in the extracellular matrix and can be mobilized in a biologically active form by the hydrolyzing activity of enzymes such as heparanase as reported by Vlodavsky, et al., Proc. Natl. Acad. Sci. USA 84, 2292-2296 (1987) and Folkman, et al., Am. J. Pathol. 130, 393-400 (1988) and Emerson et. al. Proc. Natl. Acad. Sci. USA 101(14): 4833-8 (2004).

The binding of FGF to heparan sulfate is a prerequisite for the binding of FGF to its high affinity receptor on the cell surface, as reported by Yayon, et al., Cell 64, 841-848 (1991) and Papraeger, et al., Science 252, 1705-1708 (1991). A specific heparan sulfate proteoglycan has been found to mediate the binding of bFGF to the cell surface, as described by Kiefer, et al., Proc. Natl. Acad. Sci. USA 87, 6985-6989 (1990).

Heparin lyases, such as heparinases, are a general class of enzymes that are capable of specifically cleaving the major glycosidic linkages in heparin and heparan sulfate. Three heparinases have been identified in *Flavobacterium heparinum*, a GAG-utilizing organism that also produces exoglycuronidases, glycosidases, sulfoesterases, and sulfamidases and other enzymes which further act on the lyase-generated oligosaccharide products (Yang, et al. J. Biol. Chem. 260, 1849-1857 (1987); Galliher, et al. Eur. J. Appl. Microbiol. Biotechnol. 15, 252-257 (1982). These lyases are designated as heparinase I (heparinase, EC 4.2.2.7), heparinase II (heparinase II, no EC number) and heparinase III (heparinase EC 4.2.2.8). The three purified heparinases differ in their capacity to cleave heparin and heparan sulfate: heparinase I primarily cleaves heparin, heparinase III specifically cleaves heparan sulfate, and heparinase II acts on both heparin and heparan sulfate. Several *Bacteroides* species (Saylers, et al. Appl. Environ. Microbiol. 33, 319-322 (1977); Nakamura, et al. J. Clin. Microbiol. 26, 1070-1071 (1988)) also produce heparin lyases. A heparin lyase has also been purified to apparent homogeneity from an unidentified soil bacterium by Bohmer, et al. J. Biol. Chem. 265, 13609-13617 (1990).

SUMMARY OF THE INVENTION

The invention is based, in part, on the discovery and recombinant expression of glucosaminoglycan (GAG) lyases from *Bacteroides thetaiotaomicron*, hereafter referred to as "*B. thetaiotaomicron* GAG lyases", e.g., *B. thetaiotaomicron* GAG lyase I, *B. thetaiotaomicron* GAG lyase II *B. thetaiotaomicron* GAG lyase III, and *B. thetaiotaomicron* GAG lyase IV, useful, inter alia, in the structure-specific cleavage of heparin and/or heparan sulfate, and, in some cases, chondroitin sulfate and dermatan sulfate. Thus, the invention includes methods, compositions and kits with a *B. thetaiotaomicron* GAG lyase or functional fragments thereof and combinations of *B. thetaiotaomicron* GAG lyases or functional fragments thereof, for, e.g., characterization or modification of glycosaminoglycans (GAGs) such as heparin-like glycoaminoglycans (HLGAGs), e.g., heparin and heparan sulfate or, e.g., characterization or modification of non-heparin/heparan sulfate GAGs, e.g., chondroitin sulfate and dermatan sulfate. For example, the methods, compositions and kits can be used to analyze and monitor heterogeneous populations of GAGs, e.g., HLGAGs. In other aspects, the methods, compositions and kits can be used to modify the structure and/or activity of GAGs, e.g., HLGAGs.

Accordingly, in one aspect, the invention features *B. thetaiotaomicron* GAG lyase polypeptides, or functional fragments thereof, e.g., *B. thetaiotaomicron* GAG lyase polypeptides, or functional fragments thereof, having the amino acid sequence shown in SEQ ID NOs:2, 4, 6, 8, 10, 23, 29, 34, 37 or 39; an amino acid substantially identical to the amino acid sequence shown in SEQ ID NOs:2, 4, 6, 8, 10, 23, 29, 34, 37 or 39; or an amino acid encoded by a nucleic acid molecule that hybridizes under stringent hybridization conditions to a nucleic acid molecule comprising the nucleic acid sequence of SEQ ID NOs:1, 3, 5, 7, 9, 22, 28, 33, 36 or 38, wherein the nucleic acid encodes a full length *B. thetaiotaomicron* GAG lyase protein, or functional fragments thereof.

In another aspect, the invention features a composition that includes a *B. thetaiotaomicron* GAG lyase polypeptide, *B. thetaiotaomicron* GAG lyase polypeptides, or functional fragments thereof, e.g., *B. thetaiotaomicron* GAG lyase polypeptides, *B. thetaiotaomicron* GAG lyase polypeptides, or functional fragments thereof, described herein. In one embodiment, the composition further comprises one or more HLGAG degrading enzyme, e.g., one or more heparinase and/or one or more GAG lyase polypeptide other than a *B. thetaiotaomicron* GAG lyase polypeptides. For example, the composition can further include one or more of: an unsaturated glucuronyl hydrolase (e.g., *F. heparinum* Δ4,5 glycuronidase; *B. thetaiotaomicron* Δ4,5 glycuronidase); a glucuronyl hydrolase (e.g., mammalian α-iduronidase, β-glucuronidase); a sulfohydrolase (e.g., *F. heparinum* 2-O-sulfatase, 6-O-sulfatase, 3-O-sulfatase: *B. thetaiotaomicron* 6-O-sulfatase; mucin desulfating enzymes; mammalian N-acetylglucosamine-6-sulfatase; mammalian iduronic acid-2-sulfatase); an N-sulfamidase (e.g., *F. heparinum* N-sulfamidase; mammalian heparan-N-sulfatase); an arylsulfatase; a hexosaminidase; a glycosyl hydrolase (e.g., endo-N-acetyl glucosaminidase); a heparinase (e.g., *Flavobacterum heparinum* heparinase I, *Flavobacterum heparinum* heparinase II, *Flavobacterum heparinum* heparinase III, *Flavobacterum heparinum* heparinase IV aka heparinases from *Cytophaga heparina* or *Pedobacter heparinum*), mammalian heparanase, bacteriophage K5 heparan lyase, and functional fragments and variants thereof. Such compositions can be used, e.g., to cleave a HLGAG such as heparin and/or heparan sulfate, e.g., to characterize a preparation of HLGAGs such as heparin and/or heparan sulfate.

In another aspect, the invention features a method of specifically cleaving an HLGAG, e.g., heparin or heparan sulfate, that includes contacting an HLGAG with a *B. thetaiotaomicron* GAG lyase polypeptide, *B. thetaiotaomicron* GAG lyase polypeptides, or functional fragments thereof, e.g., a *B. thetaiotaomicron* GAG lyase polypeptide, *B. thetaiotaomicron* GAG lyase polypeptides, or functional fragments thereof, described herein. In one embodiment, the HLGAG is cleaved into di-, tri-, tetra-, penta-, hexa-, octa-, and/or deca-saccharides and, e.g., the method further includes determining the sequence of the di-, tri-, tetra-, penta-, hexa-, octa-, deca- and/or longer saccharides of the HLGAG. In one embodiment, the method further includes contacting the HLGAG with one or more HLGAG degrading enzyme, e.g., a heparinase polypeptide or a GAG lyase polypeptide other than a *B. thetaiotaomicron* GAG lyase polypeptide. For example, the HLGAG degrading enzyme can be one or more of: an unsaturated glucuronyl hydrolase (e.g., *F. heparinum* Δ4,5 glycuronidase; *B. thetaiotaomicron* Δ4,5 glycuronidase); a glucuronyl hydrolase (e.g., mammalian α-iduronidase, β-glucuronidase); a sulfohydrolase (e.g., *F. heparinum* 2-O-sulfatase, 6-O-sulfatase, 3-O-sulfatase: *B. thetaiotaomicron* 6-O-sulfatase; mucin desulfating enzymes; mammalian N-acetylglucosamine-6-sulfatase; mammalian iduronic acid-2-sulfatase); a N-sulfamidase (e.g., *F. heparinum* N-sulfamidase; mammalian heparan-N-sulfatase); an arylsulfatase; a hexosaminidase; a glycosyl hydrolase (e.g., endo-N-acetyl glucosaminidase); a heparinase (e.g., *Flavobacterum heparinum* heparinase I, *Flavobacterum heparinum* heparinase II, *Flavobacterum heparinum* heparinase III, *Flavobacterum heparinum* heparinase IV aka heparinases from *Cytophaga heparina* or *Pedobacter heparinum*), mammalian heparanase, bacteriophage K5 heparan lyase, and functional fragments and variants thereof.

In another aspect, the invention features methods for analyzing heterogeneous populations of HLGAGs, e.g., heparin (e.g., UFH, LMWH, and synthetic heparins), and heparan sulfate, that include contacting the population with a *B. thetaiotaomicron* GAG lyase polypeptide, *B. thetaiotaomicron* GAG lyase polypeptides, or functional fragments thereof, e.g., a *B. thetaiotaomicron* GAG lyase polypeptide, *B. thetaiotaomicron* GAG lyase polypeptides, or functional fragments thereof, described herein. Thus, in some aspects, the invention relates to methods and products associated with analyzing and monitoring heterogeneous populations of HLGAGs, e.g., to thus defining the structural signature and activity of heterogeneous populations of HLGAGs, using a *B. thetaiotaomicron* GAG lyase polypeptide, *B. thetaiotaomicron* GAG lyase polypeptides, or functional fragments thereof, e.g., a *B. thetaiotaomicron* GAG lyase polypeptide, or functional fragment thereof, described herein.

In some embodiments, the method includes determining the structural signature of one or more batches of an HLGAG product that has been contacted with a *B. thetaiotaomicron* GAG lyase polypeptide, *B. thetaiotaomicron* GAG lyase polypeptides or functional fragments thereof, e.g., a *B. thetaiotaomicron* GAG lyase polypeptide, *B. thetaiotaomicron* GAG lyase polypeptides, or functional fragments thereof, described herein. In some embodiments, the method further includes selecting a batch as a result of the determination. In some embodiments, the method further includes comparing the results of the determination to preselected values, e.g., a reference standard. The preselected value can be, e.g., the presence or absence or a set value (e.g., mole % or area under the curve) of one or more di-, tri-, tetra-, penta-, hexa-, octa-, and/or deca-saccharide associated with cleavage of the HLGAG with a *B. thetaiotaomicron* GAG lyase polypeptide, *B. thetaiotaomicron* GAG lyase polypeptides, or functional fragments thereof, e.g., a *B. thetaiotaomicron* GAG lyase polypeptide, *B. thetaiotaomicron* GAG lyase polypeptides, or functional fragment thereof, described herein.

For any of the methods described herein, a completely or partially *B. thetaiotaomicron* GAG lyase polypeptide (or polypeptides) digested sample can be analyzed to determine the structural signature by, e.g., one or more of mass spectroscopy (e.g., matrix assisted laser desorption/ionization mass spectroscopy (MALDI-MS)), nuclear magnetic resonance (NMR) spectroscopy (e.g., 1D NMR or 2D NMR), gel electrophoresis, capillary electrophoresis (CE), reverse-phase column chromatography (e.g., HPLC, e.g., HPLC with a stationary phase dynamically coated with a quanternary ammonium salt), ion-pair HPLC, e.g., strong anion exchange HPLC (SAX-HPLC). The methods described herein can further include digesting the sample with one or more HLGAG degrading enzyme, e.g., a heparinase or a heparin lyase polypeptide other than a *B. thetaiotaomicron* GAG lyase polypeptide. For example, the HLGAG degrading enzyme can be one or more of: an unsaturated glucuronyl hydrolase (e.g., *F. heparinum* Δ4,5 glycuronidase; *B. thetaiotaomicron* Δ4,5 glycuronidase); a glucuronyl hydrolase (e.g., mammalian α-iduronidase, β-glucuronidase); a sulfohydrolase (e.g., *F. heparinum* 2-O-sulfatase, 6-O-sulfatase, 3-O-sulfatase: *B. thetaiotaomicron* 6-O-sulfatase; mucin desulfating enzymes; mammalian N-acetylglucosamine-6-sulfatase; mammalian iduronic acid-2-sulfatase); a N-sulfamidase (e.g., *F. heparinum* N-sulfamidase; mammalian heparan-N-sulfatase); an arylsulfatase; a hexosaminidase; a glycosyl hydrolase (e.g., endo-N-acetyl glucosaminidase); a heparinase (e.g., *Flavobacterum heparinum* heparinase I, *Flavobacterum heparinum* heparinase II, *Flavobacterum heparinum* heparinase III, *Flavobacterum heparinum* heparinase IV aka heparinases from *Cytophaga heparina* or *Pedobacter heparinum*), mammalian heparanase, bacteriophage K5 heparan lyase, and functional fragments and variants thereof.

In another aspect, the invention features an HLGAG preparation (e.g., a heparin or heparan sulfate preparation) produced by contacting an HLGAG preparation with a *B. thetaiotaomicron* GAG lyase polypeptide, *B. thetaiotaomicron* GAG lyase polypeptides, or functional fragments thereof, e.g., a *B. thetaiotaomicron* GAG lyase polypeptide, *B. thetaiotaomicron* GAG lyase polypeptides, or functional fragments thereof, described herein. In one embodiment, the HLGAG preparation (e.g., the heparin or heparan sulfate preparation) has one or more of reduced anti-Xa activity and anti-IIa activity, e.g., as compared to a reference standard, e.g., as compared to a commercially available heparin or heparan sulfate or as compared to the heparin or heparan sulfate preparation prior to contacting with a *B. thetaiotaomicron* GAG lyase polypeptide. In some embodiments, anti-Xa activity is reduced while anti-IIa activity is maintained or increased. In other embodiments, anti-IIa activity is reduced while anti-Xa activity is maintained or enhanced. In other embodiments, anti-Xa activity and anti-IIa activity are reduced. Such preparation can be useful, e.g., for applications where reduced anti-Xa activity and/or anti-IIa activity is desirable, e.g., such as the use of heparin or heparan sulfate as a carrier for another agent, e.g., a therapeutic agent, prophylactic or diagnostic agent. Thus, in some embodiments, the HLGAG preparation can further include a second agent other than the HLGAG, e.g., the preparation can further include one or more therapeutic, prophylactic or diagnostic agents. In another embodiment, the HLGAG preparation (e.g., the heparin or heparan sulfate preparation) has one or more of increased anti-Xa activity and anti-IIa activity, e.g., as compared to a reference standard, e.g., as compared to a commercially available heparin or heparan sulfate or as compared to the heparin or heparan sulfate preparation prior to contacting with a *B. thetaiotaomicron* GAG lyase polypeptide. Such preparation can be useful, e.g., for applications were increased anti-Xa activity and/or anti-IIa activity is desirable, e.g., as an anti-coagulant and/or anti-thrombotic agent.

In another aspect, the invention features a method of neutralizing one or more activities of an HLGAG (e.g., a heparin or heparan sulfate). The method includes contacting the HLGAG with a *B. thetaiotaomicron* GAG lyase polypeptide, *B. thetaiotaomicron* GAG lyase polypeptides or functional fragments thereof, e.g., a *B. thetaiotaomicron* GAG lyase I polypeptide, *B. thetaiotaomicron* GAG lyase III polypeptide, a *B. thetaiotaomicron* GAG lyase IV polypeptide and/or functional fragment thereof, described herein. When the HLGAG is heparin or heparan sulfate, the activity to be neutralized can be one or more of anti-Xa activity and anti-IIa activity. In some embodiments, anti-Xa activity is reduced while anti-IIa activity is maintained or increased. In other embodiments, anti-IIa activity is reduced while anti-Xa activity is maintained or enhanced. In other embodiments, anti-Xa activity and anti-IIa activity are reduced. In other embodiments, anti Xa and anti-IIa activities are maintained. The HLGAG can be, e.g., contacted ex vivo or in vivo. Thus, in some embodiments, the method can include administering the *B. thetaiotaomicron* GAG lyase polypeptide, *B. thetaiotaomicron* GAG lyase polypeptides or functional fragments thereof, to a subject in an amount effective to neutralize anti-Xa activity and/or anti-IIa activity in the subject, e.g., a subject that has been administered an HLGAG such as heparin or heparan sulfate, e.g., a subject that has been administered heparin or heparan sulfate to inhibit coagulation and/or thrombosis.

In another aspect, the invention features a method of inhibiting angiogenesis in a subject. The method includes administering to the subject an effect amount of a *B. thetaiotaomicron* GAG lyase polypeptide, *B. thetaiotaomicron* GAG lyase polypeptides, or functional fragments thereof, e.g., a *B. thetaiotaomicron* GAG lyase I polypeptide, a *B. thetaiotaomicron* GAG lyase II polypeptide, a *B. thetaiotaomicron* GAG lyase III polypeptide, a *B. thetaiotaomicron* GAG lyase IV polypeptide, or functional fragments thereof, described herein, to thereby inhibit angiogenesis. In one embodiment, the subject has a disease or disorder associated with unwanted angiogenesis. Such disorders include, but are not limited to, arthritis (e.g., rheumatoid arthritis), various eye disorders (e.g., diabetic retinopathy, neovascular glaucoma, inflammatory disorders, ocular tumors (e.g., retinoblastoma), retrolental fibroplasias, uveitis as well as disorders associated with choroidal neovascularization and iris neovascularization) and cancer (e.g., tumor growth and metastases).

In another aspect, the invention features a method of inhibiting unwanted cellular proliferation and/or differentiation in a subject. The method includes administering to the subject an effect amount of a *B. thetaiotaomicron* GAG lyase polypeptide, *B. thetaiotaomicron* GAG lyase polypeptides or functional fragment thereof, e.g., a *B. thetaiotaomicron* GAG lyase polypeptide, *B. thetaiotaomicron* GAG lyase polypeptides, or functional fragments thereof, described herein, to thereby inhibit cellular proliferation and/or differentiation. In one embodiment, the subject has cancer.

In another aspect, the invention features a pharmaceutical composition that includes a *B. thetaiotaomicron* GAG lyase polypeptide, *B. thetaiotaomicron* GAG lyase polypeptides, or functional fragments thereof, e.g., a *B. thetaiotaomicron* GAG lyase polypeptide, *B. thetaiotaomicron* GAG lyase polypeptides, or functional fragments thereof, described herein, and a pharmaceutically acceptable carrier. In one embodiment, the *B. thetaiotaomicron* GAG lyase polypeptide, *B. thetaiotaomicron* GAG lyase polypeptides, or functional fragments thereof, is present in an amount effective to neutralize one or more activity of an HLGAG. Preferably, the HLGAG is heparin or heparan sulfate and the *B. thetaiotaomicron* GAG lyase polypeptide, or functional fragment thereof, is present in an amount effective to neutralize one or more of anti-Xa activity and anti-IIa activity. In some embodiments, anti-Xa activity is reduced while anti-IIa activity is maintained or increased. In other embodiments, anti-IIa activity is reduced while anti-Xa activity is maintained or enhanced. In other embodiments, anti-Xa activity and anti-IIa activity is reduced. In another embodiment, the *B. thetaiotaomicron* GAG lyase polypeptide, or functional fragment thereof, is present in an amount effective to inhibit angiogenesis.

In another aspect, the invention features a kit comprising a composition of *B. thetaiotaomicron* GAG lyase polypeptide, *B. thetaiotaomicron* GAG lyase polypeptides, or functional fragments thereof. In one embodiment, the kit further includes one or more HLGAG degrading enzyme, e.g., one or more heparinase polypeptide and/or one or more GAG lyase polypeptide other than *B. thetaiotaomicron* GAG lyase polypeptide. For example, the kit can further comprise one or more of: an unsaturated glucuronyl hydrolase (e.g., *F. heparinum* Δ4,5 glycuronidase; *B. thetaiotaomicron* Δ4,5 glycuronidase); a glucuronyl hydrolase (e.g., mammalian α-iduronidase, β-glucuronidase); a sulfohydrolase (e.g., *F. heparinum* 2-O-sulfatase, 6-O-sulfatase, 3-O-sulfatase: *B. thetaiotaomicron* 6-O-sulfatase; mucin desulfating enzymes; mammalian N-acetylglucosamine-6-sulfatase; mammalian iduronic acid-2-sulfatase); a N-sulfamidase (e.g., *F. heparinum* N-sulfamidase; mammalian heparan-N-sulfatase); an arylsulfatase; a hexosaminidase; a glycosyl hydrolase (e.g., endo-N-acetyl glucosaminidase); a heparinase (e.g., *Flavobacterum heparinum* heparinase I, *Flavobacterum heparinum* heparinase II, *Flavobacterum heparinum* heparinase III, *Flavobacterum heparinum* heparinase IV aka heparinases from *Cytophaga heparina* or *Pedobacter heparinum*), mammalian heparanase, bacteriophage K5 heparan lyase, and functional fragments and variants thereof. In one embodiment, the *B. thetaiotaomicron* GAG lyase polypeptide, or functional fragment thereof, and one or more of the other HLGAG degrading enzymes are in the same composition. In another embodiment, the *B. thetaiotaomicron* GAG lyase polypeptide, or functional fragment thereof, and the other HLGAG degrading enzyme are in different compositions. In another embodiment, the *B. thetaiotaomicron* GAG lyase polypeptide, or functional fragment thereof, is in a pharmaceutical composition with a pharmaceutically effective carrier. The kits can further include an HLGAG, e.g., heparin and/or heparan sulfate. In one embodiment, when the kit includes a pharmaceutical composition of a *B. thetaiotaomicron* GAG lyase polypeptide, or functional fragment thereof, the HLGAG, e.g., heparin and/or heparan sulfate, is also in a pharmaceutical composition and, e.g., the kit further includes instructional material for neutralizing one or more activity of the HLGAG.

In another aspect, the invention features a nucleic acid molecule which encodes a *B. thetaiotaomicron* GAG lyase polypeptides, or functional fragments thereof. In one embodiment, the isolated nucleic acid molecule encodes a polypeptide having the amino acid sequence of SEQ ID NOs:2, 4, 6, 8, 10, 23, 29, 34, 37 or 39. In other embodiments, the invention provides isolated *B. thetaiotaomicron* GAG lyase nucleic acid molecules having the nucleotide sequence shown in SEQ ID NOs:1, 3, 5, 7, 9, 22, 28, 33, 36 or 38. In another embodiment, the invention provides nucleic acid molecules that are substantially identical to (e.g., naturally occurring allelic variants) to the nucleotide sequence shown in SEQ ID NOs:1, 5, 28, or 36 and nucleic acid molecules that hybridize under stringent hybridization conditions to a nucleic acid molecule comprising the nucleotide sequence of SEQ ID NOs:1, 3, 5, 7, 9, 22, 28, 33, 36 or 38, wherein the nucleic acid encodes a full length *B. thetaiotaomicron* GAG lyase protein, or functional fragments thereof.

In a related aspect, the invention further provides nucleic acid constructs which include a *B. thetaiotaomicron* GAG lyase nucleic acid molecule described herein. In certain embodiments, the nucleic acid molecules of the invention are operatively linked to native or heterogenous regulatory sequences. Also included are vectors and host cells containing the *B. thetaiotaomicron* GAG lyase nucleic acid molecules of the invention, e.g., vectors and host cells suitable for producing *B. thetaiotaomicron* GAG lyase nucleic acid molecules and polypeptides.

In another aspect, the invention features antibodies and antigen-binding fragments thereof, that react with, or more preferably, specifically bind *B. thetaiotaomicron* GAG lyase polypeptides.

In another aspect, the invention provides methods of screening for compounds that modulate the expression or activity of the *B. thetaiotaomicron* GAG lyase polypeptides or nucleic acids.

Other features and advantages of the invention will be apparent from the following detailed description, and from the claims.

BRIEF DESCRIPTION OF THE DRAWINGS

FIG. 1A depicts a DNA sequence (SEQ ID NO:1) encoding *B. thetaiotaomicron* GAG lyase I. Initiating methionione codon (ATG) is underlined and a second, internal methinione codon is doubled unlined FIG. 1B depicts its predicted amino acid sequence (SEQ ID NO:2) as well as indicating in bold the N-terminal amino acid residues of two variants of *B. thetaiotaomicron* GAG lyase I referred to as the M17 variant (SEQ ID NO:4) and the Q26 variant (SEQ ID NO:23).

FIG. 2 depicts a BLAST alignment of *B. thetaiotaomicron* GAG lyase I (SEQ ID NO:2) with a heparinase I from *Flavobacterium heparinum* (SEQ ID NO:24) and a consensus sequence (SEQ ID NO:26).

FIG. 3A depicts a DNA sequence (SEQ ID NO:3) encoding the M17 variant of *B. thetaiotaomicron* GAG lyase I with the ATG codon for methionine 17 (M17) shaded. FIG. 3B depicts its predicted amino acid sequence (SEQ ID NO:4).

FIG. 4A depicts a DNA sequence (SEQ ID NO:22) encoding the Q26 variant of *B. thetaiotaomicron* GAG lyase I. FIG. 4B depicts its predicted amino acid sequence (SEQ ID NO:23).

FIG. 5A depicts a DNA sequence (SEQ ID NO:5) encoding *B. thetaiotaomicron* GAG lyase II. FIG. 5A also depicts portions of the nucleotide sequence encoding *B. thetaiotaomicron* GAG lyase II that are not present in two variants of *B. thetaiotaomicron* GAG lyase II, namely the "Q23 variant" (SEQ ID NO:7) the deleted portion indicated by underlining, and the "K169 variant" (SEQ ID NO:9) the deleted portion indicated by shading. FIG. 5B depicts the predicted amino acid sequence *B. thetaiotaomicron* GAG lyase II (SEQ ID NO:6) as well as indicating the portions deleted from the amino acid sequence of the Q23 variant (SEQ ID NO:8) and the K169 variant (SEQ ID NO:10).

FIG. 6 depicts a BLAST alignment of *B. thetaiotaomicron* GAG lyase II (SEQ ID NO:6) with a heparinase III from *Flavobacterium heparinum* (SEQ ID NO:25) and a consensus sequence (SEQ ID NO:27).

FIG. 8 depicts a DNA sequence (SEQ ID NO:28) for coding sequence of GAG lyase III gene cloned from *Bacteroides thetaiotaomicron*. Initiating methionine (ATG) and stop (TAA) codons are noted in bold. Codon (CAG) corresponding to glutamine 23 (Q23) is underlined.

FIG. 9 depicts an amino acid sequence (SEQ ID NO:29) of GAG lyase III cloned from *Bacteroides thetaiotaomicron*. Predicted export signal sequence is underlined. Glutamine 23 (Q23) delimiting beginning of amino-terminal variant is shaded in gray.

FIG. 10 depicts alignment of amino acid sequence of *Bacteroides thetaiotaomicron* GAG lyase III (SEQ ID NO:29)—listed third from the top—with related heparin/heparan sulfate glycosaminoglycan lyases. Identical residues are shown in dark gray; similar residues are shown in light gray. BT represents *Bacteroides thetaiotaomicron*; FH represents *Flavobacterium heparinum*.

FIG. 13 depicts a DNA sequence (SEQ ID NO:36) encoding *B. thetaiotaomicron* GAG lyase IV. Initiating methionine codon (ATG) and stop codon are in bold and a second, codon (GAC) corresponding to aspartate 20 is unlined.

FIG. 14 depicts its predicted amino acid sequence (SEQ ID NO:37) with the signal sequence underlined. In addition, the N-terminal amino acid residues of the variant of *B. thetaiotaomicron* GAG lyase IV referred to as the D20 variant (SEQ ID NO:38) is shaded.

FIG. 15 depicts alignment of nucleic acid sequence of *Bacteroides thetaiotaomicron* GAG lyase IV (SEQ ID NO:36)—listed third from the top—with related heparin/heparan sulfate lyases. Identical residues are shown in dark gray; similar residues are shown in light gray. BT represents *Bacteroides thetaiotaomicron*; FH represents *Flavobacterium heparinum*.

DETAILED DESCRIPTION

Overview

Figure 7:
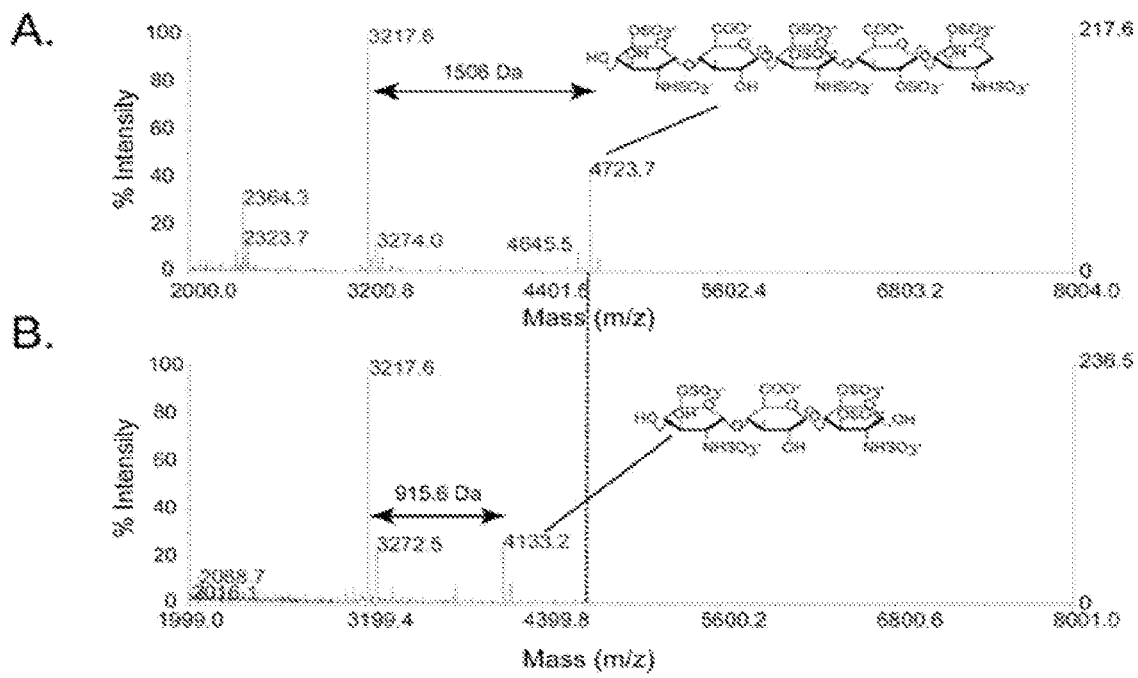
FIG. 7 is a representation of a MALDI-MS mass spectrum. Panel A depicts the peaks of untreated ATIII pentasaccharide ARIXTRA®, the structure of which is also shown. Panel B depicts the peaks produced after ARIXTRA® was digested with recombinant *B. thetaiotaomicron* GAG lyase I. A pentasulfated trisaccharide product, the structure of which is shown, results after digestion.

This disclosure describes recombinant expression of active *B. thetaiotaomicron* GAG lyases from *B. thetaiotaomicron*, that are useful, inter alia, in the modification and characterization of GAGs such as heparin and/or heparan sulfate glycosaminoglycans and derivatives thereof.

For example, the *B. thetaiotaomicron* GAG lyases described herein can be a complementary tool to existing chemo-enzymatic methods for cleaving GAGs such as heparin and heparan sulfate polysaccharides (and, in some cases, other GAGs such as chondroitin sulfate and dermatan sulfate) in a structure-specific fashion. Structure specific cleavage of a GAG, e.g., heparin and/or heparan sulfate, can be used, e.g., to determine the structure of GAGs in a heterogenous GAG preparation. In addition, cleavage can be used, e.g., to produce lower molecular weight oligosaccharides from the GAG. Thus, the *B. thetaiotaomicron* GAG lyases can be used to generate, e.g., heparin- and heparan sulfate-derived oligosaccharides. Such heparin- and heparan sulfate-derived oligosaccharides may have diagnostic, prophylactic and therapeutic potential.

In addition, the *B. thetaiotaomicron* GAG lyases described herein may also have prophylactic and therapeutic potential, e.g., in disorders associated with angiogenesis.

The *B. thetaiotaomicron* GAG lyases further can be used in vitro, ex vivo and/or in vivo to neutralize an anti-coagulant and/or anti-thrombotic activity of heparin and/or heparan sulfate.

The *B. thetaiotaomicron* GAG lyase I sequence (FIG. 1; SEQ ID NO:1), which is approximately 1251 nucleotides long including potentially untranslated regions, contains a predicted methionine-initiated coding sequence of about 1179 nucleotides, including the termination codon (nucleotides indicated as coding of SEQ ID NO:1 in FIG. 1). The putative coding sequence encodes a 392 amino acid protein (SEQ ID NO:2).

A variant in which the amino terminus begins at the methinione at residue 17 (M17) can also be used to produce recombinant protein. The amino acid sequence and nucleotide sequence encoding the M17 variant of *B. thetaiotaomicron* GAG lyase I are depicted in FIGS. 3B (SEQ ID NO:4) and 3A (SEQ ID NO:3), respectively. In addition, a 6× histidine fusion protein has been generated to facilitate purification. Inclusion of different purification tags such as GST, MBP, Trx, DsbC, NusA or biotin can also be used to obtain this enzyme.

Another variant in which the amino terminus begins at the glutamine at residue Q26 can also be used to produce recombinant protein. The amino acid sequence and nucleotide sequence encoding the Q26 variant of *B. thetaiotaomicron* GAG lyase I are depicted in FIGS. 4B (SEQ ID NO:23) and 4A (SEQ ID NO:22), respectively. In addition, a 6× histidine fusion protein has been generated to facilitate purification. Inclusion of different purification tags such as GST, MBP, Trx, DsbC, NusA or biotin can also be used to obtain this enzyme.

The *B. thetaiotaomicron* GAG lyase I protein shares structural characteristics with heparinase I obtained from *Flavobacterium heparinum*, at least at the primary amino acid sequence level (FIG. 2).

The *B. thetaiotaomicron* GAG lyase II gene sequence (FIG. 5; SEQ ID NO:5), which is approximately 2001 nucleotides long inclusive of the termination codon (nucleotides indicated as coding of SEQ ID NO:5 in FIG. 5A). The coding sequence encodes a 666 amino acid protein (SEQ ID NO:5B).

A variant in which the amino terminus begins at the glutamine at residue 23 (Q23) can also be used to produce recombinant protein. The amino acid sequence and nucleotide sequence encoding the Q23 variant of *B. thetaiotaomicron* GAG lyase II are depicted in FIG. 5B (SEQ ID NO:8) and 5A (SEQ ID NO:7), respectively. In addition, a 6× histidine fusion protein has been generated to facilitate purification. Inclusion of different purification tags such as GST, MBP, Trx, DsbC, NusA or biotin can also be used to obtain this enzyme.

Another variant in which is a deletion beginning at the lysine at residue 169 (K169) and ending at the glutamic acid at residue 186 can also be used to produce recombinant protein. The amino acid sequence and nucleotide sequence encoding the K169 variant of *B. thetaiotaomicron* GAG lyase II are depicted in FIGS. 5B (SEQ ID NO:10) and 5A (SEQ ID NO:9), respectively. The *B. thetaiotaomicron* GAG lyase II protein shares a number of structural characteristics with heparinase III obtained from *Flavobacterium heparinum*, at least at the level of their respective primary amino acid sequences.

The *B. thetaiotaomicron* GAG lyase III sequence (FIG. 8; SEQ ID NO:28), which is approximately 2690 nucleotides long (including untranslated sequence) and contains a predicted methionine-initiated coding sequence of about 2622 nucleotides, including the termination codon. The initiation and the termination codons are depicted in bold in FIG. 8. The coding sequence encodes an 873 amino acid protein (SEQ ID NO:29 in FIG. 9). A variant in which the amino terminus begins at the glutamine residue 23 (Q23) can also be used to produce recombinant protein. The nucleotide sequence of the variant is depicted in SEQ ID NO:33, while the amino acid sequence of the variant is shown in SEQ ID NO:34. Glutamine 23 residue is underlined in FIG. 9 and shaded in gray in FIG. 10. In addition, a 6× histidine fusion protein has been generated to facilitate purification. Inclusion of different purification tags such as GST, MBP, Trx, DsbC, NusA and biotin can also be used to obtain this enzyme.

The *B. thetaiotaomicron* GAG lyase III protein contains some structural characteristics and substrate specificity in common with heparinase II obtained from *Flavobacterium heparinum*. The *B. thetaiotaomicron* GAG lyase III protein has substrate specificity for both heparin and heparan sulfate. In addition, it is capable of cleaving chondroitin sulfate and dermatan sulfate.

The *B. thetaiotaomicron* GAG lyase IV sequence (FIG. 13; SEQ ID NO:36), which is approximately 2109 nucleotides long. The initiation and the termination codons are in bold in FIG. 15. The coding sequence encodes a 702 amino acid protein (SEQ ID NO:37 in FIG. 14).

A variant in which the amino terminus begins at the aspartate at amino acid residue 20 (D20) can also be used to produce recombinant protein. The nucleotide sequence of the variant is depicted in SEQ ID NO:38, while the amino acid sequence of the variant is shown in SEQ ID NO:39. The codon for aspartate 20 residue is underlined in FIG. 13 and aspartate 20 is shaded in gray in FIG. 14. In addition, a 6× histidine fusion protein has been generated to facilitate purification. Inclusion of different purification tags such as GST, MBP, Trx, DsbC, NusA or biotin can also be used to obtain this enzyme.

The *B. thetaiotaomicron* GAG lyase IV protein contains limited sequence similarity with other GAG lyases obtained from *B. thetaiotaomicron* or heparinases obtained from *Flavobacterium heparinum*. In addition, *B. thetaiotaomicron* GAG lyase IV protein has substrate specificity that varies from other GAG lyases obtained from *B. thetaiotaomicron* or heparinases obtained from *Flavobacterium heparinum*. For example, it can cleave di- or tetrasaccharides typically underrepresented in most naturally occurring heparin and/or heparan sulfates reported in the scientific literature.

As the *B. thetaiotaomicron* GAG lyase polypeptides of the invention may modulate heparin- and/or heparan sulfate-mediated activities, they may be useful in various prophylactic and therapeutic applications as well as for developing novel prophylactic and diagnostic agents for heparin- or heparan sulfate-mediated or related disorders.

As used herein, a "GAG lyase activity", "biological activity of GAG lyase" or "functional activity of GAG lyase", refers to an activity exerted by a *B. thetaiotaomicron* GAG lyase protein, polypeptide or nucleic acid molecule in a physiological milieu. For example, a GAG lyase activity can be an activity exerted by *B. thetaiotaomicron* GAG lyase on e.g., on a GAG lyase substrate, e.g., glycosidic linkages in heparin or heparan sulfate. A GAG lyase activity can be determined in vivo or in vitro.

The *B. thetaiotaomicron* GAG lyase molecules of the present invention are predicted to have similar biological activities to various heparinases obtained from *Flavobacterium heparinum*. For example, the *B. thetaiotaomicron* GAG lyase proteins of the present invention can have one or more of the following activities: (1) binds a heparin and/or a heparan sulfate; (2) cleaves one or more glycosidic linkages of a heparin and/or a heparan sulfate, e.g., in such a manner as to generate at the site of cleavage a uronic acid possessing an unsaturated bond between positions C4 and C5 (i.e., Δ4,5); (3) modulates, e.g., increases or reduces, anti-Xa activity and/or anti-IIa activity of a heparin and/or a heparan sulfate; and (4) reduces or eliminates angiogenesis.

In some aspects, the *B. thetaiotaomicron* GAG lyase I has biological activity similar to, but not identical with, heparinase I obtained from *Flavobacterium heparinum*. For example, the *B. thetaiotaomicron* GAG lyase I can have one or more of the following activities: (1) binds a heparin and/or heparan sulfate; (2) cleaves one or more glycosidic linkages of heparin and/or heparan sulfate, e.g., cleaves one or more glycosidic linkages involving sulfated uronic acids, e.g., 2-O uronic acids; cleaves one or more glycosidic linkages involving sulfated hexosamines, e.g., 6-O-sulfates and/or N-sulfamides; (3) reduces anti-Xa activity and/or anti-IIa activity of a heparin and/or a heparan sulfate, e.g., as compared to a reference standard, e.g., the anti-Xa activity and/or anti-IIa activity of a commercially available heparin or heparan sulfate or of the heparin or heparan sulfate prior to cleavage. In some embodiments, anti-Xa activity is reduced while anti-IIa activity is maintained. In other embodiments, anti-Xa activity and anti-IIa activity are reduced.

In some aspects, the *B. thetaiotaomicron* GAG lyase III has biological activity similar to, but not identical with, heparinase II obtained from *Flavobacterium heparinum*. For example, the *B. thetaiotaomicron* GAG lyase III can have one or more of the following activities: (1) binds a heparin, heparan sulfate, chondroitin sulfate and/or dermatin sulfate; (2) cleaves one or more glycosidic linkages of heparin and/or heparan sulfate, e.g., cleaves one or more glycosidic linkages of between a sulfated hexosamine (e.g., N-sulfated and/or 6-O sulfated) or an unsulfated, but acetylated hexosamine (e.g., HNAc) and a sulfated uronic acid, e.g., a 2-O sulfated uronic acid, or an unsulfated uronic acid; (3) decreases anti-Xa activity and/or anti-IIa activity of a heparin and/or a heparan sulfate, e.g., as compared to a reference standard, e.g., the anti-Xa activity and/or anti-IIa activity of a commercially available heparin or heparan sulfate or of the heparin or heparan sulfate prior to cleavage. In some embodiments, anti-Xa activity is reduced while anti-IIa activity is possibly maintained. In other embodiments, anti-Xa activity and anti-IIa activity are both reduced.

Thus, the *B. thetaiotaomicron* GAG lyase molecules, e.g., the *B. thetaiotaomicron* GAG lyase I and/or the *B. thetaiotaomicron* GAG lyase III molecules, can act as novel therapeutic agents for controlling heparin-associated disorders. Examples of such disorders include heparin-induced anticoagulation and/or angiogenesis. For example, the *B. thetaiotaomicron* GAG lyase molecules, e.g., the *B. thetaiotaomicron* GAG lyase I and/or the *B. thetaiotaomicron* GAG lyase III molecules, can be used to reduce or eliminate (e.g., neutralize) one or more anticoagulation properties of a heparin and/or a heparan sulfate, e.g., during or after surgery. In other embodiments, the *B. thetaiotaomicron* GAG lyase molecules, e.g., *B. thetaiotaomicron* GAG lyase I and/or the *B. thetaio-

*taomicron* GAG lyase III, can be used to deheparinize blood, e.g., in a bioreactor, e.g., a bioreactor used in heart-lung and/or kidney dialysis.

In some aspects, the *B. thetaiotaomicron* GAG lyase II has biological activity similar to, but not identical with, heparinase III obtained from *Flavobacterium heparinum*. For example, the *B. thetaiotaomicron* GAG lyase II can have one or more of the following activities: (1) binds a heparin and/or heparan sulfate; (2) cleaves one or more glycosidic linkages of heparin and/or heparan sulfate, e.g., cleaves one or more glycosidic linkages of sulfated and undersulfated uronic acids; (3) increases anti-Xa activity and/or anti-IIa activity of a heparin and/or a heparan sulfate, e.g., as compared to a reference standard, e.g., the anti-Xa activity and/or anti-IIa activity of a commercially available heparin or heparan sulfate or of the heparin or heparan sulfate prior to cleavage. In some embodiments, anti-Xa activity is maintained or possibly increased while anti-IIa activity is reduced. In other embodiments, anti-IIa activity is increased while anti-Xa activity is maintained.

In some aspects, the *B. thetaiotaomicron* GAG lyase IV has biological activity, e.g., substrate specificity, distinct from other known GAG lyases obtained from *B. thetaiotaomicron* and heparinases obtained from *Flavobacterium heparinum*. For example, the *B. thetaiotaomicron* GAG lyase IV can have one or more of the following activities: (1) binds a heparin and/or heparan sulfate; (2) cleaves one or more glycosidic linkages of heparin and/or heparan sulfate, e.g., cleaves one or more glycosidic linkages of low to medium sulfate density, especially linkages involving a 2-O-sulfated uronic acid and adjoining acetylated glucosamine (not commonly found in most naturally occurring preparations of heparin and/or heparan sulfate); (3) increases anti-Xa activity and/or anti-IIa activity of a heparin and/or a heparan sulfate, e.g., as compared to a reference standard, e.g., the anti-Xa activity and/or anti-IIa activity of a commercially available heparin or heparan sulfate or of the heparin or heparan sulfate prior to cleavage. In some embodiments, anti-Xa activity is increased while anti-IIa activity is maintained or reduced. In other embodiments, anti-IIa activity is increased while anti-Xa activity is maintained.

Thus, such *B. thetaiotaomicron* GAG lyase molecules, e.g., *B. thetaiotaomicron* GAG lyase II and *B. thetaiotaomicron* GAG lyase IV molecules, can be used to prepare a heparin and/or heparan sulfate preparation useful for treatment of coagulation and/or thrombosis. Examples of such disorders include dissolving or inhibiting formation of thromboses, treatment and prevention of conditions resulting from infarction of cardiac and central nervous system vessels, atherosclerosis, thrombosis, myocardial infarction, arrythmias, atrial fibrillation, angina, unstable angina, refractory angina, congestive heart failure, disseminated intravascular coagulation, percutaneous coronary intervention (PCI), coronary artery bypass graft surgery (CABG), reocclusion or restenosis of reperfused coronary arteries, rheumatic fever, stroke, transient ischemic attacks, thrombotic stroke, embolic stroke, deep venous thrombosis, pulmonary embolism, migraine, allergy, asthma, emphysema, adult respiratory stress syndrome (ARDS), cystic fibrosis, neovascularization of the ocular space, osteoporosis, psoriasis, arthritis (rheumatoid or osteogenic), Alzheimer's disease, bone fractures, major surgery/trauma, burns, surgical procedures, transplantation such as bone marrow transplantation, hip replacement, knee replacement, sepsis, septic shock, pregnancy, hereditary disorders such as hemophilias.

In other embodiments, the *B. thetaiotaomicron* GAG lyase molecules, e.g., *B. thetaiotaomicron* GAG lyase II and/or *B. thetaiotaomicron* GAG lyase IV molecules, can be used to treat or prevent cellular proliferative or differentiative disorders, e.g., by preventing or inhibiting angiogenesis of cells exhibiting or otherwise associated with unwanted proliferation and/or differentiation. Examples of cellular proliferative and/or differentiative disorders include diabetes; arthritis, e.g., rheumatoid arthritis; ocular disorders, e.g., ocular neovascularization, diabetic retinopathy, neovascular glaucoma, retrolental fibroplasia, uveitis, eye disease associated with choroidal neovascularization, eye disorders associated with iris neovascularization; cancer, e.g., carcinoma, sarcoma, metastatic disorders or hematopoietic neoplastic disorders, e.g., leukemias.

In other embodiments, the *B. thetaiotaomicron* GAG lyase molecules, e.g., *B. thetaiotaomicron* GAG lyase III molecules, can be used to prepare a chondroitin sulfate and/or dermatan sulfate preparation.

The *B. thetaiotaomicron* GAG lyase proteins, fragments thereof, and derivatives and other variants of the sequence in SEQ ID NO:2, SEQ ID NO:6, SEQ ID NO: 29 or SEQ ID NO:37 thereof are collectively referred to as "polypeptides or proteins of the invention" or "*B. thetaiotaomicron* GAG lyase polypeptides or proteins". Nucleic acid molecules encoding such polypeptides or proteins are collectively referred to as "nucleic acids of the invention" or "*B. thetaiotaomicron* GAG lyase nucleic acids." "*B. thetaiotaomicron* GAG lyase molecules" refer to *B. thetaiotaomicron* GAG lyase nucleic acids, polypeptides, and antibodies.

As used herein, the term "nucleic acid molecule" includes DNA molecules (e.g., a cDNA or genomic DNA), RNA molecules (e.g., an mRNA) and analogs of the DNA or RNA. A DNA or RNA analog can be synthesized from nucleotide analogs. A DNA molecule can be single-stranded or double-stranded, but preferably is double-stranded DNA.

The term "isolated nucleic acid molecule" or "purified nucleic acid molecule" includes nucleic acid molecules that are separated from other nucleic acid molecules present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under stringent conditions" describes conditions for hybridization and washing. Stringent hybridization conditions are hybridization in 6× sodium chloride/sodium citrate (SSC) at about 45° C., followed by two washes in 0.2×SSC, 0.1% SDS at 65° C. Hybridization conditions are known to those skilled in the art and can be found in Current Protocols in Molecular Biology, John Wiley & Sons, N.Y. (1989), 6.3.1-6.3.6. Aqueous and nonaqueous methods are described in that reference and either can be used. Additional examples of hybridization conditions are as follows: 1) low stringency, hybridization in 6×SSC at about 45° C., followed by one or more washes in 0.2×SSC, 0.1% SDS at 55° C.; 2) medium stringency, hybridization in 6×SSC at about 45° C., followed by one or more washes in 0.2×SSC, 0.1% SDS at 60° C.; and preferably, 3) high stringency, hybridization in 6×SSC at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M sodium phosphate, 7% SDS at 65° C., followed by one or more washes at 0.2×SSC, 1% SDS at 65° C. Preferably, an isolated nucleic acid molecule of the invention that hybridizes under stringent conditions to the sequence of SEQ ID NO:1, 5, 28 or 36 corresponds to a naturally-occurring nucleic acid molecule.

As used herein, a "naturally-occurring" nucleic acid molecule refers to an RNA or DNA molecule having a nucleotide sequence that occurs in nature. For example a naturally occurring nucleic acid molecule can encode a natural protein.

As used herein, the terms "gene" and "recombinant gene" refer to nucleic acid molecules which include at least an open reading frame encoding a B. thetaiotaomicron GAG lyase protein. The gene can optionally further include non-coding sequences, e.g., regulatory sequences and introns.

An "isolated" or "purified" polypeptide or protein is substantially free of cellular material or other contaminating proteins from the cell or tissue source from which the protein is derived, or substantially free from chemical precursors or other chemicals when chemically synthesized. "Substantially free" means that a preparation of B. thetaiotaomicron GAG lyase protein is at least 10% pure. In a preferred embodiment, the preparation of B. thetaiotaomicron GAG lyase protein has less than about 30%, 20%, 10% and more preferably 5% (by dry weight), of non-B. thetaiotaomicron GAG lyase protein (also referred to herein as a "contaminating protein"), or of chemical precursors or non-B. thetaiotaomicron GAG lyase chemicals. When the B. thetaiotaomicron GAG lyase protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of B. thetaiotaomicron GAG lyase without abolishing or substantially altering a GAG lyase activity. Preferably, the alteration does not substantially alter the GAG lyase activity, e.g., the activity is at least 20%, 40%, 60%, 70% or 80% of wild-type. An "essential" amino acid residue is a residue that, when altered from the wild-type sequence of B. thetaiotaomicron GAG lyase, results in abolishing a GAG lyase activity such that less than 20% of the wild-type activity is present. For example, conserved amino acid residues in B. thetaiotaomicron GAG lyase are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a B. thetaiotaomicron GAG lyase protein is preferably replaced with another amino acid residue from the same side chain family. Alternatively, in another embodiment, mutations can be introduced randomly along all or part of a B. thetaiotaomicron GAG lyase coding sequence, such as by saturation mutagenesis, and the resultant mutants can be screened for GAG lyase biological activity to identify mutants that retain activity. Following mutagenesis of SEQ ID NO:1, SEQ ID NO:5, SEQ ID NO:28, SEQ ID NO:36, the encoded protein can be expressed recombinantly and the activity of the protein can be determined.

As used herein, a "biologically active portion" of a B. thetaiotaomicron GAG lyase protein includes a fragment of a B. thetaiotaomicron GAG lyase protein which participates in an interaction, e.g., an inter-molecular interaction. An inter-molecular interaction can be a binding interaction or an enzymatic interaction (e.g., the interaction can be transient and a covalent bond is formed or broken). An inter-molecular interaction can be between a GAG lyase B. thetaiotaomicron molecule and a non-B. thetaiotaomicron GAG lyase molecule, e.g., heparin, heparan sulfate, and fragments thereof. Biologically active portions of a B. thetaiotaomicron GAG lyase protein include peptides comprising amino acid sequences sufficiently homologous to or derived from the amino acid sequence of the B. thetaiotaomicron GAG lyase protein, e.g., the amino acid sequence shown in SEQ ID NO:2, SEQ ID NO:6, SEQ ID NO:29 and SEQ ID NO:37, which include less amino acids than the full length B. thetaiotaomicron GAG lyase proteins, and exhibit at least one activity of a GAG lyase protein. Typically, biologically active portions comprise a domain or motif with at least one activity of the GAG lyase protein, e.g., depolymerization of heparin, heparan sulfate, and fragments thereof (e.g., in a site specific manor); cleavage of a glycosidic linkage of heparin, heparan sulfate, and fragments thereof; reduce or eliminate an anticoagulant activity, e.g., an anticoagulant activity of heparin, heparan sulfate, and fragments thereof. A biologically active portion of a B. thetaiotaomicron GAG lyase protein can be a polypeptide which is, for example, 10, 25, 50, 100, 200, 300, 400, 500 or more amino acids in length.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The percent identity between the two sequences is a function of the number of identical positions shared by the sequences, taking into account the number of gaps, and the length of each gap needed to be introduced for optimal alignment of the two sequences. For the purposes of determining if a molecule is within a sequence identity or a homology limitation herein, percent identity is determined by the mathematical algorithm of Needleman and Wunsch ((1970) *J. Mol. Biol.* 48:444-453) as implemented in the GAP program of the GCG software package (available at http://www.gcg.com) with the following parameters: a Blossum 62 scoring matrix with a gap penalty of 12, a gap extend penalty of 4, and a frameshift gap penalty of 5.

In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

For the purposes of analyzing a biological sequence with reference to *B. thetaiotaomicron* GAG lyase molecules, the following alignment procedures can be used in addition to the aforementioned Needleman and Wunsch algorithm. The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to *B. thetaiotaomicron* GAG lyase nucleic acid molecules of the invention. BLAST protein searches can be performed with the XBLAST program, score=50, wordlength=3 to obtain amino acid sequences homologous to *B. thetaiotaomicron* GAG lyase protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used. See http://www.ncbi.nlm.nih.gov.

Particular *B. thetaiotaomicron* GAG lyase polypeptides of the present invention have an amino acid sequence sufficiently identical to the amino acid sequence of SEQ ID Nos:2, 4, 6, 8, 10, 23, 29, 34, 37 or 39. In the context of an amino acid sequence, the term "sufficiently identical" or "substantially identical" is used herein to refer to a first amino acid that contains a sufficient or minimum number of amino acid residues that are i) identical to or ii) conservative substitutions of to aligned amino acid residues in a second amino acid sequence such that the first and second amino acid sequences have a common structural fold and/or a common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity are termed sufficiently or substantially identical. In the context of nucleotide sequence, the term "sufficiently identical" or "substantially identical" is used herein to refer to a first nucleic acid sequence that contains a sufficient or minimum number of nucleotides that are identical to aligned nucleotides in a second nucleic acid sequence such that the first and second nucleotide sequences have a common functional activity or encode a common structural polypeptide fold or a common functional polypeptide activity.

The methods taught herein are sometimes described with reference to heparin-like glycoaminoglycans (HLGAGs) but the properties taught herein can be extended to other polysaccharides. As used herein the terms "HLGAG" and "glycosaminoglycans" (GAGs) are used interchangeably to refer to a family of molecules having heparin like structures and properties, generally referred to herein as "heparin". These molecules include but are not limited to low molecular weight heparin (LMWH), unfractionated heparin, biotechnologically prepared heparin, chemically modified heparin, synthetic heparin such as pentasaccharides (e.g., ARIXTRA™), heparin mimetics and heparan sulfate. The term "biotechnological heparin" encompasses heparin that is prepared from natural sources of polysaccharides which have been chemically modified and is described in Razi et al., Bioche. J. 1995 Jul. 15; 309 (Pt 2): 465-72. Chemically modified heparin is described in Yates et al., Carbohydrate Res (1996) Nov. 20; 294:15-27, and is known to those of skill in the art. Synthetic heparin is well known to those of skill in the art and is described in Petitou, M. et al., Bioorg Med Chem. Lett. (1999) Apr. 19; 9(8):1161-6 and Vlodavsky et al., Int. J. Cancer, 1999, 83:424-431. An example of a synthetic heparin is fondaparinux. Fondaparinux (ARIXTRA™) is a 5 unit synthetic glycoaminoglycan corresponding to the AT-III binding site. Heparan Sulfate refers to a glycoaminoglycan containing a disaccharide repeat unit similar to heparin, but which has more N-acetyl groups and fewer N- and O-sulfate groups. Heparin mimetics are monosaccharides (e.g., sucralfate), oligosaccharides, or polysaccharides having at least one biological activity of heparin (i.e., anticoagulation, inhibition of cancer, treatment of lung disorders, etc.). Preferably these molecules are highly sulfated. Heparin mimetics may be naturally occurring, synthetic or chemically modified. (Barchi, J. J., Curr. Pharm. Des., 2000, Mar., 6(4):485-501). The term "HLGAG" also encompasses functional variants of the above-described HLGAG molecules. These functional variants have a similar structure but include slight modifications to the structure which allow the molecule to retain most of its biological activity or have increased biological activity.

"LMWH" as used herein refers to a preparation of sulfated glycosaminoglycans (GAGs) having an average molecular weight of less than 8000 Da, with about at least 60% of the oligosaccharide chains of a LMWH preparation having a molecular weight of less than 8000 Da. Several LMWH preparations are commercially available, but, LMWHs can also be prepared from heparin, using e.g., HLGAG degrading enzymes. HLGAG degrading enzymes include but are not limited to heparinase-I, heparinase-II, heparinase-III, heparinase IV, heparanase, D-glucuronidase and L-iduronidase. The three heparinases from *Flavobacterium heparinum* are enzymatic tools that have been used for the generation of LMWH (5,000-8,000 Da) and ultra-low molecular weight heparin (~3,000 Da). In addition, LMWHs can be prepared using, e.g., the *B. thetaiotaomicron* GAG lyase polypeptides described herein. Commercially available LMWH include, but are not limited to, enoxaparin (brand name Lovenox; Aventis Pharmaceuticals), dalteparin (Fragmin, Pharmacia and Upjohn), certoparin (Sandobarin, Novartis), ardeparin (Normiflo, Wyeth Lederle), nadroparin (Fraxiparine, Sanofi-Winthrop), parnaparin (Fluxum, Wassermann), reviparin (Clivarin, Knoll AG), and tinzaparin (Innohep, Leo Laboratories, Logiparin, Novo Nordisk). Some preferred forms of LMWH include enoxaparin (Lovenox) and dalteparin (Fragmin). The term "Arixtra" as used herein refers to a composition which includes a synthetic pentasaccharide of methyl O-2-deoxy-6-O-sulfo-2-(sulfoamino)-I-D-glucopyranosyl-(1→4)-O-θ-D-glucopyranosyl-(1→4)-O-2-deoxy-3,6-di-O-sulfo-2-(sulfoamino)-I-D-glucopyranosyl-(1→4)-O-2-O-sulfo-I-L-idopyranuronosyl-(1→4)-2-deoxy-6-O-sulfo-2-(sulfoamino)-I-D-glucopyranoside, decasodium salt and derivatives thereof. A "synthetic heparin" or "synthetic HLGAG" as used herein refers to HLGAGs are synthesized compounds and are not derived by fragmentation of heparin. Methods of preparing synthetic heparins are provided, for example, in Petitou et al. (1999) Nature 398:417, the contents of which is incorporated herein by reference.

"Misexpression or aberrant expression", as used herein, refers to a non-wildtype pattern of gene expression at the RNA or protein level. It includes: expression at non-wild type levels, i.e., over- or under-expression; a pattern of expression that differs from wild type in terms of the time or stage at which the gene is expressed, e.g., increased or decreased expression (as compared with wild type) at a predetermined developmental period or stage; a pattern of expression that differs from wild type in terms of altered expression (as compared with wild type) in a predetermined cell type or tissue type; a pattern of expression that differs from wild type in terms of the splicing size, translated amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, refers to a mammal organism. In a preferred embodiment, the subject is a human. In another embodiment, the subject is an experimental animal or animal suitable as a disease model. Non-limiting examples of such subjects include mice, rats, and rabbits. The subject can also be a non-human animal, e.g., a horse, cow, goat, or other domestic animal.

Various aspects of the invention are described in further detail below.

Isolated Nucleic Acid Molecules

In one aspect, the invention provides, an isolated or purified, nucleic acid molecule that encodes a B. thetaiotaomicron GAG lyase polypeptide described herein, e.g., a full length B. thetaiotaomicron GAG lyase protein or a fragment thereof, e.g., a biologically active portion of B. thetaiotaomicron GAG lyase protein. Also included is a nucleic acid fragment suitable for use as a hybridization probe, which can be used, e.g., to identify a nucleic acid molecule encoding a polypeptide of the invention, B. thetaiotaomicron GAG lyase mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, SEQ ID NO:5, SEQ ID NO:28 or SEQ ID NO:37 or a portion of any of these nucleotide sequences. In one embodiment, the nucleic acid molecule includes sequences encoding the B. thetaiotaomicron GAG lyase protein (i.e., "the coding region" of SEQ ID NO:1, SEQ ID NO:5, SEQ ID NO:28 or SEQ ID NO:36), as well as 5' untranslated sequences. Alternatively, the nucleic acid molecule can include no flanking sequences which normally accompany the subject sequence. In another embodiment, an isolated nucleic acid molecule of the invention includes a nucleic acid molecule which is a complement of the nucleotide sequence shown in SEQ ID NO:1, SEQ ID NO:5, SEQ ID NO:28 or SEQ ID NO:36, or a portion of any of these nucleotide sequences. In other embodiments, the nucleic acid molecule of the invention is sufficiently complementary to the nucleotide sequence shown in SEQ ID NO:1, SEQ ID NO:5, SEQ ID NO:28 or SEQ ID NO:36, such that it can hybridize to the nucleotide sequence shown in SEQ ID NO:1, SEQ ID NO:5, SEQ ID NO:28 or SEQ ID NO:36, thereby forming a stable duplex.

In one embodiment, an isolated nucleic acid molecule of the present invention includes a nucleotide sequence which is at least about 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:1, SEQ ID NO:5, SEQ ID NO:28 or SEQ ID NO:36, or a portion, preferably of the same length, of any of these nucleotide sequences.

A nucleic acid molecule of the invention can include only a portion of the nucleic acid sequence of SEQ ID NO:1, SEQ ID NO:5, SEQ ID NO:28, or SEQ ID NO:36. A nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein, particularly fragments thereof which are at least 100 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment encoding a "biologically active portion of a B. thetaiotaomicron GAG lyase polypeptide" can be prepared by isolating a portion of the nucleotide sequence of SEQ ID NO:1, 3, 5, 7, 9, 22, 28, 33, 36 or 38, which encodes a polypeptide having a GAG lyase biological activity (e.g., the biological activities of GAG lyase proteins are described herein), expressing the encoded portion of the B. thetaiotaomicron GAG lyase protein (e.g., by recombinant expression in vitro) and assessing the activity of the encoded portion of the B. thetaiotaomicron GAG lyase protein. A nucleic acid fragment encoding a biologically active portion of a B. thetaiotaomicron GAG lyase polypeptide, may comprise a nucleotide sequence which is greater than 300 or more nucleotides in length.

In preferred embodiments, a nucleic acid includes a nucleotide sequence which is about 300, 400, 500, 600, 700, 800, 900, 1000, 1100, 1200, 1300, 1400, 1500, 1600, 1700, 1800, 1900 or more nucleotides in length and hybridizes under stringent hybridization conditions to a nucleic acid molecule of SEQ ID NO:1, 3, 5, 7, 9, 22, 28, 33, 36 or 38.

The invention encompasses nucleic acid molecules that differ from the nucleotide sequence shown in SEQ ID NO:1, 3, 5, 7, 9, 22, 28, 33, 36 or 38. Such differences can be due to degeneracy of the genetic code (and result in a nucleic acid which encodes the same B. thetaiotaomicron GAG lyase proteins as those encoded by the nucleotide sequence disclosed herein). In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2, 4, 6, 8, 10, 23, 29, 34, 37 or 39. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one codon, at preferably at least 10%, or 20% of the codons has been altered such that the sequence is optimized for expression in E. coli, yeast, human, insect, or CHO cells.

Nucleic acid variants can be naturally occurring, such as allelic variants (same locus) and homologs (different locus), or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO: 1, 3, 5, 7, 9, 23, 28, 33, 36 or 38, e.g., as follows: by at least one but less than 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences.

Homologs and allelic variants can be identified using methods known in the art. These variants comprise a nucleotide sequence encoding a polypeptide that is 50%, at least about 55%, typically at least about 70-75%, more typically at least about 80-85%, and most typically at least about 90-95% or more identical to the amino acid sequence shown in SEQ ID NO:2, 4, 6, 8, 10, 23, 29, 34, 37 or 39, or a fragment of these sequences. Such nucleic acid molecules can readily be identified as being able to hybridize under stringent conditions, to the nucleotide sequence encoding the amino acid sequence shown in SEQ ID NO 2, SEQ ID NO:6, SEQ ID NO:29 or SEQ ID NO:37, or a fragment of the sequence. Nucleic acid molecules corresponding to homologs and allelic variants of the B. thetaiotaomicron GAG lyase DNAs of the invention can further be isolated by mapping to the same chromosome or locus as the B. thetaiotaomicron GAG lyase gene.

Preferred variants include those that are correlated with a GAG lyase activity described herein.

Allelic variants of B. thetaiotaomicron GAG lyase include both functional and non-functional proteins. Functional allelic variants are naturally occurring amino acid sequence variants of the B. thetaiotaomicron GAG lyase protein within a population that maintain one or more GAG lyase activity. Functional allelic variants will typically contain only conservative substitution of one or more amino acids of SEQ ID NO:2, 6, 29, or 37, or substitution, deletion or insertion of non-critical residues in non-critical regions of the protein. Examples of functional variants include the M17, Q26, Q23, K169 and D20 variants described herein (i.e., SEQ ID NOs: 4, 23, 8 10 and 39, respectively), as well as Q23 variant of GAG lyase III (SEQ ID NO:34). Non-functional allelic variants are naturally-occurring amino acid sequence variants of the B. thetaiotaomicron GAG lyase protein within a population that do not have one or more of the GAG lyase activities described herein. Non-functional allelic variants will typically contain a non-conservative substitution, a deletion, or insertion, or premature truncation of the amino acid sequence of SEQ ID NO:2, SEQ ID NO:6, SEQ ID NO:29 or SEQ ID NO:37, or a substitution, insertion, or deletion in critical residues or critical regions of the protein.

Moreover, nucleic acid molecules encoding other B. thetaiotaomicron GAG lyase family members and, thus, which have a nucleotide sequence which differs from the B. thetaiotaomicron GAG lyase sequences of SEQ ID NO:1, SEQ ID NO:5, SEQ ID NO:28 or SEQ ID NO:36 are intended to be within the scope of the invention.

Isolated B. thetaiotaomicron GAG Lyase Polypeptides

In another aspect, the invention features isolated B. thetaiotaomicron GAG lyase proteins, and fragments thereof, e.g., biologically active portions thereof. B. thetaiotaomicron GAG lyase protein can be isolated from cells or tissue sources using standard protein purification techniques. B. thetaiotaomicron GAG lyase protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present when expressed in a native cell.

In a preferred embodiment, a B. thetaiotaomicron GAG lyase polypeptide has one or more of the following characteristics: (1) binds a heparin and/or a heparan sulfate; (2) cleaves one or more glycosidic linkages of a heparin and/or a heparan sulfate; (3) modulates, e.g., increases or reduces, anti-Xa activity and/or anti-IIa activity of a heparin and/or a heparan sulfate; and (4) reduces or eliminates angiogenesis.

In some embodiments, the B. thetaiotaomicron GAG lyase is B. thetaiotaomicron GAG lyase I and the B. thetaiotaomicron GAG lyase I can have one or more of the following activities: (1) binds a heparin and/or heparan sulfate; (2) cleaves one or more glycosidic linkages of heparin and/or heparan sulfate, e.g., cleaves one or more glycosidic linkages of sulfated uronic acids, e.g., 2-O uronic acids; cleaves one or more glycosylic linkages involving sulfated hexosamines, e.g., 6-O sulfates and/or N-sulfamides; (3) reduces anti-Xa activity and/or anti-IIa activity of a heparin and/or a heparan sulfate, e.g., as compared to a reference standard, e.g., the anti-Xa activity and/or anti-IIa activity of a commercially available heparin or heparan sulfate or of the heparin or heparan sulfate prior to cleavage. In some embodiments, anti-Xa activity is reduced while anti-IIa activity is maintained. In other embodiments, anti-Xa activity and anti-IIa activity are reduced.

In some embodiments, the B. thetaiotaomicron GAG lyase is B. thetaiotaomicron GAG lyase II and the B. thetaiotaomicron GAG lyase II can have one or more of the following activities: (1) binds a heparin and/or heparan sulfate; (2) cleaves one or more glycosidic linkages of heparin and/or heparan sulfate, e.g., cleaves one or more glycosidic linkages of sulfated and undersulfated uronic acids; (3) increases anti-Xa activity and/or anti-IIa activity of a heparin and/or a heparan sulfate, e.g., as compared to a reference standard, e.g., the anti-Xa activity and/or anti-IIa activity of a commercially available heparin or heparan sulfate or of the heparin or heparan sulfate prior to cleavage. In some embodiments, anti-Xa activity is maintained or increased while anti-IIa activity is reduced. In other embodiments, anti-IIa activity is increased while anti-Xa activity is maintained.

In some embodiments, the B. thetaiotaomicron GAG lyase is B. thetaiotaomicron GAG lyase III and the B. thetaiotaomicron GAG lyase III can have one or more of the following activities: (1) binds a heparin, heparan sulfate, chondroitin sulfate and/or dermatin sulfate; (2) cleaves one or more glycosidic linkages of heparin and/or heparan sulfate, e.g., cleaves one or more glycosidic linkages of between a sulfated hexosamine (e.g., N-sulfated and/or 6-O sulfated) or an unsulfated, but acetylated hexosamine (e.g., HNAc) and a sulfated uronic acid, e.g., a 2-O sulfated uronic acid, or an unsulfated uronic acid; (3) decreases anti-Xa activity and/or anti-IIa activity of a heparin and/or a heparan sulfate, e.g., as compared to a reference standard, e.g., the anti-Xa activity and/or anti-IIa activity of a commercially available heparin or heparan sulfate or of the heparin or heparan sulfate prior to cleavage. In some embodiments, anti-Xa activity is reduced while anti-IIa activity is maintained. In other embodiments, anti-Xa activity and anti-IIa activity are reduced.

In some embodiments, the *B. thetaiotaomicron* GAG lyase is *B. thetaiotaomicron* GAG lyase IV and the *B. thetaiotaomicron* GAG lyase IV can have one or more of the following activities: (1) binds a heparin and/or heparan sulfate; (2) cleaves one or more glycosidic linkages of heparin and/or heparan sulfate, e.g., cleaves one or more glycosidic linkages of low to medium sulfate density, especially linkages involving a 2-O sulfated uronic acid and adjoining acetylated glucosamine (not commonly found in most naturally occurring preparations of heparin and/or heparin sulfate); (3) increases anti-Xa activity and/or anti-IIa activity of a heparin and/or a heparan sulfate, e.g., as compared to a reference standard, e.g., the anti-Xa activity and/or anti-IIa activity of a commercially available heparin or heparan sulfate or of the heparin or heparan sulfate prior to cleavage. In some embodiments, anti-Xa activity is increased while anti-IIa activity is maintained or reduced. In other embodiments, anti-IIa activity is increased while anti-Xa activity is maintained In a preferred embodiment, the *B. thetaiotaomicron* GAG lyase protein, or fragment thereof, differs from the corresponding sequence in SEQ ID NO:2, 4, 6, 8, 10, 23, 29, 34, 37 or 39. In one embodiment, it differs by at least one but by less than 15, 10 or 5 amino acid residues. In another, it differs from the corresponding sequence in SEQ ID NO:2, 4, 6, 8, 10, 23, 29, 34, 37 or 39 by at least one residue but less than 20%, 15%, 10% or 5% of the residues in it differ from the corresponding sequence in SEQ ID NO:2, 4, 6, 8, 10, 23, 29, 34, 37 or 39. (If this comparison requires alignment the sequences should be aligned for maximum homology. "Looped" out sequences from deletions or insertions, or mismatches, are considered differences.) The differences are, preferably, differences or changes at a non essential residue or a conservative substitution.

Other embodiments include a protein that contain one or more changes in amino acid sequence, e.g., a change in an amino acid residue which is not essential for activity. Such *B. thetaiotaomicron* GAG lyase proteins differ in amino acid sequence from SEQ ID NO:2, 4, 6, 8, 10, 23, 29, 34, 37 or 39, yet retain biological activity.

In one embodiment, the protein includes an amino acid sequence at least about 50%, 55%, 60%, 65%, 70%, 75%, 80%, 85%, 90%, 95%, 98% or more homologous to SEQ ID NO:2, 4, 6, 8, 10, 23, 29, 34, 37 or 39.

Biologically active portions, in which regions of the protein are deleted, can be prepared by recombinant techniques and evaluated for one or more of the functional activities of a native *B. thetaiotaomicron* GAG lyase protein.

In a preferred embodiment, the *B. thetaiotaomicron* GAG lyase protein has an amino acid sequence shown in SEQ ID NOs:2, 4, 6, 8, 10, 23, 29, 34, 37 or 39. In other embodiments, the *B. thetaiotaomicron* GAG lyase protein is substantially identical to SEQ ID NOs:2, 4, 6, 8, 10, 23, 29, 34, 37 or 39. In yet another embodiment, the *B. thetaiotaomicron* GAG lyase protein is substantially identical to SEQ ID NOs:2, 4, 6, 8, 10, 23, 29, 34, 37 or 39 and retains the functional activity of the protein of SEQ ID NO:2, 4, 6, 8, 10, 23, 29, 34, 37 or 39, as described in detail in the subsections above.

In another aspect, the invention provides *B. thetaiotaomicron* GAG lyase chimeric or fusion proteins. As used herein, a *B. thetaiotaomicron* GAG lyase "chimeric protein" or "fusion protein" includes a *B. thetaiotaomicron* GAG lyase polypeptide linked to a non-*B. thetaiotaomicron* GAG lyase polypeptide. A "non-*B. thetaiotaomicron* GAG lyase polypeptide" refers to a polypeptide having an amino acid sequence corresponding to a protein which is not substantially homologous to the *B. thetaiotaomicron* GAG lyase protein, e.g., a protein which is different from the *B. thetaiotaomicron* GAG lyase protein and which is derived from the same or a different organism. The *B. thetaiotaomicron* GAG lyase polypeptide of the fusion protein can correspond to all or a portion e.g., a fragment described herein, of a *B. thetaiotaomicron* GAG lyase amino acid sequence. In a preferred embodiment, a *B. thetaiotaomicron* GAG lyase fusion protein includes at least one (or two) biologically active portion of a *B. thetaiotaomicron* GAG lyase protein. The non-*B. thetaiotaomicron* GAG lyase polypeptide can be fused to the N-terminus or C-terminus of the *B. thetaiotaomicron* GAG lyase polypeptide.

The fusion protein can include a moiety which has a high affinity for a ligand. For example, the fusion protein can be a GST-*B. thetaiotaomicron* GAG lyase fusion protein in which the *B. thetaiotaomicron* GAG lyase sequences are fused to the C-terminus of the GST sequences. Such fusion proteins can facilitate the purification of recombinant *B. thetaiotaomicron* GAG lyase. Alternatively, the fusion protein can be a *B. thetaiotaomicron* GAG lyase protein containing a heterologous signal sequence at its N-terminus. In certain host cells (e.g., mammalian host cells), expression and/or secretion of *B. thetaiotaomicron* GAG lyase can be increased through use of a heterologous signal sequence. Moreover, the *B. thetaiotaomicron* GAG lyase-fusion proteins of the invention can be used as immunogens to produce anti-*B. thetaiotaomicron* GAG lyase antibodies in a subject, to purify *B. thetaiotaomicron* GAG lyase ligands and in screening assays to identify molecules which inhibit the interaction of *B. thetaiotaomicron* GAG lyase with a *B. thetaiotaomicron* GAG lyase substrate.

Expression vectors are commercially available that already encode a fusion moiety (e.g., a GST polypeptide). A *B. thetaiotaomicron* GAG lyase-encoding nucleic acid can be cloned into such an expression vector such that the fusion moiety is linked in-frame to the *B. thetaiotaomicron* GAG lyase protein.

In another aspect, the invention also features a variant of a *B. thetaiotaomicron* GAG lyase polypeptide, e.g., which functions as an agonist (mimetics). Variants of the *B. thetaiotaomicron* GAG lyase proteins can be generated by mutagenesis, e.g., discrete point mutation, the insertion or deletion of sequences or the truncation of a *B. thetaiotaomicron* GAG lyase protein. An agonist of the *B. thetaiotaomicron* GAG lyase proteins can retain substantially the same, or a subset, of the biological activities of the naturally occurring form of a *B. thetaiotaomicron* GAG lyase protein.

Variants of a *B. thetaiotaomicron* GAG lyase protein can be identified by screening combinatorial libraries of mutants, e.g., truncation mutants, of a *B. thetaiotaomicron* GAG lyase protein for agonist activity. Variants of a *B. thetaiotaomicron* GAG lyase I include the M17 variant as shown in SEQ ID NO:4 and the Q26 variant as shown in SEQ ID NO:23. Variants of a *B. thetaiotaomicron* GAG lyase II include the Q23 variant as shown in SEQ ID NO:8 and the K169 variant as shown in SEQ ID NO:10. Variants of *B. thetaiotaomicron* GAG lyase III include the Q23 variant shown in SEQ ID:34. Variants of *B. thetaiotaomicron* GAG lyase III include the D20 variant shown in SEQ ID:39.

Libraries of fragments e.g., N terminal, C terminal, or internal fragments, of a *B. thetaiotaomicron* GAG lyase protein coding sequence can be used to generate a variegated population of fragments for screening and subsequent selection of variants of a *B. thetaiotaomicron* GAG lyase protein. Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of *B. thetaiotaomicron* GAG lyase proteins. Recursive ensemble mutagenesis (REM), a new technique which enhances the frequency of functional mutants in the libraries, can be used in combination with the screening assays to identify *B. thetaiotaomicron* GAG lyase variants (Arkin and Yourvan (1992) *Proc. Natl. Acad. Sci. USA* 89:7811-7815; Delgrave et al. (1993) *Protein Engineering* 6:327-331).

Cell based assays can be exploited to analyze a variegated *B. thetaiotaomicron* GAG lyase library. For example, a library of expression vectors can be transfected into a cell line, e.g., a cell line, which ordinarily responds to *B. thetaiotaomicron* GAG lyase in a substrate-dependent manner The transfected cells are then contacted with *B. thetaiotaomicron* GAG lyase and the effect of the expression of the mutant on the activity of the *B. thetaiotaomicron* GAG lyase substrate can be detected, e.g., by measuring cleavage of heparin or heparan sulfate. Plasmid DNA can then be recovered from the cells which score for inhibition, or alternatively, potentiation of signaling by the *B. thetaiotaomicron* GAG lyase substrate, and the individual clones further characterized.

In another aspect, the invention features a method of making a fragment or analog of a naturally occurring *B. thetaiotaomicron* GAG lyase polypeptide. The method includes: altering the sequence, e.g., by substitution or deletion of one or more residues, of a *B. thetaiotaomicron* GAG lyase polypeptide, e.g., altering the sequence of a non-conserved region, or a domain or residue described herein, and testing the altered polypeptide for the desired activity, e.g., as described above.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a *B. thetaiotaomicron* GAG lyase nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., *B. thetaiotaomicron* GAG lyase proteins, mutant forms of *B. thetaiotaomicron* GAG lyase proteins, fusion proteins, and the like).

The recombinant expression vectors of the invention can be designed for expression of *B. thetaiotaomicron* GAG lyase proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in *B. thetaiotaomicron* GAG lyase activity assays, (e.g., direct assays or competitive assays described in detail below), or to generate antibodies specific for *B. thetaiotaomicron* GAG lyase proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

The *B. thetaiotaomicron* GAG lyase expression vector can be a yeast expression vector, a vector for expression in insect cells, e.g., a baculovirus expression vector or a vector suitable for expression in mammalian cells.

When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard (1992) *Proc. Natl. Acad. Sci. USA* 89:5547, and Paillard (1989) *Human Gene Therapy* 9:983).

In still another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., a *B. thetaiotaomicron* GAG lyase nucleic acid molecule within a recombinant expression vector or a *B. thetaiotaomicron* GAG lyase nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a *B. thetaiotaomicron* GAG lyase protein can be expressed in bacterial cells (such as *E. coli*), insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a *B. thetaiotaomicron* GAG lyase protein. Accordingly, the invention further provides methods for producing a *B. thetaiotaomicron* GAG lyase protein using the host cells of the invention. In one embodiment, the method includes culturing the host cell of the invention (into which a recombinant expression vector encoding a *B. thetaiotaomicron* GAG lyase protein has been introduced) in a suitable medium such that a *B. thetaiotaomicron* GAG lyase protein is produced. In another embodiment, the method further includes isolating a *B. thetaiotaomicron* GAG lyase protein from the medium or the host cell.

In another aspect, the invention features, a cell or purified preparation of cells which include a *B. thetaiotaomicron* GAG lyase transgene, or which otherwise misexpress *B. thetaiotaomicron* GAG lyase. The cell preparation can consist of human or non-human cells, e.g., rodent cells, e.g., mouse or rat cells, rabbit cells, or pig cells. In preferred embodiments, the cell or cells include a *B. thetaiotaomicron* GAG lyase transgene, e.g., a heterologous form of a *B. thetaiotaomicron* GAG lyase, e.g., a gene derived from humans (in the case of a non-human cell). The *B. thetaiotaomicron* GAG lyase transgene can be misexpressed, e.g., overexpressed or underexpressed. In other preferred embodiments, the cell or cells include a gene that mis-expresses an endogenous *B. thetaiotaomicron* GAG lyase, e.g., a gene the expression of which is disrupted, e.g., a knockout. Such cells can serve as a model for studying disorders that are related to mutated or mis-expressed *B. thetaiotaomicron* GAG lyase alleles or for use in drug screening.

In another aspect, the invention features, a human cell, e.g., a hematopoietic stem cell, transformed with nucleic acid which encodes a subject *B. thetaiotaomicron* GAG lyase polypeptide.

Also provided are cells in which a *B. thetaiotaomicron* GAG lyase is under the control of a regulatory sequence that does not normally control the expression of the endogenous *B. thetaiotaomicron* GAG lyase gene. The expression characteristics of an endogenous gene within a cell, e.g., a cell line or microorganism, can be modified by inserting a heterologous DNA regulatory element into the genome of the cell such that the inserted regulatory element is operably linked to the endogenous *B. thetaiotaomicron* GAG lyase gene. For example, an endogenous *B. thetaiotaomicron* GAG lyase gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

Uses

As described herein, the *B. thetaiotaomicron* GAG lyase molecules of the invention are useful in many applications including, but not limited to: 1) characterization of GAGs such as heparins and heparan sulfates (and, to some extent, chondroitin sulfate and dermatan sulfate) in terms of chemical composition (di-, tri-, tetra-, penta-, hexa-, octa-, and/or deca-oligosaccharides); 2) characterization of a pharmaceutical formulation of GAGs such as a formulation of heparin or a heparan sulfate (and, to some extent, chondroitin sulfate and dermatan sulfate); 3) fractionation of a GAG such as a heparin and a heparan sulfate (and, to some extent, chondroitin sulfate and dermatan sulfate) into both its chemical constituents as well as into smaller fragments of defined length, sequence, and potential bioactivities; 4) in vitro neutralization of the anticoagulant activity (anti-Xa) of a heparin or a heparan sulfate; 5) in vitro modulation of antithrombotic activity (anti IIa); 6) identification of the presence and purity of a particular GAG such as a heparin or a heparan sulfate in a sample; 7) determination of the composition of a GAG in a sample; 8) determination of the sequence of di-, tetra-, hexa-, octa- and deca-saccharide units in a particular heparin or heparan sulfate; 9) use as an additional analytic tool for chemical analysis using techniques such as mass spectrometry, NMR spectroscopy, gel electrophoresis, capillary electrophoresis, HPLC, and ion-pair HPLC; 10) for cleaving a particular GAG such as a heparin or heparan sulfate that comprises at least two disaccharide units; 11) for inhibiting angiogenesis, e.g., through administration to a subject in need thereof an effective amount of a composition (e.g., a pharmaceutical composition) containing *B. thetaiotaomicron* GAG lyase molecules; 12) for treating cancer through the administration to a subject a composition (e.g., a pharmaceutical composition) containing *B. thetaiotaomicron* GAG lyase molecules; 13) inhibiting cellular proliferation through the administration to a subject in need thereof an effective amount of a composition (e.g., a pharmaceutical composition) containing *B. thetaiotaomicron* GAG lyase molecules for inhibiting cellular proliferation; 14) for ex vivo neutralization of the anti-Xa activity of a preparation (e.g., a pharmaceutical preparation) of a heparin or a heparan sulfate previously administered to a subject for the inhibition of coagulation; 15) for in vivo neutralization of the anti-Xa activity of preparation (e.g., a pharmaceutical preparation) of a heparin or a heparan sulfate through administration to a subject in need of such neutralization (e.g., a subject to whom a pharmaceutical preparation of a heparin or a heparan sulfate had previously been administered); 16) for ex vivo neutralization of the anti-IIa activity of a preparation (e.g., pharmaceutical preparation) of a heparin or heparan sulfate previously administered to a subject for the inhibition of thrombosis; or 17) for in vivo neutralization of the anti-IIa activity of preparation (e.g., a pharmaceutical preparation) of a heparin or a heparan sulfate through administration to a subject in need in need of such neutralization (e.g., a subject to whom a pharmaceutical preparation of a heparin or heparan sulfate had previously been administered).

Characterization and Sequencing of GAGs

Methods described herein can be used, e.g., for analyzing polysaccharides such as GAGs, (e.g., a mixed population of polysaccharides), e.g., to define the structural signature and/or activity of a polysaccharides (e.g., a mixed population of polysaccharides), by contacting the polysaccharide with a *B. thetaiotaomicron* GAG lyase molecule. A structural signature, as used herein, refers to information regarding, e.g., the identity and number the mono- and di-saccharide building blocks of a polysaccharide, information regarding the physiochemical properties such as the overall charge (also referred to as the "net charge" or "total charge"), charge density, molecular size, charge to mass ratio and the presence of iduronic and/or glucuronic acid content as well as the relationships between the mono- and di-saccharide building blocks, and active sites associated with these building blocks, inter alia. The structural signature can be provided by determining one or more primary outputs that include the following: the presence or the amount of one or more component saccharides or disaccharides; as used herein, "component saccharides" refers to the saccharides that make up the polysaccharide. Component saccharides can include monosaccharides, disaccharides, trisaccharides, etc., and can also include sugars normally found in nature as well as non-natural and modified sugars, e.g., that result due to production, processing and/or purification; the presence or the amount of one or more block components, wherein a "block component" is made up of more than one saccharide or polysaccharide; and the presence or amount of one or more modified saccharides, wherein a modified saccharide is one present in a starting material used to make a preparation but which is altered in the production of the preparation, e.g., a saccharide modified by cleavage. "Sequence" with respect to polysaccharides refers to the linear arrangement of covalently linked component saccharides, and can be determined by methods known in the art, e.g., the methods disclosed herein and in PCT Publication Nos: WO 00/65521, WO 02/23190, and WO 04/055491; U.S. Publication Nos: 20030191587 and 20040197933; Venkataraman (1999); Shriver et al. (2000a); Shriver et al. (2000b); and Keiser et al. (2001); the entire teachings of which are incorporated herein by reference. "Positioning of the active site" refers to a correlation between a certain component polysaccharide and a given activity.

In one embodiment, the invention provides, methods of evaluating a polysaccharide mixture, e.g., a heterogeneous population of HLGAGs, by evaluating one or more parameters related to a structural signature species described herein. Such parameters can include the presence, size distribution, or quantity of a structural signature disclosed herein. The structural signature can be one or more of the following:

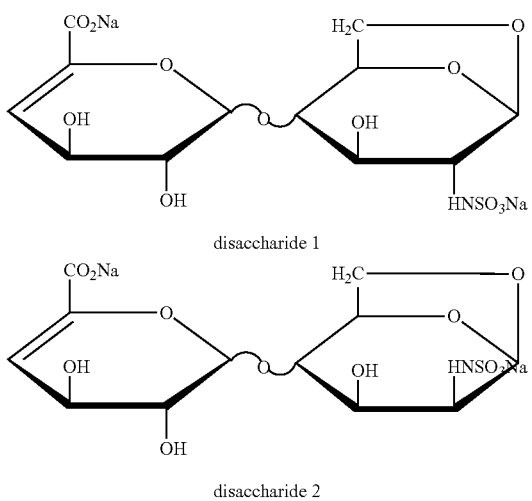

disaccharide 1 disaccharide 2

-continued
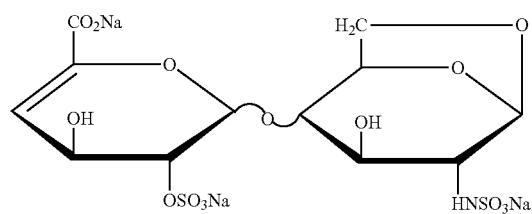
disaccharide 3
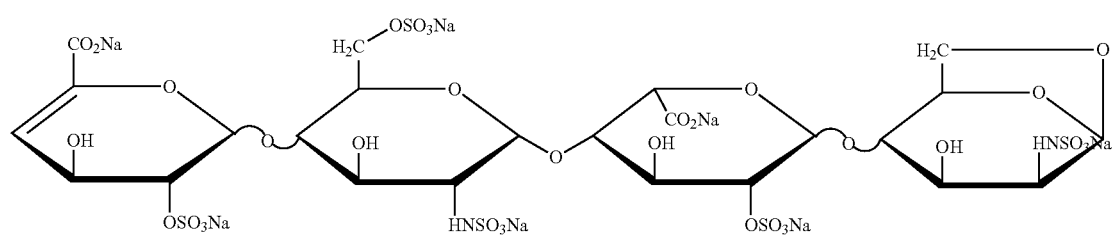
tetrasaccharide 1
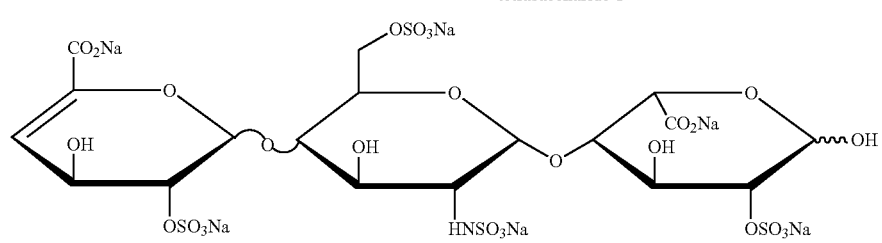
trisaccharide 1
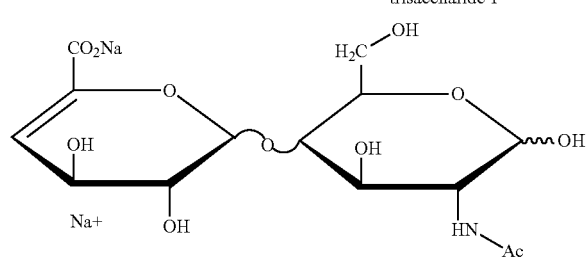
ΔIVa
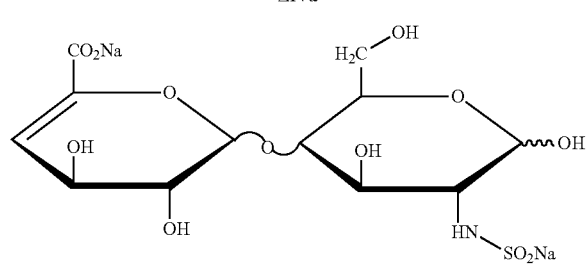
ΔIVs
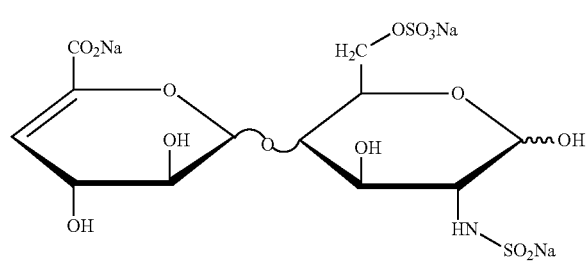
ΔIIs_gal

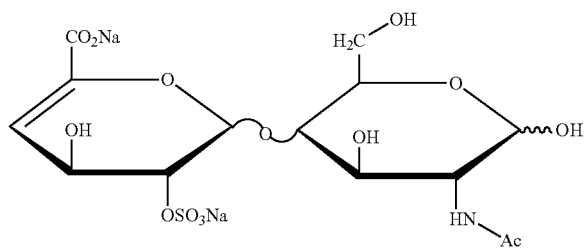
ΔIIIa
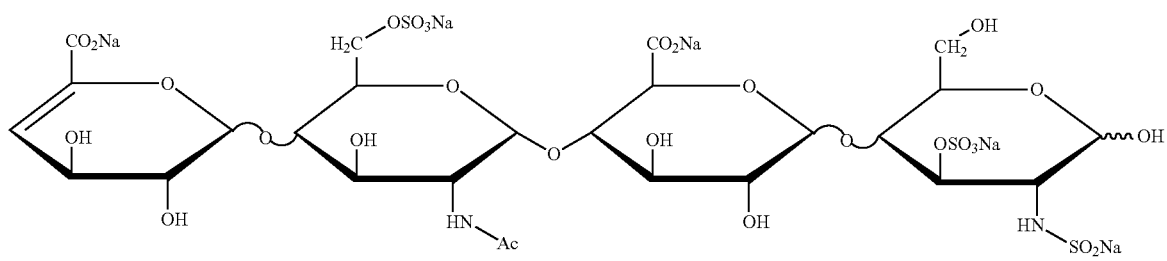
Δ UA-GlcNAc-GlcA-GlcNS(3S) or Δ IIa-IVs$_{glu}$
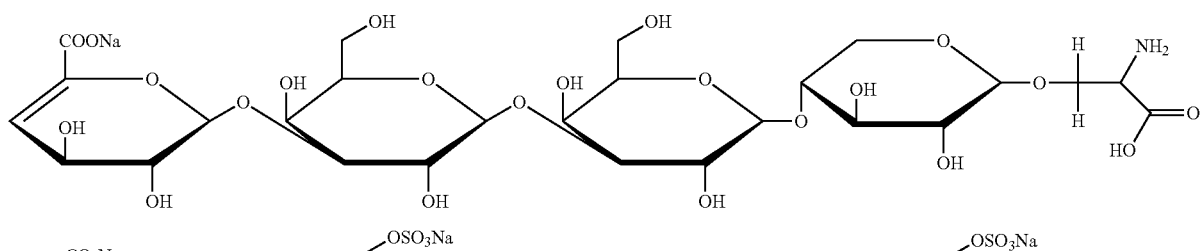
Δ UA-GlcNAc-GlcA-GlcNS(3,6S) or Δ IIa-IIs$_{glu}$
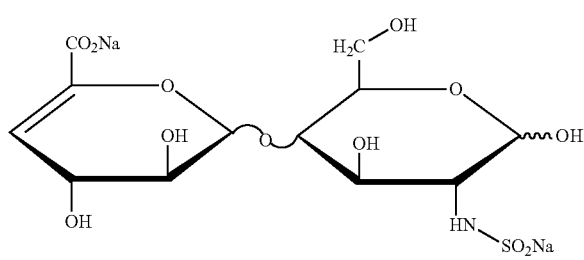
ΔIVs$_{gal}$
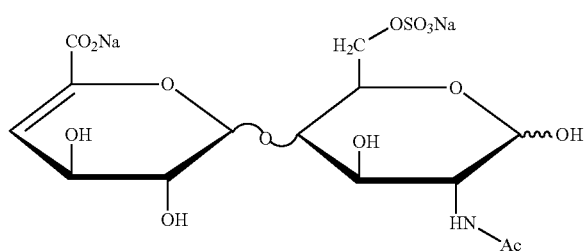
ΔIIa

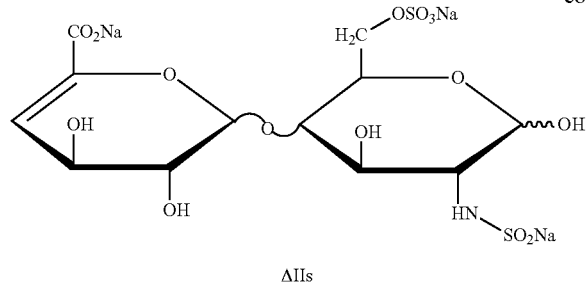

ΔIIs

In a preferred embodiment, the structural signature is determined by one or more methods chosen from the group consisting of MALDI-MS, ESI-MS, CE, HPLC, FPLC, fluorometry, ELISA, chromogenic assays such as reverse phase column chromatography (e.g., HPLC), colorimetric assays, NMR and other spectroscopic techniques.

The polysaccharide composition is digested, incompletely or completely digested, with one or more *B. thetaiotaomicron* GAG lyase molecule. The composition can further be digested with one or more HLGAG degrading enzyme. Examples of other HLGAG degrading enzymes include: heparinase I, heparinase II, heparinase III, heparinase IV, heparanase, D-glucuronidase, L-iduronidase and functionally active variants and fragments thereof. Various HLGAG degrading enzymes, and variants and fragments thereof, are known and described, e.g., in U.S. Pat. Nos. 5,569,600; 5,389,539; 5,830,726; 5,714,376; 5,919,693; 5,681,733 and 6,869,789; and U.S. Patent Publications Nos: 20030099628; 20030303301; and 20010565375, the contents of which are incorporated herein by reference.

The methods described herein can further include: providing or determining a first structural signature by contacting a batch of a polysaccharide (e.g., a heterogenous population of polysaccharides) with a *B. thetaiotaomicron* GAG lyase molecule or molecules; providing or determining a second structural signature of a different batch of a polysaccharide (e.g., a heterogenous population of polysaccharides) by contacting the batch with a *B. thetaiotaomicron* GAG lyase molecule or molecules; and comparing the first and second structural determinations to determine if one or more of the batches has a structural determination associated with a particular property. The methods can further include selecting or discarding a batch of the polysaccharide depending on its structural determination.

In other embodiments, a batch of a polysaccharide (e.g., a heterogenous population of polysaccharides) can be analyzed by comparing one or more structural signature of the polysaccharide obtained by contacting the polysaccharide with one or more *B. thetaiotaomicron* GAG lyase molecules to a reference standard. The reference standard can be, e.g., a preselected range or level and/or the absence or presence of a structural signature present in a mixed population of polysaccharides, e.g., a commercially available population of polysaccharides such as enoxaparin (Lovenox™); dalteparin (Fragmin™); certoparin (Sandobarin™); ardeparin (Normiflo™); nadroparin (Fraxiparin™); parnaparin (Fluxum™); reviparin (Clivarin™); tinzaparin (Innohep™ or Logiparin™), or Fondaparinux (Arixtra™) that has been digested with the *B. thetaiotaomicron* GAG lyase molecule or molecules.

The *B. thetaiotaomicron* GAG lyase molecules can also be used to determine a reference standard for a drug by analyzing a composition contacted with a *B. thetaiotaomicron* GAG lyase molecule or molecules and determining the bioequivalence and/or bioavailability of one or more of the components in the mixture. As used herein, "bioequivalence" means "the absence of a significant difference in the rate and extent to which an active ingredient or active moiety in pharmaceutical equivalents or pharmaceutical alternatives becomes available at the site of drug action when administered at the same molar dose under similar conditions."

Production of Fractionated HLGAG Preparations

The *B. thetaiotaomicron* GAG lyase molecules described herein can be used to produce polysaccharides (e.g., fractionated heparin or heparan sulfate), e.g., having desired properties, e.g., desired activities and/or reduced undesired properties, e.g., undesired side effects. As used herein, "desired activities" refers to those activities that are beneficial for a given indication, e.g., a positive patient reaction as defined herein, inter alia. An "undesirable activity" may include those activities that are not beneficial for a given indication, e.g., a negative patient reaction, as defined herein, inter alia. A given activity may be a desired activity for one indication, and an undesired activity for another, such as anti-IIa activity, which while undesirable for certain indications, is desirable in others, notably acute or trauma situations. Thus, the invention relates to methods for designing heparins, LMWHs or synthetic heparins with ideal product profiles including, but not limited to such features as high activity, e.g., high anti-Xa and/or anti-IIa activity, reduced activity, e.g., reduced anti-Xa and/or anti-IIa activity, well characterized, neutralizable, lower side effects including reduced HIT, attractive pharmacokinetics, and/or reduced PF4 binding.

Fractionated heparins can be designed, e.g., by contacting composition that includes a mixed population of polysaccharides, such as glycosaminoglycans (GAGs), HLGAGs, UFH, FH, LMWHs, or synthetic heparins including but not limited to enoxaparin (Lovenox™); dalteparin (Fragmin™); certoparin (Sandobarin™); ardeparin (Normiflo™); nadroparin (Fraxiparin™); parnaparin (Fluxum™); reviparin (Clivarin™); tinzaparin (Innohep™ or Logiparin™), or Fondaparinux (Arixtra™) with a *B. thetaiotaomicron* GAG lyase.

In some embodiments, a fractionated heparin preparation having reduced anti-Xa and/or anti-IIa activity is prepared by contacting a heparin with a *B. thetaiotaomicron* GAG lyase I and/or *B. thetaiotaomicron* GAG lyase III molecule. In some embodiments, anti-Xa activity is reduced while anti-IIa activity is maintained In other embodiments, anti-Xa activity and anti-IIa activity are reduced. Heparins having reduced anti-Xa and/or anti-IIa activity can be used, e.g., as a carrier to deliver an agent, e.g., a diagnostic, prophylactic or therapeutic agent. The heparin molecule can be linked to the agent. Active agents can include a therapeutic or prophylactic polypeptide, nucleic acid, small molecule, lipid/glycolipids, etc. In one embodiment, the active agent is a therapeutic polypeptide selected from the group consisting of insulin, proinsulin, human growth hormone, interferon, α-1 proteinase inhibitor, alkaline phosphotase, angiogenin, cystic fibrosis transmembrane conductance regulator, extracellular superoxide dismutase, fibrinogen, glucocerebrosidase, glutamate decarboxylase, human serum albumin, myelin basic protein, soluble CD4, lactoferrin, lactoglobulin, lysozyme, lactoalbumin, erythropoietin, tissue plasminogen activator, antithrombin III, prolactin, and α1-antitrypsin. The therapeutic or prophylactic polypeptide can be an active derivative or fragment of such polypeptides. The active agent can also be, but is not limited to one or more of: parathyroid hormone and derivatives and fragments thereof, erythropoietin, epoetin beta, gene activated erythropoietin, second generation EPO, novel erythropoiesis stimulating protein, insulin lispro, insulin (bovine), insulin, insulin aspart, insulin analogue, Calcitonin, Theraccine, becaplermin (recombinant human platelet derived growth factor-BB), trafermin, human growth hormone-releasing factor, BMP-7, PEG asparaginase, dornase alpha, alglucerase, agalsidase-beta, dornase alpha, agalsidase-alfa, streptokinase, teneteplase, reteplase, alteplase, pamiteplase, Rh factor VIII, Rh FVIIa, Factor IX (Human), Factor IX (complex), HGH, Somatrem/somatropin, anti-CD33-calicheamicin conjugate, Edrecolomab, rituxumab, daclizumab, trastuzumab, sulesomab, abciximab, infliximab, muromonab-CD3, palivizumab, alemtuzumab, basiliximab, oprelvekin, gemtuzamab ozogamicin, ibritumomab tiuxetan, sulesomab, palivizumab, interleukin-2, celmoleukin (rIL-2), interferon alfacon-1, interferon alpha, interferon alpha+ribavirin, peg interferon alpha-2a, interferon alpha-2b, interferon alpha 3n, interferon beta-1a, interferon beta, interferon beta 1b, interferon gamma, interferon gamma-1b, filgrastim, sargramostim, lenograstim, molgramostim, mirimostim, nartograstim, oprelvekin, peptide tyrosin-tyrosin (PYY), apolipoprotein A-IV, leptin, melanocortin, amylin, orexin, adiponectin, and ghrelin. In one embodiment, the active agent is an active polypeptide, e.g., a therapeutic or prophylactic polypeptide, and the polypeptide has a molecular weight of less than 150 kDa, more preferably less than 100 kDa, and more preferably less than 50 kDa. In one embodiment, the active agent is an active polypeptide, e.g., a therapeutic or prophylactic polypeptide, and the polypeptide has a molecular weight of about 500Da-5 kDa, 5 to 10 kDa, 10 to 30 kDa, 18 to 35 kDa, 30 to 50 kDa, 50 to 100 kDa, 100 to 150 kDa. In one embodiment, the active polypeptide is insulin or an active fragments or derivatives thereof. In another embodiment, the active polypeptide is human growth hormone or an active fragment or derivative thereof. In yet another embodiment, the active polypeptide is interferon. In other embodiments, the heparin molecule is linked to an inactive agent. Examples of inactive agents include biological probes or contrast agents for imaging. In another embodiment, the active agent can be a small molecule drug, e.g., a small molecule drug currently available for therapeutic, diagnostic, or prophylactic use, or a drug in development. In some embodiments, the active agent is linked to one or more heparin molecules in the formulation. As an example, small molecule drugs, and protein-based drugs may be linked to heparin molecule for delivery via known chemistries such as EDC, $CNBH_4$/DMSO/Acetic Acid, etc.

The invention also relates to fractionated heparin preparations having increased anti-Xa and/or anti-IIa activity prepared by contacting a heparin with a *B. thetaiotaomicron* GAG lyase II and/or *B. thetaiotaomicron* GAG lyase IV molecule. Such preparation can be used, e.g., to treat or prevent a disease associated with coagulation, such as thrombosis, cardiovascular disease, vascular conditions or atrial fibrillation; migraine, atherosclerosis; an inflammatory disorder, such as autoimmune disease or atopic disorders; obesity or excess adipose, an allergy; a respiratory disorder, such as asthma, emphysema, adult respiratory distress syndrome (ARDS), cystic fibrosis, or lung reperfusion injury; a cancer or metastatic disorder, e.g., lipomas; diabetes; an angiogenic disorder, such as neovascular disorders of the eye, osteoporosis, psoriasis, arthritis, Alzheimer's, a subject to undergo, undergoing or having undergone surgical procedure, organ transplant, orthopedic surgery, treatment for a fracture, e.g., a hip fracture, hip replacement, knee replacement, percutaneous coronary intervention (PCI), stent placement, angioplasty, coronary artery bypass graft surgery (CABG).

Pharmaceutical Compositions

The *B. thetaiotaomicron* GAG lyase molecules, as well as heparin molecules prepared by cleavage with the *B. thetaiotaomicron* GAG lyase molecules can be incorporated into pharmaceutical compositions. Such compositions typically include a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Alternatively, the pharmaceutical composition can be used to treat a sample (e.g., blood in a bioreactor, e.g., to deheparinize blood) before the sample is introduced into a subject.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The skilled artisan will appreciate that certain factors may influence the dosage and timing required to effectively treat a subject, including but not limited to the severity of the disease or disorder, previous treatments, the general health and/or age of the subject, and other diseases present.

The pharmaceutical compositions can be included in a container, pack, or dispenser together with instructions for administration.

Therapeutic Applications

The *B. thetaiotaomicron* GAG lyase molecules can act as novel diagnostic and therapeutic agents for controlling one or more of cellular proliferative and/or differentiative disorders, e.g., by preventing or inhibiting angiogenesis of cells otherwise exhibiting or otherwise associated with unwanted proliferation and/or differentiation. Examples of cellular and/or differentiative disorders include: diabetes; arthritis, e.g., rheumatoid arthritis; ocular disorders, e.g., ocular neovascularization, diabetic retinopathy, neovascular glaucoma, retinal fibroplasias, uveitis, eye disorders associated with iris neovascularization; and cancer, e.g., carcinoma, sarcoma, metastatic disorders or hematopoietic neoplastic disorders, e.g., leukemias.

As used herein, the terms "cancer", "hyperproliferative" and "neoplastic" refer to cells having the capacity for autonomous growth. Examples of such cells include cells having an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Additional examples of proliferative disorders include hematopoietic neoplastic disorders. As used herein, the term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), pro-lymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease. The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

In another embodiment, the *B. thetaiotaomicron* GAG lyase molecules, e.g., the *B. thetaiotaomicron* GAG lyase I and/or the *B. thetaiotaomicron* GAG lyase III molecules, can act as prophylactic or therapeutic agents for controlling heparin-associated disorders. Examples of such disorders include, but are not limited to, heparin-induced anticoagulation and/or angiogenesis. Thus, the *B. thetaiotaomicron* GAG lyase molecules, e.g., the *B. thetaiotaomicron* GAG lyase I and/or the *B. thetaiotaomicron* GAG lyase III molecules, can be used to reduce or eliminate (e.g., neutralize) one or more anticoagulation and/or antithrombotic properties of heparin and/or heparan sulfate, e.g., during or after surgery. In other embodiments, the *B. thetaiotaomicron* GAG lyase molecules, e.g., the *B. thetaiotaomicron* GAG lyase I and/or the *B. thetaiotaomicron* GAG lyase III molecules, can be used to deheparinized blood, e.g., in a bioreactor, e.g., a bioreactor used in heart-lung and/or kidney dialysis.

The *B. thetaiotaomicron* GAG lyase molecules described herein can also be used to design fractionated GAG preparations, e.g., heparin and/or heparan sulfate preparations. Such fractionated HLGAG preparations may have many therapeutic utilities. For instance, it is known that HLGAG compositions are useful for preventing and treating dementia, such as Alzheimer's disease, coagulation, angiogenesis, thrombotic disorders, cardiovascular disease, vascular conditions, atherosclerosis, respiratory disorders, circulatory shock and related disorders, as well as inhibiting cancer cell growth and metastasis. Each of these disorders is well-known in the art and is described, for instance, in *Harrison's Principles of Internal Medicine* (McGraw Hill, Inc., New York), which is incorporated by reference. The use of HLGAG compositions in various therapeutic methods is described and summarized in Huang, J. and Shimamura, A., Coagulation Disorders, 12, 1251-1281 (1998).

The fractionated HLGAG preparations can be used, e.g., to treat or prevent a disorder where increased presence of active FGF, e.g., aFGF and/or bFGF, is desirable.

The HLGAG preparations are useful for treating or preventing disorders associated with coagulation. When an imbalance in the coagulation pathway shifts towards excessive coagulation, the result is the development of thrombotic tendencies, which are often manifested as heart attacks, strokes, deep venous thrombosis, acute coronary syndromes (ACS) such as unstable angina, and myocardial infarcts. A "disease associated with coagulation" as used herein refers to a condition characterized by local inflammation which can result from an interruption or reduction in the blood supply to a tissue which may occur, for instance, as a result of blockage of a blood vessel responsible for supplying blood to the tissue such as is seen for myocardial or cerebral infarction or peripheral vascular disease, or as a result of emboli formation associated with conditions such as atrial fibrillation or deep venous thrombosis. Coagulation disorders include, but are not limited to, cardiovascular disease and vascular conditions such as cerebral ischemia. It is particularly useful to treat disorders such as myocardial infarction and ACS with, e.g., a polysaccharide by pulmonary delivery because of the fast absorption and action of this delivery system.

The fractionated HLGAG preparations are useful for treating cardiovascular disease. Cardiovascular diseases include, but are not limited to, acute myocardial infarction, ACS, e.g., unstable angina, and atrial fibrillation. Myocardial infarction is a disease state which sometimes occurs with an abrupt decrease in coronary blood flow that follows a thrombotic occlusion of a coronary artery previously narrowed by atherosclerosis. Such injury may be produced or facilitated by factors such as cigarette smoking, hypertension, and lipid accumulation. Acute angina is due to transient myocardial ischemia. This disorder is usually associated with a heaviness, pressure, squeezing, smothering, or choking feeling below the sternum. Episodes are usually caused by exertion or emotion, but can occur at rest.

Atrial fibrillation is a common form of arrhythmia generally arising as a result of emotional stress or following surgery, exercise, or acute alcoholic intoxication. Persistent forms of atrial fibrillation generally occur in patients with cardiovascular disease. Atrial fibrillation is characterized by disorganized atrial activity without discrete P waves on the surface ECG. This disorganized activity can lead to improper blood flow in the atrium and thrombus formation. These thrombi can embolize, resulting in cerebral ischemia and other disorders.

Persons undergoing surgery, anesthesia and extended periods of bed rest or other inactivity are often susceptible to a condition known as deep venous thrombosis, or DVT, which is a clotting of venous blood in the lower extremities and/or pelvis. This clotting occurs due to the absence of muscular activity in the lower extremities required to pump the venous blood (stasis), local vascular injury or a hypercoaguble state. The condition can be life-threatening if a blood clot migrates to the lung, resulting in a "pulmonary embolus" or otherwise interferes with cardiovascular circulation. One method of treatment involves administration of an anti-coagulant.

The fractionated HLGAG preparations can be used for the treatment of cardiovascular disorders alone or in combination with other therapeutic agents for reducing the risk of a cardiovascular disease or for treating the cardiovascular disease. Other therapeutic agents include, but are not limited to, anti-inflammatory agents, anti-thrombotic agents, anti-platelet agents, fibrinolytic agents, lipid reducing agents, direct thrombin inhibitors, anti-Xa inhibitors, anti-IIa inhibitors, glycoprotein IIb/IIIa receptor inhibitors and direct thrombin inhibitors such as hirudin, hirugen, Angiomax, agatroban, PPACK, thrombin aptamers.

The HLGAG preparations are also useful for treating vascular conditions. Vascular conditions include, but are not limited to, disorders such as deep venous thrombosis, peripheral vascular disease, cerebral ischemia, including stroke, and pulmonary embolism. A cerebral ischemic attack or cerebral ischemia is a form of ischemic condition in which the blood supply to the brain is blocked. This interruption or reduction in the blood supply to the brain may result from a variety of causes, including an intrinsic blockage or occlusion of the blood vessel itself, a remotely originated source of occlusion, decreased perfusion pressure or increased blood viscosity resulting in inadequate cerebral blood flow, or a ruptured blood vessel in the subarachnoid space or intracerebral tissue.

The HLGAG preparations are useful for treating cerebral ischemia. Cerebral ischemia may result in either transient or permanent deficits and the seriousness of the neurological damage in a patient who has experienced cerebral ischemia depends on the intensity and duration of the ischemic event. A transient ischemic attack is one in which the blood flow to the brain is interrupted only briefly and causes temporary neurological deficits, which often are clear in less than 24 hours. Symptoms of TIA include numbness or weakness of face or limbs, loss of the ability to speak clearly and/or to understand the speech of others, a loss of vision or dimness of vision, and a feeling of dizziness. Permanent cerebral ischemic attacks, also called stroke, are caused by a longer interruption or reduction in blood flow to the brain resulting from either a thrombus or embolism. A stroke causes a loss of neurons typically resulting in a neurologic deficit that may improve but that does not entirely resolve.

Thromboembolic stroke is due to the occlusion of an extracranial or intracranial blood vessel by a thrombus or embolus. Because it is often difficult to discern whether a stroke is caused by a thrombosis or an embolism, the term "thromboembolism" is used to cover strokes caused by either of these mechanisms.

The rapid absorption of HLGAGs, such as UFH or LMWH, after inhalation can be very valuable in the treatment of venous thromboembolism. Intravenous administration of UFH has been used widely for treatment of venous thromboembolism in combination with oral warfarin. Due to the improved efficacy and reduced risks, however, LMWHs have been increasingly used as an alternative to intravenous UFH in treatment of venous thromboembolism. It has been established that efficacy of heparin therapy depends on achieving critical therapeutic levels (e.g., of values of anti-factor Xa or anti-factor IIa activity) within the first 24 hours of treatment. Intrapulmonary delivery of heparin particles to achieve rapid therapeutic levels of heparin in the early stage of thromboembolism, could also be combined with other routes of administration of LMWHs or heparin for prolonged antithrombotic/ anticoagulant effect such as oral administration.

The HLGAG preparations can also be used to treat acute thromboembolic stroke. An acute stroke is a medical syndrome involving neurological injury resulting from an ischemic event, which is an interruption or reduction in the blood supply to the brain.

An effective amount of a HLGAG preparation alone or in combination with another therapeutic for the treatment of stroke is that amount sufficient to reduce in vivo brain injury resulting from the stroke. A reduction of brain injury is any prevention of injury to the brain which otherwise would have occurred in a subject experiencing a thromboembolic stroke absent the treatment described herein. Several physiological parameters may be used to assess reduction of brain injury, including smaller infarct size, improved regional cerebral blood flow, and decreased intracranial pressure, for example, as compared to pretreatment patient parameters, untreated stroke patients or stroke patients treated with thrombolytic agents alone.

The pharmaceutical HLGAG preparation may be used alone or in combination with a therapeutic agent for treating a disease associated with coagulation. Examples of therapeutics useful in the treatment of diseases associated with coagulation include anticoagulation agents, antiplatelet agents, and thrombolytic agents.

Anticoagulation agents prevent the coagulation of blood components and thus prevent clot formation. Anticoagulants include, but are not limited to, warfarin, Coumadin, dicumarol, phenprocoumon, acenocoumarol, ethyl biscoumacetate, and indandione derivatives. "Direct thrombin inhibitors" include hirudin, hirugen, Angiomax, agatroban, PPACK, thrombin aptamers. Antiplatelet agents inhibit platelet aggregation and are often used to prevent thromboembolic stroke in patients who have experienced a transient ischemic attack or stroke. Thrombolytic agents lyse clots which cause the thromboembolic stroke. Thrombolytic agents have been used in the treatment of acute venous thromboembolism and pulmonary emboli and are well known in the art (e.g. see Hennekens et al, *J Am Coll Cardiol*; v. 25 (7 supp), p. 18S-22S (1995); Holmes, et al, *J Am Coll Cardiol*; v. 25 (7 suppl), p. 10S-17S(1995)).

Pulmonary embolism as used herein refers to a disorder associated with the entrapment of a blood clot in the lumen of a pulmonary artery, causing severe respiratory dysfunction. Pulmonary emboli often originate in the veins of the lower extremities where clots form in the deep leg veins and then travel to lungs via the venous circulation. Thus, pulmonary embolism often arises as a complication of deep venous thrombosis in the lower extremity veins. Symptoms of pulmonary embolism include acute onset of shortness of breath, chest pain (worse with breathing), and rapid heart rate and respiratory rate. Some individuals may experience haemoptysis.

The HLGAG preparations and methods are also useful for treating or preventing atherosclerosis. Heparin has been shown to be beneficial in prevention of atherosclerosis in various experimental models. Due to the more direct access to the endothelium of the vascular system, inhaled heparin can be useful in prevention of atherosclerosis. Atherosclerosis is one form of arteriosclerosis that is believed to be the cause of most coronary artery disease, aortic aneurysm and atrial disease of the lower extremities, as well as contributing to cerebrovascular disease.

Due to its fast absorption and variable elimination rate, HLGAG with or without excipients can be used as an alternative for the intravenous heparin for surgical and dialysis procedures. For example, HLGAG particles can be inhaled prior to surgery by volunteer inhalation or passively inhaled via trachea tube during the anesthesia prior to or during the surgery. Surgical patients, especially those over the age of 40 years have an increased risk of developing deep venous thrombosis. Thus, the use of HLGAG particles for preventing the development of thrombosis associated with surgical procedures is contemplated. In addition to general surgical procedures such as percutaneous intervention (e.g., percutaneous coronary intervention (PCI)), PCTA, stents and other similar approaches, hip or knee replacement, cardiac-pulmonary by-pass surgery, coronary revascularization surgery, orthopedic surgery, and prosthesis replacement surgery, the methods are also useful in subjects undergoing a tissue or organ transplantation procedure or treatment for fractures such as hip fractures.

In addition, pulmonary inhalation of heparin is valuable in treatment of respiratory diseases such as cystic fibrosis, asthma, allergy, emphysema, adult respiratory distress syndrome (ARDS), lung reperfusion injury, and ischemia-reperfusion injury of the lung, kidney, heart, and gut, and lung tumor growth and metastasis.

Cystic fibrosis is a chronic progressive disease affecting the respiratory system. One serious consequence of cystic fibrosis is *Pseudomonas aeruginosa* lung infection, which by itself accounts for almost 90% of the morbidity and mortality in cystic fibrosis. Therapeutics for treating cystic fibrosis include antimicrobials for treating the pathogenic infection.

Heparin is also a well established inhibitor of elastase and tumor growth and metastasis. The aerosolized heparin particles are capable of inhibiting elastase induced lung injury in an acute lung emphysema model. Asthma is a disorder of the respiratory system characterized by inflammation, narrowing of the airways and increased reactivity of the airways to inhaled agents. Asthma is frequently, although not exclusively, associated with atopic or allergic symptoms. Asthma may also include exercise induced asthma, bronchoconstrictive response to bronchostimulants, delayed-type hypersensitivity, auto immune encephalomyelitis and related disorders. Allergies are generally caused by IgE antibody generation against allergens. Emphysema is a distention of the air spaces distal to the terminal bronchiole with destruction of alveolar septa. Emphysema arises out of elastase induced lung injury. Heparin is capable of inhibiting this elastase induced injury. Adult respiratory distress syndrome is a term which encompasses many acute defuse infiltrative lung lesions of diverse ideologies which are accompanied by severe atrial hypoxemia. One of the most frequent causes of ARDS is sepsis. Inflammatory diseases include but are not limited to autoimmune diseases and atopic disorders. Other types of inflammatory diseases which are treatable with HLGAGs are refractory ulcerative colitis, Chrohn's disease, multiple sclerosis, autoimmune disease, non-specific ulcerative colitis and interstitial cystitis.

In one embodiment, the HLGAG preparations are used for inhibiting angiogenesis. An effective amount for inhibiting angiogenesis of the HLGAG preparation is administered to a subject in need of treatment thereof. Angiogenesis as used herein is the inappropriate formation of new blood vessels. "Angiogenesis" often occurs in tumors when endothelial cells secrete a group of growth factors that are mitogenic for endothelium causing the elongation and proliferation of endothelial cells which results in the generation of new blood vessels. Several of the angiogenic mitogens are heparin binding peptides which are related to endothelial cell growth factors. The inhibition of angiogenesis can cause tumor regression in animal models, suggesting a use as a therapeutic anticancer agent. An effective amount for inhibiting angiogenesis is an amount of HLGAG preparation which is sufficient to diminish the number of blood vessels growing into a tumor. This amount can be assessed in an animal model of tumors and angiogenesis, many of which are known in the art. Angiogenic disorders include, but are not limited to, neovascular disorders of the eye, osteoporosis, psoriasis, arthritis, cancer and cardiovascular disorders.

The HLGAG preparations are also useful for inhibiting neovascularization associated with eye disease. In another embodiment, the HLGAG preparation is administered to treat psoriasis. Psoriasis is a common dermatologic disease caused by chronic inflammation.

HLGAG containing compositions, may also inhibit cancer cell growth and metastasis. Thus the methods are useful for treating and/or preventing tumor cell proliferation or metastasis in a subject. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; leukemias, lymphomas; liver cancer; lung cancer (e.g. small cell and non-small cell); melanoma; neuroblastomas; oral cancer; ovarian cancer; pancreatic cancer; prostate cancer; rectal cancer; sarcomas; skin cancer; testicular cancer; thyroid cancer; and renal cancer, as well as other carcinomas and sarcomas.

A subject in need of cancer treatment may be a subject who has a high probability of developing cancer. These subjects include, for instance, subjects having a genetic abnormality, the presence of which has been demonstrated to have a correlative relation to a higher likelihood of developing a cancer and subjects exposed to cancer-causing agents such as tobacco, asbestos, or other chemical toxins, or a subject who has previously been treated for cancer and is in apparent remission.

Other Embodiments

This invention is further illustrated by the following examples that should not be construed as limiting. The contents of all references, patents and published patent applications cited throughout this application are incorporated herein by reference.

EXAMPLES

Example 1

Cloning and Recombinant Expression of B. thetaiotaomicron GAG Lyase I

The B. thetaiotaomicron GAG lyase I sequence (FIG. 1; SEQ ID NO:1), which is approximately 1251 nucleotides long contains a predicted methionine-initiated coding sequence of about 1179 nucleotides, including the termination codon (SEQ ID NO:1 in FIG. 1A). The coding sequence encodes a 392 amino acid protein (SEQ ID NO:2 in FIG. 1B).

The B. thetaiotaomicron GAG lyase amino acid sequence shares some structural homology to the F. heparinum heparinase I sequence. A comparison of the amino acid sequences of the two lyases is shown in FIG. 2.

The B. thetaiotaomicron GAG lyase gene was cloned by PCR using genomic DNA from B. thetaiotaomicron obtained from the American Type Culture Collection (ATCC), catalog no. 29148D. DNA oligonucleotide primers for M17 variant were synthesized by Integrated DNA technologies, Inc. (IDT) according to the following nucleotide sequences: 1) 5' CATATGCTGACTGCTCAGACTAAAAATAC 3' (forward primer) (SEQ ID NO:11); 2) 5' CTCGAGTTATCTTTC-CGAATATCCTGCGAGAT 3' (reverse primer) (SEQ ID NO:12). Primers were designed to introduce NdeI and XhoI endonuclease restriction sites at the 5' and 3' ends, respectively. The resulting gene sequence was cloned into pET28a bacterial expression plasmid (EMD Biosciences) as an NdeI-XhoI fragment for subsequent recombinant expression into E. coli strain BL21 (DE3), as an engineered fusion protein containing the sequence MGSSHHHHHHSSGLVPRGSH (SEQ ID NO:13) fused to the amino terminus of the B. thetaiotaomicron GAG lyase beginning at the methionine at position 17 (M17).

A B. thetaiotaomicron GAG lyase variant with a modified amino terminus that begins at position glutamine 26 (Q26) of the protein sequence listed in SEQ ID NO:2, was cloned into pET28a for recombinant expression as a fusion protein. The amino acid sequence and nucleic acid sequence encoding the Q26 variant are provided in SEQ ID NOs: 4 and 3, respectively DNA oligonucleotide primers for Q26 variant were synthesized by Integrated DNA technologies, Inc. (IDT) according to the following nucleotide sequences: 1) 5' CAT ATG CAA ACA CTG ATG CCA CTC ACC GAA 3' (forward primer) (SEQ ID NO:41) and 5' CTCGAGTTATCTTTC-CGAATATCCTGCGAGAT 3' (reverse primer) (SEQ ID NO:12).

Both the full length, M17, and Q26 B. thetaiotaomicron GAG lyase fusion proteins were recombinantly expressed in E. coli, yielding soluble, highly active enzyme that was fully capable of cleaving heparin and heparan sulfate (see Example 2 below). [Sequence verified plasmid pET28 containing either the M17 coding sequence or Q26 coding sequence was transformed into BL21 (DE3). 2 liter cultures were grown at room temperature (~22-25° C.) in LB media supplemented with 40 µg/mL kanamycin. Protein expression was induced with 500 µM IPTG added at an $A_{600}$ of 1.0. Induced cultures were allowed to grow for 15-18 hours at room temperature.

Recombinant B. thetaiotaomicron GAG lyase purification. Bacterial cells were harvested by centrifugation at 6000×g for 15 minutes and resuspended in 30 mL of binding buffer (50 mM $Na_2HPO_4$, pH 7.9, 0.5 M NaCl, and 5 mM imidazole). Lysis was initiated by the addition of 0.1 mg/mL lysozyme (20 minutes at room temperature) followed by intermittent sonication in an ice-water bath using a Misonex XL sonicator at 40-50% output. The crude lysate was fractionated by low-speed centrifugation (20,000×g; 4° C.; 30 minutes) and the supernatant was filtered through a 0.45 micron filter. The 6×-His recombinant B. thetaiotaomicron GAG lyase was purified by $Ni^{+2}$ chelation chromatography on a 5 mL Hi-Trap column (GE Healthcare) pre-charged with 200 mM $NiSO_4$ and subsequently equilibrated with binding buffer. The column was run at a flow rate of approximately 3 ml/minute that included an intermediate wash step with 50 mM imidazole. The lyase enzyme was eluted from the column in 5 mL fractions using high imidazole elution buffer (50 mM $Na_2HPO_4$, pH 7.9, 0.5 M NaCl, and 250 mM imidazole). These enzymes can also be purified using purification tags such as GST, MBP, Trx, DsbC, NusA or biotin The resulting peak was buffer exchanged on a Sephadex G-25 column equilibrated with 20 mM $Na_2HPO_4$, pH 6.8, 150 mM NaCl and subsequently subjected to cation exchange chromatography using a source 15S resin (GE healthcare) and applying a linear salt gradient from 0.05 M-1 M NaCl.

Protein concentrations were determined by the Bio-Rad protein assay and confirmed by UV spectroscopy. Protein purity was assessed by SDS-PAGE followed by Coomassie Brilliant Blue staining and/or Sypro Ruby Red (Invitrogen).

Example 2

Distinct Heparan Sulfate Substrate Specificities of B. thetaiotaomicron GAG Lyase I and F. heparinum Heparinases I and II The cleavage patterns and thereby the substrate specificities of recombinant B. thetaiotaomicron GAG lyase I and F. heparinum heparinases I and II were compared using heparan sulfate as a substrate. 200 µg of "HI" fraction of heparan sulfate (Celsus Labs) from porcine intestinal mucosa was digested with recombinant B. thetaiotaomicron GAG lyase I under conditions favorable to ensure a complete digestion. The HS was contacted with about 50 µg B-thetaiotaomicron GAG lyase I, 50 mM sodium phosphate, 100 mM NaCl, pH 8.0 at 37° C. for 18 hours. The lyase digestion products were analyzed by HPLC using strong anion chromatography (SAX-HPLC). SAX-HPLC conditions were as follows: 50 µg samples was injected at 1 mg/ml into a 4×250 mm CarboPac PA1 analytical scale column (Dionex Corporation). The flow rate was 1 ml/min. The mobile phase was 0.2M to 2 M NaCl in water, pH 3.5, gradient over 120 minutes. The column was preequilibrated with 0.2 M NaCl for 10 minutes. The results were compared with the results of the same experiment except that F. heparinum heparinase I was used to digest the heparan sulfate. Briefly, The HS was contacted with about 50 µg F. heparinum heparinase I, 25 mM sodium acetate, 1 mM calcium acetate, 5% glycine, pH 7.0 at 30° C. for 18 hours. The digestion profile for heparinase I is very similar to the profile for B. thetaiotaomicron GAG lyase I, except that novel peaks are present in the B. thetaiotaomicron GAG lyase I profile that are not present in the heparinase I profile, demonstrating that the lyases have non-identical substrate specificities. Further, the trace profile using *B. thetaiotaomicron* GAG lyase I was compared to the results of the same experiment except that *F. heparinum* heparinase II was used to digest the heparan sulfate. Briefly, The HI was contacted with about 50 μg *F. heparinum* heparinase II, 25 mM sodium acetate, 1 mM calcium acetate, pH 7.0 at 37° C. for 18 hours. In this case, the digestion profile using heparinase II is very much distinct from the digestion profile of *B. thetaiotaomicron* GAG lyase and *F. heparinum* heparinase I. These data demonstrate that the *B. thetaiotaomicron* GAG lyase substrate specificity is distinct from the specificities of *F. heparinum* heparinases I and II, but is more "heparin like" (e.g., more similar to *F. heparinum* heparinase I) than "heparan sulfate-like" (e.g., it is less like *F. heparinum* heparinase II).

Example 3

Depolymerization and Neutralization of ARIXTRA® by *B. thetaiotaomicron* GAG Lyase I Recombinant *B. thetaiotaomicron* GAG lyase I can cleave and thereby neutralize the ATIII pentasaccharide ARIXTRA® into a pentasulfated trisaccharide and an unsaturated disulfated disaccharide. ARIXTRA® is an anti-thrombotic drug that acts as a selective inhibitor of Factor Xa, a component of the coagulation cascade. Depolymerization of ARIXTRA® is unequivocally demonstrated by matrix assisted laser desorption ionization mass spectrometry (MALDI-MS) (FIG. 7). Panel A shows the scan of ARIXTRA® in the absence of a lyase. The structure of ARIXTRA® is also shown. Panel B shows the scan after cleavage of ARIXTRA® with *B. thetaiotaomicron* GAG lyase. Briefly, 1 mg/ml ARIXTRA® in a 20 μL reaction volume was treated with 5 μg *B. thetaiotaomicron* GAG lyase 1.25 mM sodium acetate, 1 mM calcium acetate, pH 7.0 at 37° C. for 2 hours. Note the disappearance in panel B of mass 4723.7 Da (net mass=1506 Da) present in panel A with concomitant appearance of mass 4133.2 Da (net mass=915.6 Da). The latter mass represents the pentasulfated trisaccharide cleavage product. In cleaving Arixtra into two smaller fragments, the drug's anti-Xa activity is effectively neutralized by the *B. thetaiotaomicron* GAG lyase.

Example 4

Cloning and Recombinant Expression of *B. thetaiotaomicron* GAG Lyase II

The complete coding sequence of a *B. thetaiotaomicron* GAG lyase II (herein described as "full-length gene") as well as the two variants described herein were cloned by PCR using genomic DNA from *Bacteroides thetaiotaomicron* as obtained from American Type Culture Collection (ATCC), catalog no. 29148D. DNA oligonucleotide primers were synthesized by Integrated DNA technologies (IDT), Inc. according to the following nucleotide sequences: 1) For the full-length gene: 5' CAT ATG AAT AAA ACC CTG AAA TAT ATC GTC CTG 3' (forward primer) (SEQ ID NO:14), 5' CTC GAG TTA TAA TTT ATA TTT TAA TGA CTG TTT CTT GC 3' (reverse primer) (SEQ ID NO:15); 2) Gene encoding variant No. 1 (amino terminal truncation to remove putative signal sequence): 5' CAT ATG CAA GAG TTG AAA AGC GAG GTA TTC TCG 3' (forward primer) (SEQ ID NO:16), 5' CTC GAG TTA TAA TTT ATA TTT TAA TGA CTG TTT CTT GC 3' (note: same reverse primer listed above as for full-length gene) (SEQ ID NO:15). Primers were designed to introduce Nde 1 and Xho 1 endonuclease restriction sites at the 5' and 3' ends, respectively. Cloning of described gene sequence into pET28b bacterial expression plasmid (EMD Biosciences) as an Nde 1-Xho 1 fragment for subsequent recombinant expression into *E. coli* strain BL21 (DE3) as engineered fusion protein containing the sequence MGSSHHHHHHSSGLVPRGSHMNKTLKY . . . KVNGKKQSLKYKL (SEQ ID NO:17) or MGSSHHHHHHSSGLVPRGSHMQELKSEVF . . . KVNGKKQSLKYKL (SEQ ID NO:18) for the full-length gene and variant 1 (the Q23 variant, SEQ ID NO:8), respectively (*B. thetaiotaomicron* GAG lyase sequence is denoted in bold). See FIG. 4 for complete sequence.

Another variant, the K169 variant (SEQ ID NO:10) represents an engineered deletion of 18 contiguous amino acids comprising an internal region within the protein and possessing the following linear sequence: KMDKKEYELVSDGKIKGE. (SEQ ID NO:19) Deletion of this region in the gene sequence (FIG. 5A) and in the corresponding protein sequence (FIG. 5B) is noted by grey shading. Deletion of this region at the DNA level was accomplished by PCR-based mutagenesis using the Quick-change kit (Stratagene) in accordance with the manufacturer's instructions. Mutagenesis primers used to make this deletion at the gene (DNA) level were of the following sequence: 5' GG ATT AAA AAG AAT CCG TTG GTG GAA AAT GTA CGT TTC GC 3' (SEQ ID NO:20) and 5' CC TAA TTT TTC TTA GGC AAC CAC CTT TTA CAT GCA AAG CG 3' (SEQ ID NO:21) corresponding to the sense and anti-sense strands, respectively. Recombinant expression of this described gene variant in *E. coli* likewise based on the pET-based expression for recombinant expression was also achieved. Purification was carried out largely as described for the *B. thetaiotaomicron* GAG lyase I.

Preliminary biochemical characterization of this variant indicates that deletion of described amino acids is not deleterious to the soluble expression of the enzyme nor to its ability to cleave both heparin and heparan sulfate. It does suggest, however a potential difference in the catalytic efficiency and/or substrate specificity of this enzyme variant relative to the full-length protein.

Example 5

Cloning, Recombinant Expression and Purification of *B. thetaiotaomicron* GAG Lyase III GAG lyase III gene was cloned by PCR using genomic DNA from *Bacteroides thetaiotaomicron* obtained from American Type Culture Collection (ATCC), catalog number 29148D. The nucleotide sequence (SEQ ID NO: 28) of a full-length gene of at least 2622 base pairs is shown in FIG. 8. The amino acid sequence (SEQ ID NO: 29) encoding a polypeptide of at least 873 amino acids existing in the linear sequence is shown in FIG. 9.

DNA oligonucleotide primers were synthesized by Integrated DNA technologies (IDT), Inc. according to the following nucleotide sequences: 1) 5'CATATGATGAAACAACGATATTATATTTTC 3' (forward primer) (SEQ ID NO: 30); 2) 5'GGATCCTCGAGTTATATCTCAAAATCCGGTAAATAGTC 3' (reverse primer) (SEQ ID NO: 31). Primers were designed to introduce Nde 1 and Bam H1/Xho 1 endonuclease restriction sites at the 5' and 3' ends, respectively. The described gene sequence (SEQ ID NO:28) was cloned into pET28a bacterial expression plasmid (EMD Biosciences) as an Nde 1-Xho 1 fragment for subsequent recombinant expression in *E. coli* strain BL21 (DE3), engineered as a 6× Histidine fusion protein.

Likewise, a gene variant of GAG lyase III (SEQ ID NO:33 and 34) with modified amino terminus that begins at position glutamine 23 (Q23) in the protein sequence listed (SEQ ID NO:29) was cloned into pET28a for recombinant expression.

To do so, the following forward (5') primer was used: CATAT-GCAGAAAAGCATCCTGCGTCTGAGT 3' (SEQ ID NO:35).

The primary amino acid sequence of the cloned enzyme was compared directly with four functionally-related lyases from both *Bacteroides thetaiotaomicron* and *Flavobacterium heparinum*. The multiple sequence alignment (made using CLUSTALW program) is depicted in FIG. 10. The alignment shows that the GAG lyase III disclosed herein is distinct from the other enzymes to which it is being compared.

The enzyme was recombinantly expressed in *E. coli* as a highly soluble, active amino-terminal variant beginning at Q23 (SEQ ID NO: 33 and 34), as shown in FIG. 9. The Q23 variant was readily expressed in *E. coli* as a highly soluble enzyme. Expression of this enzyme as an amino terminal 6x histidine fusion protein also facilitated purification in essentially a single purification step. Additional purification included cation exchange chromatography on a Source 15S column utilizing a linear gradient from 0.05 M to 1 M NaCl. Other purification methods that can be used to obtain these enzymes include affinity purification tags such as GST, MBP, Trx, DsbC, NusA or biotin.

Example 6

Analysis of Function and Enzyme Activity of *B. thetaiotaomicron* GAG Lyase III

The ability of the recombinant GAG lyase III to cleave heparin-like glycosaminoglycans was evaluated. Heparinase II and heparinase III from *Flavobacterium heparinum* were included for comparison. Cleavage of four "heparin-like" substrates: porcine intestinal heparin, two different heparan sulfates (designated HI and HO, each with a varying degree of sulfation), and enoxaparin (a low-molecular weight pharmaceutical heparin), was analyzed. Biochemical enzyme activity was assessed both for extent of cleavage (product formation) as measured by UV absorbance at 232 nm, as well as for specificity. The latter parameter was assessed by fractionation of the di-, tetra-, and higher oligosaccharide products by capillary electrophoresis (CE).

Figure 11:
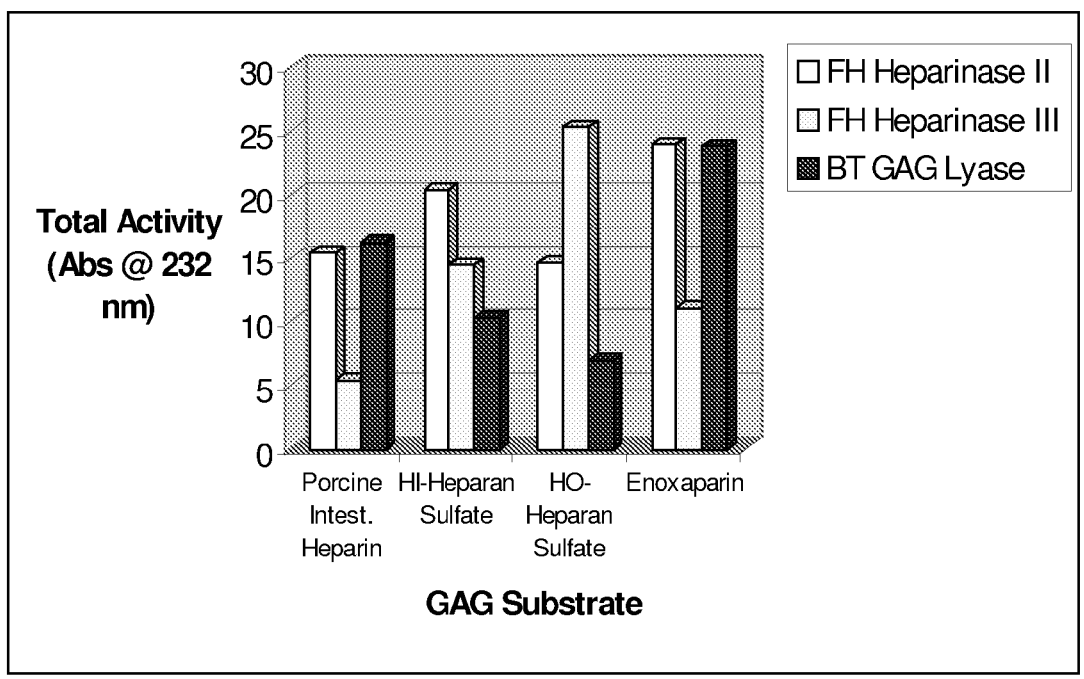
FIG. 11 depicts enzyme activities of GAG lyase III isolated from *Bacteroides thetaiotaomicron* (BT GAG Lyase), heparinase II isolated from *Flavobacterium heparinum* (FH Heparinase II) and heparinase III isolated from *Flavobacterium heparinum* (FH Heparinase III). The enzyme activity represents substrate specificity of the three tested enzymes. The four "heparin-like" substrates tested were: porcine intestinal heparin, two different heparan sulfates (designated "HI" and "HO," each one varying in the degree of sulfation), and low molecular weight pharmaceutical heparin, enoxaparin. Enzyme activity shown depicts total cleavage activity toward these substrates in an exhaustive digestion, as assessed by absorbance at 232 nm.

Total enzyme activity of the *B. thetaiotaomicron* GAG lyase III is summarized in FIG. 11 These data show that GAG lyase III exhibited a preference for highly sulfated, "heparin-like" GAGs and their lower molecular weight derivatives. At the same time, this enzyme was able to cleave GAGs with lesser sulfation, i.e., GAGs that are more "heparan sulfate-like." At the same time, the substrate profile depicted in FIG. 11 demonstrates that the specificity of that lyase was distinct from both heparinase II and heparinase III derived from *F. heparinum*.

Figure 12:
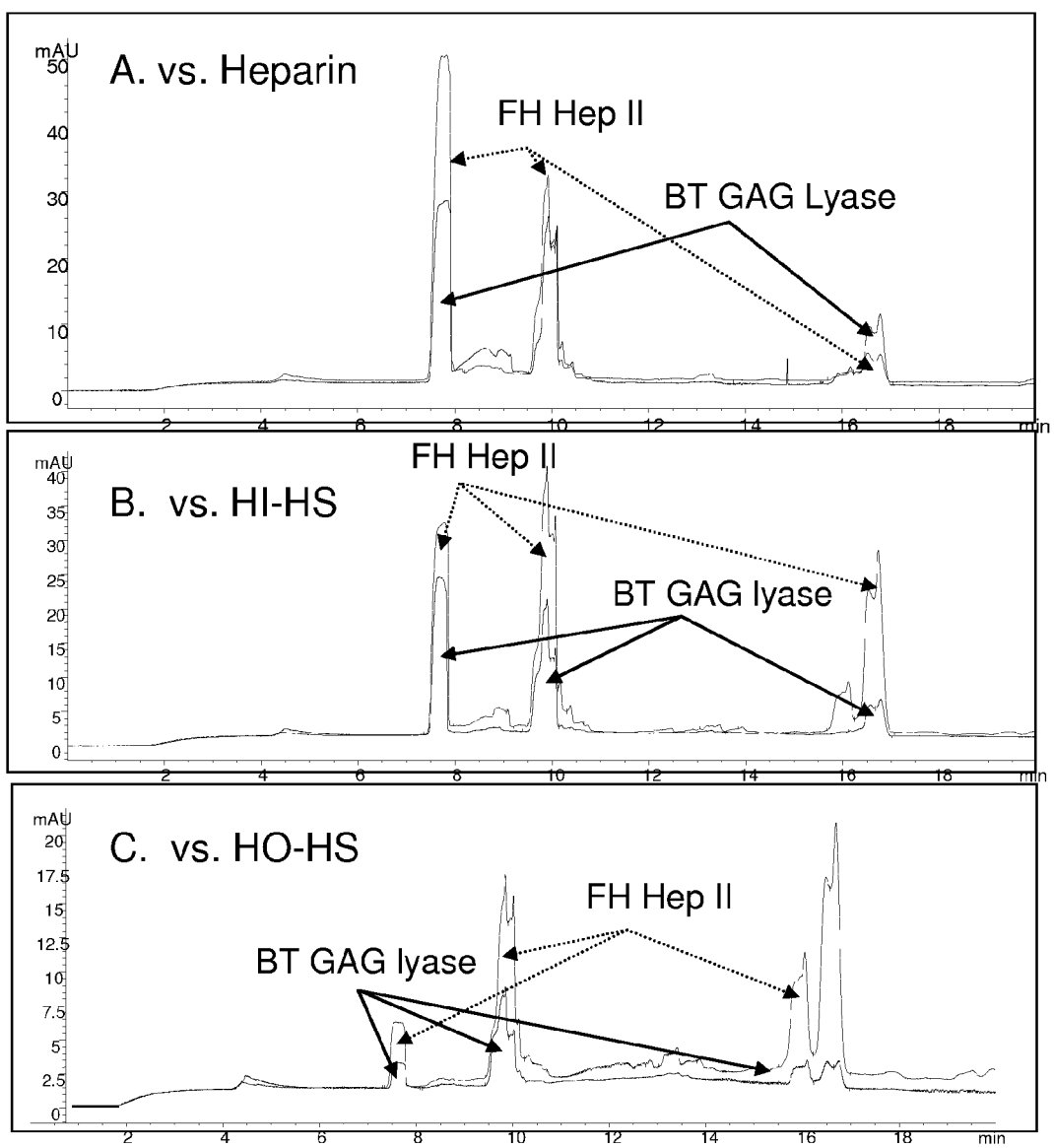
FIG. 12 depicts cleavage activities of GAG lyase III isolated from *Bacteroides thetaiotaomicron* (BT GAG Lyase) and heparinase II isolated from *Flavobacterium heparinum* (FH Hep II). The cleavage activity represents substrate specificity of the tested enzymes. The actual cleavage products are fractionated by capillary electrophoresis and monitored by absorbance at 232 nm (Y axis). Solid line depicts BT GAG Lyase and dotted line depicts FH Hep II.
Figure 16:
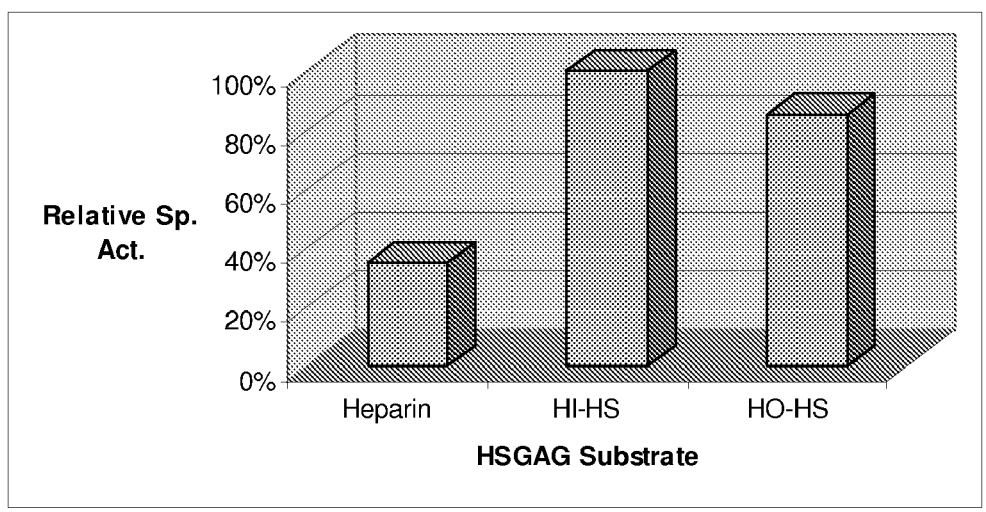
FIG. 16 depicts the substrate specificity of *Bacteroides thetaiotaomicron* GAG lyase IV against three different substrates, namely unfractionated heparin (Heparin) and two fractions of heparin sulfate (HS) referred to as "HO-HS" and "HI-HS".

The distinction between *B. thetaiotaomicron* GAG lyase III and heparinase II from *F. heparinum* was analyzed further and is shown in FIG. 12. Cleavage of three substrates: heparin, and two different heparan sulfates (designated HI and HO, each with a varying degree of sulfation) was analyzed. The cleavage products were fractionated by capillary electrophoresis and monitored by absorbance at 232 nm (Y axis). These data indicates that while the two enzymes are functionally related, their substrate specificities are not identical.

Example 7

Cloning, Recombinant Expression and Purification of *B. thetaiotaomicron* GAG Lyase IV The *B. thetaiotaomicron* GAG lyase IV sequence (FIG. 13, SEQ ID NO:36), which is approximately 2109 nucleotides long encodes a polypeptide of at least 702 amino acids (FIG. 14, SEQ ID NO:37).

The GAG lyase IV gene was cloned by PCR using genomic DNA from *B. thetaiotaomicron* as obtained from American Type Culture Collection (ATCC), catalog no. 29148). DNA oligonucleotide primers were synthesized by Integrated DNA technologies (IDT), Inc. according to the following nucleotide sequences:

1) 5'CCA TGG CAT ATG AAG AAC ATC TTC TTT ATT TGC 3' (forward primer, SEQ ID NO:32);
2) 5'CTC GAG TTA TAA GGT ATA AGA TAA TGT ATG TGT 3' (reverse primer, SEQ ID NO:40).

Primers were designed to introduce Nde 1 and Xho 1 endonuclease restriction sites as indicated in bold. Three amplified gene was subcloned into the T7-based expression vector pET28 for heterologous expression in *E. coli* as an engineered fusion in which a 6x histidine tag is present at the amino terminus as a means to purify the recombinantly expressed protein. Other methods can be used to purify this enzyme including the use of GST, MBP, Trx, DsbC, NusA and biotinylation. A variant of this gene was also constructed, namely one in which the first 19 amino acids representing a putative bacterial secretion signal was removed. This variant (known as D20) begins at aspartate 20 (asp 20).

The primary amino acid sequence of the cloned enzyme was compared directly with four functionally related lyases from both *B. thetaiotaomicron* and *Flavobacterium heparinum*. The multiple sequence alignment is depicted in FIG. 15. The amino acid sequence corresponding to *B. thetaiotaomicron* lyase IV exhibits approximately 30% identity with heparin lyase III from *F. heparinum*. Thus, from this alignment, it is clear that the GAG lyase described in this disclosure is distinct from the other enzymes to which it is being compared.

The functionality of this putative lyase was also examined. In particular, the ability of the recombinant *B. thetaiotaomicron* lyase IV enzyme to cleave heparin-like glycosaminoglycans of differing composition, particularly as it relates to sulfation density was evaluated. In this experiment, three GAG substrates were screened: heparin from pig intestinal mucosa (PM), "HI" fraction of heparan sulfate likewise isolated from pig intestinal mucosa (HI-HS), and so-called "HO" fraction of heparan sulfate representing the lowest sulfation density. Biochemical enzyme activity was assessed both for rate of cleavage as measured in a real-time, UV-based kinetic assay in addition to the extent of cleavage (product formation) as measured by UV absorbance at 232 nm. Data are summarized in FIG. 18 and represent relative values normalized to the highest activity reported. Based on these data, this recombinantly expressed GAG lyase exhibits a preference for GAGs of medium sulfation density. This preference may be broadly described as heparan sulfate-like rather than heparin-like.

The *B. thetaiotaomicron* GAG lyase IV may also have a substrate specificity that is unique when compared to other heparan sulfate lyases such as heparinase III from *F. heparinum*—or even other "heparinase III-like" enzymes from *Bacteroides*. In particular, this enzyme may cleave disaccharides not commonly found in either heparin or most fractions of heparan sulfate, for example, $I_{2S}H_{NAc}$. It is also possible that this enzyme may cleave heparin in such a manner as to preserve, at least in part, the AT-III binding site.

EQUIVALENTS

Those skilled in the art will recognize, or be able to ascertain using no more than routine experimentation, many equivalents to the specific embodiments of the invention described herein. Such equivalents are intended to be encompassed by the following claims.

SEQUENCE LISTING

<160> NUMBER OF SEQ ID NOS: 41

<210> SEQ ID NO 1
<211> LENGTH: 1251
<212> TYPE: DNA
<213> ORGANISM: Bacteroides thetaiotaomicron

<400> SEQUENCE: 1

```
gacaaacgaa aggcagccgt aagggttgcc tttcgtattt ttgcaccgtc gataaactta      60
ataccggata gaatgaaaaa atacattttg gttatttata tgatggcggc aggatgcacg     120
atgctgactg ctcagactaa aaatacgcaa acactgatgc cactcaccga acgggtaaac     180
gtacaggctg actctgcacg tatcaaccag attattgacg gttgctgggt agctgtcggg     240
acgaataaac ctcatgccat tcagcgtgat tttaccaacc tgtttgatgg caagccctcc     300
tatcgctttg aactcaaaac tgaagacaat acactggaag gttatgcgaa aggagaaacg     360
aaaggacgtg ccgagttttc atattgctat gcaacttccg acgatttcag gggattacct     420
gccgacgttt atcagaaagc acagatcaca agacagtttt atcatcacgg aagggagct     480
tgtccgcaag gaagttcccg cgactatgag ttttcggttt atattccttc ttctttagac     540
agcaatgtct ccaccatctt tgcccaatgg cacggaatgc cgaccggac gctggtccag     600
actcctcagg gcgaggtgaa gaaactgact gttgacgaat tgtagaact ggaaaaaacg      660
accttcttca aaagaatgt cggacacgaa aaagtggcca gactggataa acaaggtaat      720
ccggtgaaag ataaaaatgg aaaacctgta tataaggcag gaaaacccaa cggatggttg     780
gttgaacagg gaggatacc gccattggca ttcggatttt ccggaggact gttttatatc     840
aaagcaaact ccgaccgtaa atggctgaca gacaaagatg accgttgcaa tgcaaacccg     900
ggaaagacgc ccgttatgaa accgctgact tctgaataca aggcatccac cattgcctac     960
aaattacctt ttgccgattt cccgaaagac tgctggatta cttcccgtgt ccatatcgac    1020
tggacggtct atggcaagga agcggaaacg attgtgaaac cgggcatgct ggatgtacgg    1080
atggattatc aggagcaagg taagaaagtg agcaaacaca ttgtcgataa tgagaagatt    1140
ctgattggac gtaacgacga agacgggtat tacttttaagt tcggaattta ccgcgtaggt    1200
gatagtaccg ttcccgtttg ctacaatctc gcaggatatt cggaaagata a             1251
```

<210> SEQ ID NO 2
<211> LENGTH: 392
<212> TYPE: PRT
<213> ORGANISM: Bacteroides thetaiotaomicron

<400> SEQUENCE: 2

```
Met Lys Lys Tyr Ile Leu Val Ile Tyr Met Met Ala Ala Gly Cys Thr
 1               5                  10                  15

Met Leu Thr Ala Gln Thr Lys Asn Thr Gln Thr Leu Met Pro Leu Thr
             20                  25                  30

Glu Arg Val Asn Val Gln Ala Asp Ser Ala Arg Ile Asn Gln Ile Ile
         35                  40                  45

Asp Gly Cys Trp Val Ala Val Gly Thr Asn Lys Pro His Ala Ile Gln
     50                  55                  60

Arg Asp Phe Thr Asn Leu Phe Asp Gly Lys Pro Ser Tyr Arg Phe Glu
 65                  70                  75                  80

Leu Lys Thr Glu Asp Asn Thr Leu Glu Gly Tyr Ala Lys Gly Glu Thr
                 85                  90                  95
```

-continued

```
Lys Gly Arg Ala Glu Phe Ser Tyr Cys Tyr Ala Thr Ser Asp Asp Phe
                100                 105                 110

Arg Gly Leu Pro Ala Asp Val Tyr Gln Lys Ala Gln Ile Thr Lys Thr
            115                 120                 125

Val Tyr His His Gly Lys Gly Ala Cys Pro Gln Gly Ser Ser Arg Asp
        130                 135                 140

Tyr Glu Phe Ser Val Tyr Ile Pro Ser Ser Leu Asp Ser Asn Val Ser
145                 150                 155                 160

Thr Ile Phe Ala Gln Trp His Gly Met Pro Asp Arg Thr Leu Val Gln
                165                 170                 175

Thr Pro Gln Gly Glu Val Lys Lys Leu Thr Val Asp Glu Phe Val Glu
            180                 185                 190

Leu Glu Lys Thr Thr Phe Phe Lys Lys Asn Val Gly His Glu Lys Val
        195                 200                 205

Ala Arg Leu Asp Lys Gln Gly Asn Pro Val Lys Asp Lys Asn Gly Lys
210                 215                 220

Pro Val Tyr Lys Ala Gly Lys Pro Asn Gly Trp Leu Val Glu Gln Gly
225                 230                 235                 240

Gly Tyr Pro Pro Leu Ala Phe Gly Phe Ser Gly Gly Leu Phe Tyr Ile
                245                 250                 255

Lys Ala Asn Ser Asp Arg Lys Trp Leu Thr Asp Lys Asp Arg Cys
            260                 265                 270

Asn Ala Asn Pro Gly Lys Thr Pro Val Met Lys Pro Leu Thr Ser Glu
        275                 280                 285

Tyr Lys Ala Ser Thr Ile Ala Tyr Lys Leu Pro Phe Ala Asp Phe Pro
            290                 295                 300

Lys Asp Cys Trp Ile Thr Phe Arg Val His Ile Asp Trp Thr Val Tyr
305                 310                 315                 320

Gly Lys Glu Ala Glu Thr Ile Val Lys Pro Gly Met Leu Asp Val Arg
                325                 330                 335

Met Asp Tyr Gln Glu Gln Gly Lys Lys Val Ser Lys His Ile Val Asp
            340                 345                 350

Asn Glu Lys Ile Leu Ile Gly Arg Asn Asp Glu Asp Gly Tyr Tyr Phe
        355                 360                 365

Lys Phe Gly Ile Tyr Arg Val Gly Asp Ser Thr Val Pro Val Cys Tyr
370                 375                 380

Asn Leu Ala Gly Tyr Ser Glu Arg
385                 390
```

<210> SEQ ID NO 3
<211> LENGTH: 1179
<212> TYPE: DNA
<213> ORGANISM: Bacteroides thetaiotaomicron

<400> SEQUENCE: 3

| | | |
|---|---|---|
| atgaaaaaat acattttggt tatttatatg atggcggcag atgcacgat gctgactgct | 60 |
| cagactaaaa atacgcaaac actgatgcca ctcaccgaac gggtaaacgt acaggctgac | 120 |
| tctgcacgta tcaaccagat tattgacggt tgctgggtag ctgtcgggac gaataaacct | 180 |
| catgccattc agcgtgattt taccaacctg tttgatggca agccctccta tcgctttgaa | 240 |
| ctcaaaactg aagacaatac actggaaggt tatgcgaaag gagaaacgaa aggacgtgcc | 300 |
| gagttttcat attgctatgc aacttccgac gatttcaggg gattacctgc cgacgtttat | 360 |
| cagaaagcac agatcacaaa gacagtttat catcacggga agggagcttg tccgcaagga | 420 |
| agttcccgcg actatgagtt ttcggtttat attccttctt ctttagacag caatgtctcc | 480 |

```
accatctttg cccaatggca cggaatgccc gaccggacgc tggtccagac tcctcagggc    540
gaggtgaaga aactgactgt tgacgaattt gtagaactgg aaaaaacgac cttcttcaaa    600
aagaatgtcg gacacgaaaa agtggccaga ctggataaac aaggtaatcc ggtgaaagat    660
aaaaatggaa aacctgtata taaggcagga aaacccaacg gatggttggt tgaacaggga    720
ggatacccgc cattggcatt cggatttttc cgaggactgt tttatatcaa agcaaactcc    780
gaccgtaaat ggctgacaga caagatgac cgttgcaatg caaacccggg aaagacgccc     840
gttatgaaac cgctgacttc tgaatacaag gcatccacca ttgcctacaa attacctttt    900
gccgatttcc cgaaagactg ctggattact ttccgtgtcc atatcgactg gacggtctat    960
ggcaaggaag cggaaacgat tgtgaaaccg ggcatgctgg atgtacggat ggattatcag    1020
gagcaaggta agaaagtgag caaacacatt gtcgataatg agaagattct gattggacgt    1080
aacgacgaag acgggtatta cttttaagttc ggaatttacc gcgtaggtga tagtaccgtt    1140
cccgtttgct acaatctcgc aggatattcg gaaagataa                           1179
```

<210> SEQ ID NO 4
<211> LENGTH: 376
<212> TYPE: PRT
<213> ORGANISM: Bacteroides thetaiotaomicron

<400> SEQUENCE: 4

```
Met Leu Thr Ala Gln Thr Lys Asn Thr Gln Thr Leu Met Pro Leu Thr
 1               5                  10                  15

Glu Arg Val Asn Val Gln Ala Asp Ser Ala Arg Ile Asn Gln Ile Ile
            20                  25                  30

Asp Gly Cys Trp Val Ala Val Gly Thr Asn Lys Pro His Ala Ile Gln
        35                  40                  45

Arg Asp Phe Thr Asn Leu Phe Asp Gly Lys Pro Ser Tyr Arg Phe Glu
    50                  55                  60

Leu Lys Thr Glu Asp Asn Thr Leu Glu Gly Tyr Ala Lys Gly Glu Thr
65                  70                  75                  80

Lys Gly Arg Ala Glu Phe Ser Tyr Cys Tyr Ala Thr Ser Asp Asp Phe
                85                  90                  95

Arg Gly Leu Pro Ala Asp Val Tyr Gln Lys Ala Gln Ile Thr Lys Thr
            100                 105                 110

Val Tyr His His Gly Lys Gly Ala Cys Pro Gln Gly Ser Ser Arg Asp
        115                 120                 125

Tyr Glu Phe Ser Val Tyr Ile Pro Ser Ser Leu Asp Ser Asn Val Ser
    130                 135                 140

Thr Ile Phe Ala Gln Trp His Gly Met Pro Asp Arg Thr Leu Val Gln
145                 150                 155                 160

Thr Pro Gln Gly Glu Val Lys Lys Leu Thr Val Asp Glu Phe Val Glu
                165                 170                 175

Leu Glu Lys Thr Thr Phe Phe Lys Lys Asn Val Gly His Glu Lys Val
            180                 185                 190

Ala Arg Leu Asp Lys Gln Gly Asn Pro Val Lys Asp Lys Asn Gly Lys
        195                 200                 205

Pro Val Tyr Lys Ala Gly Lys Pro Asn Gly Trp Leu Val Glu Gln Gly
    210                 215                 220

Gly Tyr Pro Pro Leu Ala Phe Gly Phe Ser Gly Gly Leu Phe Tyr Ile
225                 230                 235                 240

Lys Ala Asn Ser Asp Arg Lys Trp Leu Thr Asp Lys Asp Asp Arg Cys
                245                 250                 255
```

Asn Ala Asn Pro Gly Lys Thr Pro Val Met Lys Pro Leu Thr Ser Glu
            260                 265                 270

Tyr Lys Ala Ser Thr Ile Ala Tyr Lys Leu Pro Phe Ala Asp Phe Pro
        275                 280                 285

Lys Asp Cys Trp Ile Thr Phe Arg Val His Ile Asp Trp Thr Val Tyr
    290                 295                 300

Gly Lys Glu Ala Glu Thr Ile Val Lys Pro Gly Met Leu Asp Val Arg
305                 310                 315                 320

Met Asp Tyr Gln Glu Gln Gly Lys Lys Val Ser Lys His Ile Val Asp
            325                 330                 335

Asn Glu Lys Ile Leu Ile Gly Arg Asn Asp Glu Asp Gly Tyr Tyr Phe
        340                 345                 350

Lys Phe Gly Ile Tyr Arg Val Gly Asp Ser Thr Val Pro Val Cys Tyr
    355                 360                 365

Asn Leu Ala Gly Tyr Ser Glu Arg
    370                 375

<210> SEQ ID NO 5
<211> LENGTH: 2001
<212> TYPE: DNA
<213> ORGANISM: Bacteroides thetaiotaomicron

<400> SEQUENCE: 5
atgaataaaa ccctgaaata tatcgtcctg ctgacatttg cttgtttcgt aggcaaaggc    60
tatgcccaag agttgaaaag cgaggtattc tcgcttctca acctggacta ccccggattg   120
gagaaagtaa aagccttaca tcaggaaggc aaagatgagg atgccgcaaa agcactgctc   180
gactactacc gtgcacgtac gaatgtgaag acgccggata ttaatctgaa aaagatcact   240
atcggcaaag aagaacagca atgggcggat gacggattga agcatacatt ctttgttcac   300
aaaggctatc agccttctta caactacgga gaagatatca actggcaata ctggccggtg   360
aaagacaatg aactccgctg gcagttgcac cgtcataaat ggtttactcc gatgggtaag   420
gcataccgtg tatcgggtga cgagaaatat gccaaagaat gggcatacca atacatcgac   480
tggattaaaa agaatccgtt ggtgaagatg gacaagaaag aatacgaact ggtaagtgac   540
ggtaagatta aaggcgaagt ggaaaatgta cgtttcgcat ggcgtccgct ggaagtcagt   600
aatcgtctgc aggatcagac tacccagttc cagttgttcc tcccctctcc ttctttcact   660
ccggatttcc tgactgaatt tctggtgaac tatcataaac atgccgtaca tattctggct   720
aattactctg atcagggtaa tcacttgttg ttcgaagccc agcgtatgat ttatgcaggt   780
gcattcttcc cggaatttaa agaagctccg gcctggagaa aaagcggtat cgacattctg   840
aaccgtgaag taaacgtaca ggtttacaac gatggcggcc agtttgaact tgacccgcat   900
tatcatcttg ctgctatcaa tatcttctgc aaggcattgg gtatcgcgga tgttaacgga   960
ttccgtaatg agttcccaca ggaatatctg gatactatcg aaaagatgat catgttctat  1020
gccaatattt cttccccgga ttacacaaat ccgtgtttca gtgatgctaa atcacagaa   1080 aagaaagaaa tgctgaagaa ctatcgtgca tggagcaaac tgttcccgaa aaacgaaact  1140
atcaagtatt tggcaacaga cggcaaagaa ggcgcgttac ccgattatat gtcgaaaggt  1200
ttcctgaaat caggtttctt tgtgttccgc aattcctggg aatggatgc tacacaaatg   1260 gtagtaaaag ccggtccgaa aggtttctgg cactgtcagc cggataacgg tactttcgaa  1320
atgtggttta acggcaagaa cctgttccca gactccggtt cgtatgtgta tgccggtgaa  1380
ggcgaagtga tggaacaacg caactggcat cgtcagactt ccgtacacaa caccgtgact  1440

-continued

```
ctggacaata agaatctgga aacaaccgaa tctgttacta aactgtggca gccggaaggc    1500
aatatccaga ccttggttac agaaaaccca agctacaaga acttcaagca ccgccgttcg    1560
gtcttcttcg tagacaatac ctactttgtc attgtagatg aagtatcagg cagcgccaaa    1620
ggttctgtca acctgcacta tcagatgccg aaaggtgaga tagccaacag ccgtgaagac    1680
atgacattcc tgactcaatt cgaagatgga agcaacatga acttcaatg cttcggccct    1740 gaaggcatga gcatgaaaaa agagccggga tggtgttcta ctgcatatcg caagcgctac    1800
aaacgtatga atgtttcatt caacgtaaag aaagacaatg agaatgcggt acgttacatc    1860
acagttattt acccagtcaa gaagagcgca gatgcccta aatttgacgc taagttcaag    1920
aacaaaacgt tcgatgaaaa cggactggaa atagaagtga aagtaaacgg caagaaacag    1980
tcattaaaat ataaattata a                                             2001
```

<210> SEQ ID NO 6
<211> LENGTH: 666
<212> TYPE: PRT
<213> ORGANISM: Bacteroides thetaiotaomicron

<400> SEQUENCE: 6

```
Met Asn Lys Thr Leu Lys Tyr Ile Val Leu Leu Thr Phe Ala Cys Phe
 1               5                  10                  15

Val Gly Lys Gly Tyr Ala Gln Glu Leu Lys Ser Glu Val Phe Ser Leu
            20                  25                  30

Leu Asn Leu Asp Tyr Pro Gly Leu Glu Lys Val Lys Ala Leu His Gln
        35                  40                  45

Glu Gly Lys Asp Glu Asp Ala Ala Lys Ala Leu Leu Asp Tyr Tyr Arg
    50                  55                  60

Ala Arg Thr Asn Val Lys Thr Pro Asp Ile Asn Leu Lys Lys Ile Thr
65                  70                  75                  80

Ile Gly Lys Glu Glu Gln Gln Trp Ala Asp Asp Gly Leu Lys His Thr
                85                  90                  95

Phe Phe Val His Lys Gly Tyr Gln Pro Ser Tyr Asn Tyr Gly Glu Asp
            100                 105                 110

Ile Asn Trp Gln Tyr Trp Pro Val Lys Asp Asn Glu Leu Arg Trp Gln
        115                 120                 125

Leu His Arg His Lys Trp Phe Thr Pro Met Gly Lys Ala Tyr Arg Val
    130                 135                 140

Ser Gly Asp Glu Lys Tyr Ala Lys Glu Trp Ala Tyr Gln Tyr Ile Asp
145                 150                 155                 160

Trp Ile Lys Lys Asn Pro Leu Val Lys Met Asp Lys Lys Glu Tyr Glu
                165                 170                 175

Leu Val Ser Asp Gly Lys Ile Lys Gly Glu Val Glu Asn Val Arg Phe
            180                 185                 190

Ala Trp Arg Pro Leu Glu Val Ser Asn Arg Leu Gln Asp Gln Thr Thr
        195                 200                 205

Gln Phe Gln Leu Phe Leu Pro Ser Pro Ser Phe Thr Pro Asp Phe Leu
    210                 215                 220

Thr Glu Phe Leu Val Asn Tyr His Lys His Ala Val His Ile Leu Ala
225                 230                 235                 240

Asn Tyr Ser Asp Gln Gly Asn His Leu Leu Phe Glu Ala Gln Arg Met
                245                 250                 255

Ile Tyr Ala Gly Ala Phe Phe Pro Glu Phe Lys Glu Ala Pro Ala Trp
            260                 265                 270
```

```
Arg Lys Ser Gly Ile Asp Ile Leu Asn Arg Glu Val Asn Val Gln Val
        275                 280                 285
Tyr Asn Asp Gly Gly Gln Phe Glu Leu Asp Pro His Tyr His Leu Ala
    290                 295                 300
Ala Ile Asn Ile Phe Cys Lys Ala Leu Gly Ile Ala Asp Val Asn Gly
305                 310                 315                 320
Phe Arg Asn Glu Phe Pro Gln Glu Tyr Leu Asp Thr Ile Glu Lys Met
                325                 330                 335
Ile Met Phe Tyr Ala Asn Ile Ser Phe Pro Asp Tyr Thr Asn Pro Cys
            340                 345                 350
Phe Ser Asp Ala Lys Ile Thr Glu Lys Glu Met Leu Lys Asn Tyr
        355                 360                 365
Arg Ala Trp Ser Lys Leu Phe Pro Lys Asn Glu Thr Ile Lys Tyr Leu
    370                 375                 380
Ala Thr Asp Gly Lys Glu Gly Ala Leu Pro Asp Tyr Met Ser Lys Gly
385                 390                 395                 400
Phe Leu Lys Ser Gly Phe Phe Val Phe Arg Asn Ser Trp Gly Met Asp
                405                 410                 415
Ala Thr Gln Met Val Val Lys Ala Gly Pro Lys Gly Phe Trp His Cys
            420                 425                 430
Gln Pro Asp Asn Gly Thr Phe Glu Met Trp Phe Asn Gly Lys Asn Leu
        435                 440                 445
Phe Pro Asp Ser Gly Ser Tyr Val Tyr Ala Gly Glu Gly Glu Val Met
    450                 455                 460
Glu Gln Arg Asn Trp His Arg Gln Thr Ser Val His Asn Thr Val Thr
465                 470                 475                 480
Leu Asp Asn Lys Asn Leu Glu Thr Thr Glu Ser Val Thr Lys Leu Trp
                485                 490                 495
Gln Pro Glu Gly Asn Ile Gln Thr Leu Val Thr Glu Asn Pro Ser Tyr
            500                 505                 510
Lys Asn Phe Lys His Arg Arg Ser Val Phe Phe Val Asp Asn Thr Tyr
        515                 520                 525
Phe Val Ile Val Asp Glu Val Ser Gly Ser Ala Lys Gly Ser Val Asn
    530                 535                 540
Leu His Tyr Gln Met Pro Lys Gly Glu Ile Ala Asn Ser Arg Glu Asp
545                 550                 555                 560
Met Thr Phe Leu Thr Gln Phe Glu Asp Gly Ser Asn Met Lys Leu Gln
                565                 570                 575
Cys Phe Gly Pro Glu Gly Met Ser Met Lys Lys Glu Pro Gly Trp Cys
            580                 585                 590
Ser Thr Ala Tyr Arg Lys Arg Tyr Lys Arg Met Asn Val Ser Phe Asn
        595                 600                 605
Val Lys Lys Asp Asn Glu Asn Ala Val Arg Tyr Ile Thr Val Ile Tyr
    610                 615                 620
Pro Val Lys Lys Ser Ala Asp Ala Pro Lys Phe Asp Ala Lys Phe Lys
625                 630                 635                 640
Asn Lys Thr Phe Asp Glu Asn Gly Leu Glu Ile Glu Val Lys Val Asn
                645                 650                 655
Gly Lys Lys Gln Ser Leu Lys Tyr Lys Leu
            660                 665

<210> SEQ ID NO 7
<211> LENGTH: 1935
<212> TYPE: DNA
<213> ORGANISM: Bacteroides thetaiotaomicron
```

<400> SEQUENCE: 7

```
caagagttga aaagcgaggt attctcgctt ctcaacctgg actacccgg attggagaaa      60
gtaaaagcct tacatcagga aggcaaagat gaggatgccg caaaagcact gctcgactac    120
taccgtgcac gtacgaatgt gaagacgccg gatattaatc tgaaaaagat cactatcggc    180
aaagaagaac agcaatgggc ggatgacgga ttgaagcata cattctttgt tcacaaaggc    240
tatcagcctt cttacaacta cggagaagat atcaactggc aatactggcc ggtgaaagac    300
aatgaactcc gctggcagtt gcaccgtcat aaatggttta ctccgatggg taaggcatac    360
cgtgtatcgg gtgacgagaa atatgccaaa gaatgggcat accaatacat cgactggatt    420
aaaaagaatc cgttggtgaa gatggacaag aaagaatacg aactggtaag tgacggtaag    480
attaaaggcg aagtggaaaa tgtacgtttc gcatggcgtc cgctggaagt cagtaatcgt    540
ctgcaggatc agactaccca gttccagttg ttcctcccct ctccttcttt cactccggat    600
ttcctgactg aatttctggt gaactatcat aaacatgccg tacatattct ggctaattac    660
tctgatcagg gtaatcactt gttgttcgaa gcccagcgta tgatttatgc aggtgcattc    720
ttcccggaat ttaagaagc tccggcctgg agaaaaagcg gtatcgacat tctgaaccgt    780
gaagtaaacg tacaggttta caacgatggc ggccagtttg aacttgaccc gcattatcat    840
cttgctgcta tcaatatctt ctgcaaggca ttgggtatcg cggatgttaa cggattccgt    900
aatgagttcc cacaggaata tctggatact atcgaaaaga tgatcatgtt ctatgccaat    960
atttctttcc cggattacac aaatccgtgt ttcagtgatg ctaaaatcac agaaaagaaa   1020
gaaatgctga agaactatcg tgcatggagc aaactgttcc gaaaaacga actatcaag    1080
tatttggcaa cagacggcaa agaaggcgcg ttacccgatt atatgtcgaa aggtttcctg   1140
aaatcaggtt tctttgtgtt ccgcaattcc tggggaatgg atgctacaca aatggtagta   1200
aaagccggtc cgaaaggttt ctggcactgt cagccggata cggtactttt cgaaatgtgg   1260
tttaacggca agaacctgtt cccagactcc ggttcgtatg tgtatgccgg tgaaggcgaa   1320
gtgatggaac aacgcaactg gcatcgtcag acttccgtac acaacaccgt gactctggac   1380
aataagaatc tggaaacaac cgaatctgtt actaaactgt ggcagccgga aggcaatatc   1440
cagaccttgg ttacagaaaa cccaagctac aagaacttca agcaccgccg ttcggtcttc   1500
ttcgtagaca atacctactt tgtcattgta gatgaagtat caggcagcgc caaaggttct   1560
gtcaacctgc actatcagat gccgaaaggt gagatagcca cagccgtga agacatgaca   1620
ttcctgactc aattcgaaga tggaagcaac atgaaacttc aatgcttcgg ccctgaaggc   1680
atgagcatga aaaagagcc gggatggtgt tctactgcat atcgcaagcg ctacaaacgt   1740
atgaatgttt cattcaacgt aaagaaagac aatgagaatg cggtacgtta catcacagtt   1800
atttacccag tcaagaagag cgcagatgcc cctaaatttg acgctaagtt caagaacaaa   1860
acgttcgatg aaaacggact ggaaatagaa gtgaagtaa acgcaagaa acagtcatta   1920
aaatataaat tataa                                                     1935
```

<210> SEQ ID NO 8
<211> LENGTH: 644
<212> TYPE: PRT
<213> ORGANISM: Bacteroides thetaiotaomicron

<400> SEQUENCE: 8

```
Gln Glu Leu Lys Ser Glu Val Phe Ser Leu Leu Asn Leu Asp Tyr Pro
 1               5                  10                  15
```

-continued

```
Gly Leu Glu Lys Val Lys Ala Leu His Gln Glu Gly Lys Asp Glu Asp
         20                  25                  30
Ala Ala Lys Ala Leu Leu Asp Tyr Tyr Arg Ala Arg Thr Asn Val Lys
     35                  40                  45
Thr Pro Asp Ile Asn Leu Lys Lys Ile Thr Ile Gly Lys Glu Glu Gln
 50                  55                  60
Gln Trp Ala Asp Asp Gly Leu Lys His Thr Phe Phe Val His Lys Gly
 65                  70                  75                  80
Tyr Gln Pro Ser Tyr Asn Tyr Gly Glu Asp Ile Asn Trp Gln Tyr Trp
                 85                  90                  95
Pro Val Lys Asp Asn Glu Leu Arg Trp Gln Leu His Arg His Lys Trp
             100                 105                 110
Phe Thr Pro Met Gly Lys Ala Tyr Arg Val Ser Gly Asp Glu Lys Tyr
         115                 120                 125
Ala Lys Glu Trp Ala Tyr Gln Tyr Ile Asp Trp Ile Lys Lys Asn Pro
     130                 135                 140
Leu Val Lys Met Asp Lys Lys Glu Tyr Glu Leu Val Ser Asp Gly Lys
145                 150                 155                 160
Ile Lys Gly Glu Val Glu Asn Val Arg Phe Ala Trp Arg Pro Leu Glu
                165                 170                 175
Val Ser Asn Arg Leu Gln Asp Gln Thr Thr Gln Phe Gln Leu Phe Leu
            180                 185                 190
Pro Ser Pro Ser Phe Thr Pro Asp Phe Leu Thr Glu Phe Leu Val Asn
        195                 200                 205
Tyr His Lys His Ala Val His Ile Leu Ala Asn Tyr Ser Asp Gln Gly
    210                 215                 220
Asn His Leu Leu Phe Glu Ala Gln Arg Met Ile Tyr Ala Gly Ala Phe
225                 230                 235                 240
Phe Pro Glu Phe Lys Glu Ala Pro Ala Trp Arg Lys Ser Gly Ile Asp
                245                 250                 255
Ile Leu Asn Arg Glu Val Asn Val Gln Val Tyr Asn Asp Gly Gly Gln
            260                 265                 270
Phe Glu Leu Asp Pro His Tyr His Leu Ala Ala Ile Asn Ile Phe Cys
        275                 280                 285
Lys Ala Leu Gly Ile Ala Asp Val Asn Gly Phe Arg Asn Glu Phe Pro
    290                 295                 300
Gln Glu Tyr Leu Asp Thr Ile Glu Lys Met Ile Met Phe Tyr Ala Asn
305                 310                 315                 320
Ile Ser Phe Pro Asp Tyr Thr Asn Pro Cys Phe Ser Asp Ala Lys Ile
                325                 330                 335
Thr Glu Lys Lys Glu Met Leu Lys Asn Tyr Arg Ala Trp Ser Lys Leu
            340                 345                 350
Phe Pro Lys Asn Glu Thr Ile Lys Tyr Leu Ala Thr Asp Gly Lys Glu
        355                 360                 365
Gly Ala Leu Pro Asp Tyr Met Ser Lys Gly Phe Leu Lys Ser Gly Phe
    370                 375                 380
Phe Val Phe Arg Asn Ser Trp Gly Met Asp Ala Thr Gln Met Val Val
385                 390                 395                 400
Lys Ala Gly Pro Lys Gly Phe Trp His Cys Gln Pro Asp Asn Gly Thr
                405                 410                 415
Phe Glu Met Trp Phe Asn Gly Lys Asn Leu Phe Pro Asp Ser Gly Ser
            420                 425                 430
Tyr Val Tyr Ala Gly Glu Gly Glu Val Met Glu Gln Arg Asn Trp His
        435                 440                 445
```

```
Arg Gln Thr Ser Val His Asn Thr Val Thr Leu Asp Asn Lys Asn Leu
    450                 455                 460
Glu Thr Thr Glu Ser Val Thr Lys Leu Trp Gln Pro Glu Gly Asn Ile
465                 470                 475                 480
Gln Thr Leu Val Thr Glu Asn Pro Ser Tyr Lys Asn Phe Lys His Arg
                485                 490                 495
Arg Ser Val Phe Phe Val Asp Asn Thr Tyr Phe Val Ile Val Asp Glu
            500                 505                 510
Val Ser Gly Ser Ala Lys Gly Ser Val Asn Leu His Tyr Gln Met Pro
        515                 520                 525
Lys Gly Glu Ile Ala Asn Ser Arg Glu Asp Met Thr Phe Leu Thr Gln
    530                 535                 540
Phe Glu Asp Gly Ser Asn Met Lys Leu Gln Cys Phe Gly Pro Glu Gly
545                 550                 555                 560
Met Ser Met Lys Lys Glu Pro Gly Trp Cys Ser Thr Ala Tyr Arg Lys
                565                 570                 575
Arg Tyr Lys Arg Met Asn Val Ser Phe Asn Val Lys Lys Asp Asn Glu
            580                 585                 590
Asn Ala Val Arg Tyr Ile Thr Val Ile Tyr Pro Val Lys Lys Ser Ala
        595                 600                 605
Asp Ala Pro Lys Phe Asp Ala Lys Phe Lys Asn Lys Thr Phe Asp Glu
    610                 615                 620
Asn Gly Leu Glu Ile Glu Val Lys Val Asn Gly Lys Lys Gln Ser Leu
625                 630                 635                 640
Lys Tyr Lys Leu

<210> SEQ ID NO 9
<211> LENGTH: 1947
<212> TYPE: DNA
<213> ORGANISM: Bacteroides thetaiotaomicron

<400> SEQUENCE: 9
atgaataaaa ccctgaaata tatcgtcctg ctgacatttg cttgtttcgt aggcaaaggc     60
tatgcccaag agttgaaaag cgaggtattc tcgcttctca acctggacta ccccggattg    120
gagaaagtaa aagccttaca tcaggaaggc aaagatgagg atgccgcaaa agcactgctc    180
gactactacc gtgcacgtac gaatgtgaag acgccggata ttaatctgaa aaagatcact    240
atcggcaaag aagaacagca atgggcggat gacggattga agcatacatt ctttgttcac    300
aaaggctatc agccttctta caactacgga gaagatatca actggcaata ctggccggtg    360
aaagacaatg aactccgctg gcagttgcac cgtcataaat ggtttactcc gatgggtaag    420
gcataccgtg tatcgggtga cgagaaatat gccaaagaat gggcatacca atacatcgac    480
tggattaaaa agaatccgtt ggtggtggaa aatgtacgtt tcgcatggcg tccgctggaa    540
gtcagtaatc gtctgcagga tcagactacc cagttccagt tgttcctccc ctctccttct    600
ttcactccgg atttcctgac tgaatttctg gtgaactatc ataaacatgc cgtacatatt    660
ctggctaatt actctgatca gggtaatcac ttgttgttcg aagcccagcg tatgattat     720
gcaggtgcat tcttcccgga atttaaagaa gctccggcct ggagaaaaag cggtatcgac    780
attctgaacc gtgaagtaaa cgtacaggtt tacaacgatg cggcagtt tgaacttgac    840
ccgcattatc atcttgctgc tatcaatatc ttctgcaagg cattgggtat cgcggatgtt    900
aacggattcc gtaatgagtt cccacaggaa tatctggata ctatcgaaaa gatgatcatg    960
ttctatgcca atatttcttt cccggattac acaaatccgt gtttcagtga tgctaaaatc   1020
```

```
acagaaaaga aagaaatgct gaagaactat cgtgcatgga gcaaactgtt cccgaaaaac   1080
gaaactatca agtatttggc aacagacggc aaagaaggcg cgttacccga ttatatgtcg   1140

aaaggtttcc tgaaatcagg tttctttgtg ttccgcaatt cctggggaat ggatgctaca   1200
caaatggtag taaaagccgg tccgaaaggt ttctggcact gtcagccgga taacggtact   1260
ttcgaaatgt ggtttaacgg caagaacctg ttcccagact ccggttcgta tgtgtatgcc   1320
ggtgaaggcg aagtgatgga acaacgcaac tggcatcgtc agacttccgt acacaacacc   1380
gtgactctgg acaataagaa tctggaaaca accgaatctg ttactaaact gtggcagccg   1440
gaaggcaata tccagacctt ggttacagaa aacccaagct acaagaactt caagcaccgc   1500
cgttcggtct tcttcgtaga caatacctac tttgtcattg tagatgaagt atcaggcagc   1560
gccaaaggtt ctgtcaacct gcactatcag atgccgaaag gtgagatagc caacagccgt   1620
gaagacatga cattcctgac tcaattcgaa gatggaagca acatgaaact tcaatgcttc   1680
ggccctgaag gcatgagcat gaaaaaagag ccgggatggt gttctactgc atatcgcaag   1740
cgctacaaac gtatgaatgt ttcattcaac gtaaagaaag acaatgagaa tgcggtacgt   1800
tacatcacag ttatttaccc agtcaagaag agcgcagatg cccctaaatt tgacgctaag   1860
ttcaagaaca aaacgttcga tgaaaacgga ctggaaatag aagtgaaagt aaacggcaag   1920
aaacagtcat taaaatataa attataa                                       1947

<210> SEQ ID NO 10
<211> LENGTH: 649
<212> TYPE: PRT
<213> ORGANISM: Bacteroides thetaiotaomicron

<400> SEQUENCE: 10

Met Asn Lys Thr Leu Lys Tyr Ile Val Leu Leu Thr Phe Ala Cys Phe
 1               5                  10                  15

Val Gly Lys Gly Tyr Ala Gln Glu Leu Lys Ser Glu Val Phe Ser Leu
            20                  25                  30

Leu Asn Leu Asp Tyr Pro Gly Leu Glu Lys Val Lys Ala Leu His Gln
        35                  40                  45

Glu Gly Lys Asp Glu Asp Ala Ala Lys Ala Leu Leu Asp Tyr Tyr Arg
    50                  55                  60

Ala Arg Thr Asn Val Lys Thr Pro Asp Ile Asn Leu Lys Lys Ile Thr
65                  70                  75                  80

Ile Gly Lys Glu Glu Gln Gln Trp Ala Asp Asp Gly Leu Lys His Thr
                85                  90                  95

Phe Phe Val His Lys Gly Tyr Gln Pro Ser Tyr Asn Tyr Gly Glu Asp
            100                 105                 110

Ile Asn Trp Gln Tyr Trp Pro Val Lys Asp Asn Glu Leu Arg Trp Gln
        115                 120                 125

Leu His Arg His Lys Trp Phe Thr Pro Met Gly Lys Ala Tyr Arg Val
    130                 135                 140

Ser Gly Asp Glu Lys Tyr Ala Lys Glu Trp Ala Tyr Gln Tyr Ile Asp
145                 150                 155                 160

Trp Ile Lys Lys Asn Pro Leu Val Val Glu Asn Val Arg Phe Ala Trp
                165                 170                 175

Arg Pro Leu Glu Val Ser Asn Arg Leu Gln Asp Gln Thr Thr Gln Phe
            180                 185                 190

Gln Leu Phe Leu Pro Ser Pro Ser Phe Thr Pro Asp Phe Leu Thr Glu
        195                 200                 205
```

-continued

Phe Leu Val Asn Tyr His Lys His Ala Val His Ile Leu Ala Asn Tyr
            210                 215                 220

Ser Asp Gln Gly Asn His Leu Leu Phe Glu Ala Gln Arg Met Ile Tyr
225                 230                 235                 240

Ala Gly Ala Phe Phe Pro Glu Phe Lys Glu Ala Pro Ala Trp Arg Lys
            245                 250                 255

Ser Gly Ile Asp Ile Leu Asn Arg Glu Val Asn Val Gln Val Tyr Asn
            260                 265                 270

Asp Gly Gly Gln Phe Glu Leu Asp Pro His Tyr His Leu Ala Ala Ile
        275                 280                 285

Asn Ile Phe Cys Lys Ala Leu Gly Ile Ala Asp Val Asn Gly Phe Arg
290                 295                 300

Asn Glu Phe Pro Gln Glu Tyr Leu Asp Thr Ile Glu Lys Met Ile Met
305                 310                 315                 320

Phe Tyr Ala Asn Ile Ser Phe Pro Asp Tyr Thr Asn Pro Cys Phe Ser
                325                 330                 335

Asp Ala Lys Ile Thr Glu Lys Lys Glu Met Leu Lys Asn Tyr Arg Ala
                340                 345                 350

Trp Ser Lys Leu Phe Pro Lys Asn Glu Thr Ile Lys Tyr Leu Ala Thr
        355                 360                 365

Asp Gly Lys Glu Gly Ala Leu Pro Asp Tyr Met Ser Lys Gly Phe Leu
        370                 375                 380

Lys Ser Gly Phe Phe Val Phe Arg Asn Ser Trp Gly Met Asp Ala Thr
385                 390                 395                 400

Gln Met Val Val Lys Ala Gly Pro Lys Gly Phe Trp His Cys Gln Pro
                405                 410                 415

Asp Asn Gly Thr Phe Glu Met Trp Phe Asn Gly Lys Asn Leu Phe Pro
                420                 425                 430

Asp Ser Gly Ser Tyr Val Tyr Ala Gly Glu Gly Glu Val Met Glu Gln
        435                 440                 445

Arg Asn Trp His Arg Gln Thr Ser Val His Asn Thr Val Thr Leu Asp
    450                 455                 460

Asn Lys Asn Leu Glu Thr Thr Glu Ser Val Thr Lys Leu Trp Gln Pro
465                 470                 475                 480

Glu Gly Asn Ile Gln Thr Leu Val Thr Glu Asn Pro Ser Tyr Lys Asn
                485                 490                 495

Phe Lys His Arg Arg Ser Val Phe Val Asp Asn Thr Tyr Phe Val
                500                 505                 510

Ile Val Asp Glu Val Ser Gly Ser Ala Lys Gly Ser Val Asn Leu His
        515                 520                 525

Tyr Gln Met Pro Lys Gly Glu Ile Ala Asn Ser Arg Glu Asp Met Thr
    530                 535                 540

Phe Leu Thr Gln Phe Glu Asp Gly Ser Asn Met Lys Leu Gln Cys Phe
545                 550                 555                 560

Gly Pro Glu Gly Met Ser Met Lys Lys Glu Pro Gly Trp Cys Ser Thr
                565                 570                 575

Ala Tyr Arg Lys Arg Tyr Lys Arg Met Asn Val Ser Phe Asn Val Lys
                580                 585                 590

Lys Asp Asn Glu Asn Ala Val Arg Tyr Ile Thr Val Ile Tyr Pro Val
        595                 600                 605

Lys Lys Ser Ala Asp Ala Pro Lys Phe Asp Ala Lys Phe Lys Asn Lys
        610                 615                 620

Thr Phe Asp Glu Asn Gly Leu Glu Ile Glu Val Lys Val Asn Gly Lys
625                 630                 635                 640

Lys Gln Ser Leu Lys Tyr Lys Leu Leu
            645

<210> SEQ ID NO 11
<211> LENGTH: 29
<212> TYPE: DNA
<213> ORGANISM: Artificial Sequence
<220> FEATURE:
<223> OTHER INFORMATION: Primer

<400> SEQUENCE: 11
catatgctga ctgctcagac taaaaatac                              29

<210> SEQ ID NO 12
<211> LENGTH: 32
<212> TYPE: DNA
<213> ORGANISM: Artificial Sequence
<220> FEATURE:
<223> OTHER INFORMATION: Primer

<400> SEQUENCE: 12
ctcgagttat ctttccgaat atcctgcgag at                          32

<210> SEQ ID NO 13
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 13

Met Gly Ser Ser His His His His His His Ser Ser Gly Leu Val Pro
 1               5                  10                  15

Arg Gly Ser His
            20

<210> SEQ ID NO 14
<211> LENGTH: 33
<212> TYPE: DNA
<213> ORGANISM: Artificial Sequence
<220> FEATURE:
<223> OTHER INFORMATION: Primer

<400> SEQUENCE: 14
catatgaata aaaccctgaa atatatcgtc ctg                         33

<210> SEQ ID NO 15
<211> LENGTH: 38
<212> TYPE: DNA
<213> ORGANISM: Artificial Sequence
<220> FEATURE:
<223> OTHER INFORMATION: Primer

<400> SEQUENCE: 15
ctcgagttat aatttatatt ttaatgactg tttcttgc                    38

<210> SEQ ID NO 16
<211> LENGTH: 33
<212> TYPE: DNA
<213> ORGANISM: Artificial Sequence
<220> FEATURE:
<223> OTHER INFORMATION: Primer

<400> SEQUENCE: 16
catatgcaag agttgaaaag cgaggtattc tcg                         33

```
<210> SEQ ID NO 17
<211> LENGTH: 40
<212> TYPE: PRT
<213> ORGANISM: Artificial Sequence
<220> FEATURE:
<223> OTHER INFORMATION: Synthetically generated peptide

<400> SEQUENCE: 17

Met Gly Ser Ser His His His His His Ser Ser Gly Leu Val Pro
1               5                   10                  15

Arg Gly Ser His Met Asn Lys Thr Leu Lys Tyr Lys Val Asn Gly Lys
            20                  25                  30

Lys Gln Ser Leu Lys Tyr Lys Leu
        35                  40

<210> SEQ ID NO 18
<211> LENGTH: 42
<212> TYPE: PRT
<213> ORGANISM: Artificial Sequence
<220> FEATURE:
<223> OTHER INFORMATION: Synthetically generated peptide

<400> SEQUENCE: 18

Met Gly Ser Ser His His His His His Ser Ser Gly Leu Val Pro
1               5                   10                  15

Arg Gly Ser His Met Gln Glu Leu Lys Ser Glu Val Phe Lys Val Asn
            20                  25                  30

Gly Lys Lys Gln Ser Leu Lys Tyr Lys Leu
        35                  40

<210> SEQ ID NO 19
<211> LENGTH: 18
<212> TYPE: PRT
<213> ORGANISM: Bacteroides thetaiotaomicron

<400> SEQUENCE: 19

Lys Met Asp Lys Lys Glu Tyr Glu Leu Val Ser Asp Gly Lys Ile Lys
1               5                   10                  15

Gly Glu

<210> SEQ ID NO 20
<211> LENGTH: 40
<212> TYPE: DNA
<213> ORGANISM: Artificial Sequence
<220> FEATURE:
<223> OTHER INFORMATION: Primer

<400> SEQUENCE: 20
ggattaaaaa gaatccgttg gtggaaaatg tacgtttcgc                        40

<210> SEQ ID NO 21
<211> LENGTH: 40
<212> TYPE: DNA
<213> ORGANISM: Artificial Sequence
<220> FEATURE:
<223> OTHER INFORMATION: Primer

<400> SEQUENCE: 21
cctaattttt cttaggcaac cacctttac atgcaaagcg                         40

<210> SEQ ID NO 22
<211> LENGTH: 1104
<212> TYPE: DNA
<213> ORGANISM: Bacteroides thetaiotaomicron
```

<400> SEQUENCE: 22

```
caaacactga tgccactcac cgaacgggta aacgtacagg ctgactctgc acgtatcaac      60
cagattattg acggttgctg ggtagctgtc gggacgaata aacctcatgc cattcagcgt     120
gatttaccca acctgtttga tggcaagccc tcctatcgct ttgaactcaa aactgaagac    180
aatacactgg aaggttatgc gaaaggagaa acgaaaggac gtgccgagtt ttcatattgc    240
tatgcaactt ccgacgattt caggggatta cctgccgacg tttatcagaa agcacagatc    300
acaaagacag tttatcatca cgggaaggga gcttgtccgc aaggaagttc ccgcgactat    360
gagttttcgg tttatattcc ttcttcttta gacagcaatg tctccaccat ctttgcccaa    420
tggcacggaa tgcccgaccg gacgctggtc cagactcctc agggcgaggt gaagaaactg    480
actgttgacg aatttgtaga actggaaaaa acgaccttct tcaaaaagaa tgtcggacac    540
gaaaaagtgg ccagactgga taaacaaggt aatccggtga agataaaaa tggaaaaccct    600
gtatataagg caggaaaacc caacggatgg ttggttgaac agggaggata cccgccattg    660
gcattcggat tttccggagg actgtttat atcaaagcaa actccgaccg taaatggctg    720
acagacaaag atgaccgttg caatgcaaac ccgggaaaga cgcccgttat gaaaccgctg    780
acttctgaat acaaggcatc caccattgcc tacaaattac cttttgccga tttcccgaaa    840
gactgctgga ttacttttccg tgtccatatc gactggacgg tctatggcaa ggaagcggaa    900
acgattgtga aaccgggcat gctggatgta cggatggatt atcaggagca aggtaagaaa    960
gtgagcaaac acattgtcga taatgagaag attctgattg gacgtaacga cgaagacggg   1020
tattacttta agttcggaat ttaccgcgta ggtgatagta ccgttcccgt ttgctacaat   1080
ctcgcaggat attcggaaag ataa                                          1104
```

<210> SEQ ID NO 23
<211> LENGTH: 367
<212> TYPE: PRT
<213> ORGANISM: Bacteroides thetaiotaomicron

<400> SEQUENCE: 23

```
Gln Thr Leu Met Pro Leu Thr Glu Arg Val Asn Val Gln Ala Asp Ser
  1               5                  10                  15

Ala Arg Ile Asn Gln Ile Ile Asp Gly Cys Trp Val Ala Val Gly Thr
             20                  25                  30

Asn Lys Pro His Ala Ile Gln Arg Asp Phe Thr Asn Leu Phe Asp Gly
         35                  40                  45

Lys Pro Ser Tyr Arg Phe Glu Leu Lys Thr Glu Asp Asn Thr Leu Glu
     50                  55                  60

Gly Tyr Ala Lys Gly Glu Thr Lys Gly Arg Ala Glu Phe Ser Tyr Cys
 65                  70                  75                  80

Tyr Ala Thr Ser Asp Asp Phe Arg Gly Leu Pro Ala Asp Val Tyr Gln
                 85                  90                  95

Lys Ala Gln Ile Thr Lys Thr Val Tyr His His Gly Lys Gly Ala Cys
            100                 105                 110

Pro Gln Gly Ser Ser Arg Asp Tyr Glu Phe Ser Val Tyr Ile Pro Ser
        115                 120                 125

Ser Leu Asp Ser Asn Val Ser Thr Ile Phe Ala Gln Trp His Gly Met
    130                 135                 140

Pro Asp Arg Thr Leu Val Gln Thr Pro Gln Gly Glu Val Lys Lys Leu
145                 150                 155                 160

Thr Val Asp Glu Phe Val Glu Leu Glu Lys Thr Thr Phe Phe Lys Lys
```

```
                165                 170                 175
Asn Val Gly His Glu Lys Val Ala Arg Leu Asp Lys Gln Gly Asn Pro
            180                 185                 190
Val Lys Asp Lys Asn Gly Lys Pro Val Tyr Lys Ala Gly Lys Pro Asn
        195                 200                 205
Gly Trp Leu Val Glu Gln Gly Tyr Pro Pro Leu Ala Phe Gly Phe
    210                 215                 220
Ser Gly Gly Leu Phe Tyr Ile Lys Ala Asn Ser Asp Arg Lys Trp Leu
225                 230                 235                 240
Thr Asp Lys Asp Asp Arg Cys Asn Ala Asn Pro Gly Lys Thr Pro Val
                245                 250                 255
Met Lys Pro Leu Thr Ser Glu Tyr Lys Ala Ser Thr Ile Ala Tyr Lys
            260                 265                 270
Leu Pro Phe Ala Asp Phe Pro Lys Asp Cys Trp Ile Thr Phe Arg Val
        275                 280                 285
His Ile Asp Trp Thr Val Tyr Gly Lys Glu Ala Glu Thr Ile Val Lys
    290                 295                 300
Pro Gly Met Leu Asp Val Arg Met Asp Tyr Gln Glu Gln Gly Lys Lys
305                 310                 315                 320
Val Ser Lys His Ile Val Asp Asn Glu Lys Ile Leu Ile Gly Arg Asn
                325                 330                 335
Asp Glu Asp Gly Tyr Tyr Phe Lys Phe Gly Ile Tyr Arg Val Gly Asp
            340                 345                 350
Ser Thr Val Pro Val Cys Tyr Asn Leu Ala Gly Tyr Ser Glu Arg
        355                 360                 365

<210> SEQ ID NO 24
<211> LENGTH: 384
<212> TYPE: PRT
<213> ORGANISM: Pedobacter heparinus

<400> SEQUENCE: 24

Met Lys Lys Gln Ile Leu Tyr Leu Ile Val Leu Gln Gln Leu Phe Leu
1               5                   10                  15
Cys Ser Ala Tyr Ala Gln Gln Lys Lys Ser Gly Asn Ile Pro Tyr Arg
            20                  25                  30
Val Asn Val Gln Ala Asp Ser Ala Lys Gln Lys Ala Ile Ile Asp Asn
        35                  40                  45
Lys Trp Val Ala Val Gly Ile Asn Lys Pro Tyr Ala Leu Gln Tyr Asp
    50                  55                  60
Asp Lys Leu Arg Phe Asn Gly Lys Pro Ser Tyr Arg Phe Glu Leu Lys
65                  70                  75                  80
Ala Glu Asp Asn Ser Leu Glu Gly Tyr Ala Ala Gly Glu Thr Lys Gly
                85                  90                  95
Arg Thr Glu Leu Ser Tyr Ser Tyr Ala Thr Thr Asn Asp Phe Lys Lys
            100                 105                 110
Phe Pro Pro Ser Val Tyr Gln Asn Ala Gln Lys Leu Lys Thr Val Tyr
        115                 120                 125
His Tyr Gly Lys Gly Ile Cys Glu Gln Gly Ser Ser Arg Ser Tyr Thr
    130                 135                 140
Phe Ser Val Tyr Ile Pro Ser Ser Phe Pro Asp Asn Ala Thr Thr Ile
145                 150                 155                 160
Phe Ala Gln Trp His Gly Ala Pro Ser Arg Thr Leu Val Ala Thr Pro
                165                 170                 175
Glu Gly Glu Ile Lys Thr Leu Ser Ile Glu Glu Phe Leu Ala Leu Tyr
```

```
                180                 185                 190
Asp Arg Met Ile Phe Lys Lys Asn Ile Ala His Asp Lys Val Glu Lys
            195                 200                 205

Lys Asp Lys Asp Gly Lys Ile Thr Tyr Val Ala Gly Lys Pro Asn Gly
        210                 215                 220

Trp Lys Val Glu Gln Gly Gly Tyr Pro Thr Leu Ala Phe Gly Phe Ser
225                 230                 235                 240

Lys Gly Tyr Phe Tyr Ile Lys Ala Asn Ser Asp Arg Gln Trp Leu Thr
                245                 250                 255

Asp Lys Ala Asp Arg Asn Asn Ala Asn Pro Glu Asn Ser Glu Val Met
            260                 265                 270

Lys Pro Tyr Ser Ser Glu Tyr Lys Thr Ser Thr Ile Ala Tyr Lys Met
        275                 280                 285

Pro Phe Ala Gln Phe Pro Lys Asp Cys Trp Ile Thr Phe Asp Val Ala
    290                 295                 300

Ile Asp Trp Thr Lys Tyr Gly Lys Glu Ala Asn Thr Ile Leu Lys Pro
305                 310                 315                 320

Gly Lys Leu Asp Val Met Met Thr Tyr Thr Lys Asn Lys Lys Pro Gln
                325                 330                 335

Lys Ala His Ile Val Asn Gln Gln Glu Ile Leu Ile Gly Arg Asn Asp
            340                 345                 350

Asp Asp Gly Tyr Tyr Phe Lys Phe Gly Ile Tyr Arg Val Gly Asn Ser
        355                 360                 365

Thr Val Pro Val Thr Tyr Asn Leu Ser Gly Tyr Ser Glu Thr Ala Arg
    370                 375                 380

<210> SEQ ID NO 25
<211> LENGTH: 659
<212> TYPE: PRT
<213> ORGANISM: Pedobacter heparinus

<400> SEQUENCE: 25

Met Thr Thr Lys Ile Phe Lys Arg Ile Ile Val Phe Ala Val Ile Ala
1               5                   10                  15

Leu Ser Ser Gly Asn Ile Leu Ala Gln Ser Ser Ser Ile Thr Arg Lys
            20                  25                  30

Asp Phe Asp His Ile Asn Leu Glu Tyr Ser Gly Leu Glu Lys Val Asn
        35                  40                  45

Lys Ala Val Ala Ala Gly Asn Tyr Asp Asp Ala Lys Ala Leu Leu
    50                  55                  60

Ala Tyr Tyr Arg Glu Lys Ser Lys Ala Arg Glu Pro Asp Phe Ser Asn
65                  70                  75                  80

Ala Glu Lys Pro Ala Asp Ile Arg Gln Pro Ile Asp Lys Val Thr Arg
                85                  90                  95

Glu Met Ala Asp Lys Ala Leu Val His Gln Phe Gln Pro His Lys Gly
            100                 105                 110

Tyr Gly Tyr Phe Asp Tyr Gly Lys Asp Ile Asn Trp Gln Met Trp Pro
        115                 120                 125

Val Lys Asp Asn Glu Val Arg Trp Gln Leu His Arg Val Lys Trp Trp
    130                 135                 140

Gln Ala Met Ala Leu Val Tyr His Ala Thr Gly Asp Glu Lys Tyr Ala
145                 150                 155                 160

Arg Glu Trp Val Tyr Gln Tyr Ser Asp Trp Ala Arg Lys Asn Pro Leu
                165                 170                 175

Gly Leu Ser Gln Asp Asn Asp Lys Phe Val Trp Arg Pro Leu Glu Val
```

```
                    180                 185                 190
Ser Asp Arg Val Gln Ser Leu Pro Pro Thr Phe Ser Leu Phe Val Asn
                195                 200                 205

Ser Pro Ala Phe Thr Pro Ala Phe Leu Met Glu Phe Leu Asn Ser Tyr
            210                 215                 220

His Gln Gln Ala Asp Tyr Leu Ser Thr His Tyr Ala Glu Gln Gly Asn
225                 230                 235                 240

His Arg Leu Phe Glu Ala Gln Arg Asn Leu Phe Ala Gly Val Ser Phe
                245                 250                 255

Pro Glu Phe Lys Asp Ser Pro Arg Trp Arg Gln Thr Gly Ile Ser Val
            260                 265                 270

Leu Asn Thr Glu Ile Lys Lys Gln Val Tyr Ala Asp Gly Met Gln Phe
        275                 280                 285

Glu Leu Ser Pro Ile Tyr His Val Ala Ala Ile Asp Ile Phe Leu Lys
    290                 295                 300

Ala Tyr Gly Ser Ala Lys Arg Val Asn Leu Glu Lys Glu Phe Pro Gln
305                 310                 315                 320

Ser Tyr Val Gln Thr Val Glu Asn Met Ile Met Ala Leu Ile Ser Ile
                325                 330                 335

Ser Leu Pro Asp Tyr Asn Thr Pro Met Phe Gly Asp Ser Trp Ile Thr
            340                 345                 350

Asp Lys Asn Phe Arg Met Ala Gln Phe Ala Ser Trp Ala Arg Val Phe
        355                 360                 365

Pro Ala Asn Gln Ala Ile Lys Tyr Phe Ala Thr Asp Gly Lys Gln Gly
    370                 375                 380

Lys Ala Pro Asn Phe Leu Ser Lys Ala Leu Ser Asn Ala Gly Phe Tyr
385                 390                 395                 400

Thr Phe Arg Ser Gly Trp Asp Lys Asn Ala Thr Val Met Val Leu Lys
                405                 410                 415

Ala Ser Pro Pro Gly Glu Phe His Ala Gln Pro Asp Asn Gly Thr Phe
            420                 425                 430

Glu Leu Phe Ile Lys Gly Arg Asn Phe Thr Pro Asp Ala Gly Val Phe
        435                 440                 445

Val Tyr Ser Gly Asp Glu Ala Ile Met Lys Leu Arg Asn Trp Tyr Arg
    450                 455                 460

Gln Thr Arg Ile His Ser Thr Leu Thr Leu Asp Asn Gln Asn Met Val
465                 470                 475                 480

Ile Thr Lys Ala Arg Gln Asn Lys Trp Glu Thr Gly Asn Asn Leu Asp
                485                 490                 495

Val Leu Thr Tyr Thr Asn Pro Ser Tyr Pro Asn Leu Asp His Gln Arg
            500                 505                 510

Ser Val Leu Phe Ile Asn Lys Lys Tyr Phe Leu Val Ile Asp Arg Ala
        515                 520                 525

Ile Gly Glu Ala Thr Gly Asn Leu Gly Val His Trp Gln Leu Lys Glu
    530                 535                 540

Asp Ser Asn Pro Val Phe Asp Lys Thr Lys Asn Arg Val Tyr Thr Thr
545                 550                 555                 560

Tyr Arg Asp Gly Asn Asn Leu Met Ile Gln Ser Leu Asn Ala Asp Arg
                565                 570                 575

Thr Ser Leu Asn Glu Glu Gly Lys Val Ser Tyr Val Tyr Asn Lys
            580                 585                 590

Glu Leu Lys Arg Pro Ala Phe Val Phe Glu Lys Pro Lys Lys Asn Ala
        595                 600                 605
```

Gly Thr Gln Asn Phe Val Ser Ile Val Tyr Pro Tyr Asp Gly Gln Lys
            610                 615                 620

Ala Pro Glu Ile Ser Ile Arg Glu Asn Lys Gly Asn Asp Phe Glu Lys
625                 630                 635                 640

Gly Lys Leu Asn Leu Thr Leu Thr Ile Asn Gly Lys Gln Gln Leu Val
                645                 650                 655

Leu Val Pro

<210> SEQ ID NO 26
<211> LENGTH: 286
<212> TYPE: PRT
<213> ORGANISM: Artificial Sequence
<220> FEATURE:
<223> OTHER INFORMATION: Consensus sequence

<400> SEQUENCE: 26

Met Lys Lys Ile Leu Ile Met Met Gly Cys Arg Val Asn Val Gln Ala
1               5                   10                  15

Asp Ser Ala Arg Ile Ile Asp Trp Val Ala Gly Asn Lys Pro Ala
            20                  25                  30

Ile Gln Asp Phe Gly Lys Pro Ser Tyr Arg Phe Glu Leu Lys Glu Asp
            35                  40                  45

Asn Thr Leu Glu Gly Tyr Ala Gly Glu Thr Lys Gly Arg Glu Ser Tyr
50                  55                  60

Tyr Ala Thr Ser Asp Phe Arg Pro Val Tyr Gln Ala Gln Lys Thr Val
65                  70                  75                  80

Tyr His Gly Lys Gly Cys Gln Gly Ser Ser Arg Tyr Phe Ser Val Tyr
                85                  90                  95

Ile Pro Ser Ser Asn Ser Thr Ile Phe Ala Gln Trp His Gly Pro Arg
            100                 105                 110

Thr Leu Val Thr Pro Gly Glu Val Lys Leu Thr Val Asp Glu Phe Val
            115                 120                 125

Leu Phe Lys Lys Asn Val Gly His Glu Lys Val Arg Leu Asp Lys Gln
            130                 135                 140

Gly Asn Pro Val Lys Asp Lys Gly Lys Tyr Ala Gly Lys Pro Asn Gly
145                 150                 155                 160

Trp Val Glu Gln Gly Gly Tyr Pro Leu Ala Phe Gly Phe Ser Gly Phe
                165                 170                 175

Tyr Ile Lys Ala Asn Ser Asp Arg Trp Leu Thr Asp Lys Asp Arg Asn
            180                 185                 190

Ala Asn Pro Thr Val Met Lys Pro Thr Ser Glu Tyr Lys Ser Thr Ile
            195                 200                 205

Ala Tyr Lys Ile Pro Phe Ala Phe Pro Lys Asp Cys Trp Ile Thr Phe
210                 215                 220

Val Ile Asp Trp Thr Tyr Gly Lys Glu Ala Thr Ile Val Lys Pro Gly
225                 230                 235                 240

Leu Asp Val Met Tyr Gln Lys His Ile Val Asn Ile Leu Ile Gly Arg
                245                 250                 255

Asn Asp Glu Asp Gly Tyr Tyr Phe Lys Phe Gly Ile Tyr Arg Val Gly
            260                 265                 270

Ser Thr Val Pro Val Tyr Asn Leu Gly Tyr Ser Glu Ala Arg
            275                 280                 285

<210> SEQ ID NO 27
<211> LENGTH: 388
<212> TYPE: PRT
<213> ORGANISM: Artificial Sequence -continued

```
<220> FEATURE:
<223> OTHER INFORMATION: Consensus sequence

<400> SEQUENCE: 27

Met Lys Lys Ile Ile Val Gly Asn Ile Ala Ile Phe Ile Asn Leu Glu
1               5                   10                  15

Tyr Gly Leu Glu Lys Val Gly Asp Asp Ala Lys Ala Leu Leu Tyr
            20                  25                  30

Tyr Arg Lys Ser Arg Pro Asp Asn Ala Glu Lys Pro Ala Arg Ile Lys
            35                  40                  45

Ala Asp Ala Leu His Phe His Lys Gly Tyr Pro Phe Tyr Gly Asp Ile
    50                  55                  60

Asn Trp Gln Trp Pro Val Lys Asp Asn Glu Val Arg Trp Gln Leu His
65                  70                  75                  80

Arg Lys Trp Trp Met Ala Tyr Thr Gly Asp Glu Lys Tyr Ala Arg Glu
                    85                  90                  95

Trp Tyr Gln Tyr Asp Trp Arg Lys Asn Pro Leu Lys Lys Glu Tyr Glu
                100                 105                 110

Leu Val Ser Asp Gly Lys Ile Lys Gly Glu Val Asp Asn Lys Phe Trp
            115                 120                 125

Arg Pro Leu Glu Val Ser Arg Val Gln Phe Leu Phe Val Ser Pro Phe
130                 135                 140

Thr Pro Phe Leu Glu Phe Leu Tyr His Ala Leu Tyr Glu Gln Gly Asn
145                 150                 155                 160

His Leu Phe Glu Ala Gln Arg Leu Phe Ala Gly Phe Pro Glu Phe Lys
                    165                 170                 175

Asp Pro Trp Arg Thr Gly Ile Val Leu Asn Glu Ile Gln Val Tyr Asp
                180                 185                 190

Gly Gln Phe Glu Leu Pro Tyr His Val Ala Ala Ile Ile Phe Lys Ala
            195                 200                 205

Gly Ala Glu Phe Pro Gln Tyr Val Thr Val Glu Met Ile Met Ile Ser
    210                 215                 220

Pro Asp Tyr Pro Phe Asp Ile Thr Asp Lys Met Gln Phe Trp Arg Val
225                 230                 235                 240

Phe Pro Asn Ile Lys Tyr Ala Thr Asp Gly Lys Gly Pro Phe Leu Ser
                    245                 250                 255

Lys Ala Gly Phe Tyr Phe Arg Trp Ala Thr Met Val Ile Lys Ala Pro
                260                 265                 270

Gly Phe His Gln Pro Asp Asn Gly Thr Phe Glu Leu Phe Gly Arg Asn
            275                 280                 285

Pro Asp Gly Phe Val Tyr Gly Asp Ile Met Arg Asn Trp Arg Gln Thr
    290                 295                 300

Ile His Thr Ile Thr Leu Asp Asn Asn Met Thr Trp Asn Leu Leu Asn
305                 310                 315                 320

Pro Ser Tyr Asn His Arg Ser Val Phe Ile Tyr Phe Leu Val Ile Asp
                    325                 330                 335

Gly Ala Gly Leu Val His Trp Gln Leu Asp Lys Thr Tyr Asp Gly Asn
                340                 345                 350

Leu Ile Gln Asp Ser Leu Glu Gly Ser Tyr Lys Lys Arg Phe Lys Asn
            355                 360                 365

Phe Val Ser Ile Val Tyr Pro Lys Phe Glu Leu Leu Ile Asn Gly
    370                 375                 380

Lys Gln Val Leu
385
```

<210> SEQ ID NO 28
<211> LENGTH: 2622
<212> TYPE: DNA
<213> ORGANISM: Bacteroides thetaiotaomicron

<400> SEQUENCE: 28

| | | | | | |
|---|---|---|---|---|---|
| atgatgaaac | aacgatatta | tattttcctg | ttatttgtag | ctatgctttc | ctatagtgga | 60 |
| tatgcgcaga | aaagcatcct | gcgtctgagt | cagcagacgc | tgatgcatga | agtccgcgaa | 120 |
| acaccttctc | cactgggcgg | tcagcacata | gcagtcaatc | cgccgcgttt | catgtggccg | 180 |
| gataagttcc | cccacctcgg | acctgtgctt | gacggagtgg | aagaagaaga | tcacaaaccg | 240 |
| gaagtgacat | accgcatccg | tatcgcacgt | gatcctgagt | ttaaatcgga | agtaatgacc | 300 |
| gccgaaagaa | actgggcttt | cttcaatcct | ttcaaactct | tgaaaaaagg | gaaatggtat | 360 |
| tggcagcacg | cctaccttga | taaggacggc | aaagaagaat | ggtcgcccgt | ctatcatttc | 420 |
| tatgtggacg | agcagacacg | tacgttcaat | cctccctcct | tgcaagaagt | gctggcgaag | 480 |
| ttctctcaaa | gccatcccg | tatcctgctc | gatgccaaag | actgggatca | gatcatcgag | 540 |
| cggaacaaga | ataatccgga | agcgcagctc | tatattcaga | aagcaaggaa | atgcctcaat | 600 |
| catccattga | aacatctgga | ggaggaaatc | gataccaccc | aagtagtcaa | attgacgaac | 660 |
| atcgtacaat | atcgctcggc | attgattcgg | gaaagccgca | agatagtaga | ccgcgaagaa | 720 |
| gcgaacatag | aagctatggt | acgcgcttat | ctgctgacga | agacgaagt | gtactacaaa | 780 |
| gaaggtatca | aacgtctttc | cgaaattctt | tcgtggaaag | acagtaagta | cttcgcagga | 840 |
| gatttcaacc | gctccacgat | tctgtccatg | agtacttccg | cttatgatgc | atggtacaat | 900 |
| ctgttaacgc | ctgccgagaa | acagttgctt | ctcgaaacga | tcagcgaaaa | cgcccataag | 960 |
| ttttatcatg | aatatgtgaa | tcatctggaa | aaccgtattg | ccgacaatca | tgtatggcag | 1020 |
| atgactttcc | gtattctgaa | tatggcagct | tttgctacat | acggtgaatt | gccgatggct | 1080 |
| tccacttggg | tagattattg | ctataacgaa | tgggtatccc | gtctgccggg | actcaacacc | 1140 |
| gacggaggat | ggcacaacgg | tgactcttat | ttccatgtca | accttcgtac | attgatcgaa | 1200 |
| gttcccgctt | tctattcacg | tatcagcggt | ttcgatttct | tgccgatcc | ctggtataac | 1260 |
| aacaatgcgc | tctatgtaat | ctatcatcag | cctccgttct | ccaaatctgc | gggacacggc | 1320 |
| aactcccatg | aaacgaaaat | gaaaccgaac | gggacacggg | tcggctatgc | ggatgcttta | 1380 |
| gcacgtgaat | gcaataatcc | gtgggcagcc | gcctacgcac | gtaccattct | ggagaaagaa | 1440 |
| ccggatatca | tgaaaaagtc | ttttcttgga | aaagcaggtg | atctgacctg | gtatcgctgc | 1500 |
| attactgaca | aggcactccc | gaaagaagaa | cactcattgg | cagagttgcc | gatgacgaaa | 1560 |
| gtatttaatg | aaacgggaat | tgctacgatg | catacttcgt | tgggggatat | agaaaagaac | 1620 |
| acaatgttgt | cattccgttc | cagtccatac | ggttcaactt | cgcacgcatt | ggccaatcag | 1680 |
| aatgcattta | ataccttcta | tggaggcaag | gcgatcttct | atagcagcgg | acatcgtacc | 1740 |
| ggttttaccg | atgaccattg | tatgtattcc | tatcgaaaca | cccgtgcgca | caatagtatt | 1800 |
| ctggtcaacg | gaatgactca | gactatagga | acgaaggtt | acggatggat | tccccgttgg | 1860 |
| tatgaaggag | aaaagatttc | gtatatggtg | ggagacgctt | ccaatgctta | cggaaagatc | 1920 |
| acagctccta | tctggttgaa | acgtggtgaa | ctttccggca | cgcagtacac | tcccgaaaag | 1980 |
| ggatgggatg | agaacaaact | gaagatgttc | cgtcggcaca | tcattcaatt | aggcaatacg | 2040 |
| ggagtgtatg | tgatttatga | tgaactggaa | ggaaaagaag | cggtcacatg | gagctatctg | 2100 |
| ctgcatacgg | tagaacttcc | gatggaaatg | caggaacttc | ctgatgaagt | gaaagttacg | 2160 |

-continued

```
ggaaagaata aggatggagg catctctgtt gctcatcttt tcagttcggc aaagacggaa    2220
caggccatcg tagataccttt cttctgcgct ccaaccaact ggaagaatgt aaccaatgcc    2280
caaggaaaag ctgtgaagta tcccaatcac tggcattttt cgtctactac cattccatgt    2340
aaaactgccc gtttcctcac cgttatggat acacatggaa ataaccgtgc ggatatgaaa    2400
gtggttcgcc aaggcaatac cgtacaagta ggcgactgga ttattacctg caatctgacg    2460
gagaaaggga agcggcaat cagcgtcacc catcaagcgg aaaaggtttc tttgaaatac    2520
gatgccggca agaaggaagg tgcgactatc atcacagatc aagtacaagg gaaacaggtc    2580
aataaggttc tgactgacta tttaccggat tttgagatat aa                      2622
```

<210> SEQ ID NO 29
<211> LENGTH: 872
<212> TYPE: PRT
<213> ORGANISM: Bacteroides thetaiotaomicron

<400> SEQUENCE: 29

```
Met Lys Gln Arg Tyr Tyr Ile Phe Leu Leu Phe Val Ala Met Leu Ser
  1               5                  10                  15

Tyr Ser Gly Tyr Ala Gln Lys Ser Ile Leu Arg Leu Ser Gln Gln Thr
             20                  25                  30

Leu Met His Glu Val Arg Glu Thr Pro Ser Pro Leu Gly Gly Gln His
         35                  40                  45

Ile Ala Val Asn Pro Pro Arg Phe Met Trp Pro Asp Lys Phe Pro His
     50                  55                  60

Leu Gly Pro Val Leu Asp Gly Val Glu Glu Asp His Lys Pro Glu
 65                  70                  75                  80

Val Thr Tyr Arg Ile Arg Ile Ala Arg Asp Pro Glu Phe Lys Ser Glu
                 85                  90                  95

Val Met Thr Ala Glu Arg Asn Trp Ala Phe Phe Asn Pro Phe Lys Leu
            100                 105                 110

Phe Glu Lys Gly Lys Trp Tyr Trp Gln His Ala Tyr Leu Asp Lys Asp
        115                 120                 125

Gly Lys Glu Glu Trp Ser Pro Val Tyr His Phe Tyr Val Asp Glu Gln
    130                 135                 140

Thr Arg Thr Phe Asn Pro Pro Ser Leu Gln Glu Val Leu Ala Lys Phe
145                 150                 155                 160

Ser Gln Ser His Pro Arg Ile Leu Leu Asp Ala Lys Asp Trp Asp Gln
                165                 170                 175

Ile Ile Glu Arg Asn Lys Asn Asn Pro Glu Ala Gln Leu Tyr Ile Gln
            180                 185                 190

Lys Ala Arg Lys Cys Leu Asn His Pro Leu Lys His Leu Glu Glu Glu
        195                 200                 205

Ile Asp Thr Thr Gln Val Val Lys Leu Thr Asn Ile Val Gln Tyr Arg
    210                 215                 220

Ser Ala Leu Ile Arg Glu Ser Arg Lys Ile Val Asp Arg Glu Glu Ala
225                 230                 235                 240

Asn Ile Glu Ala Met Val Arg Ala Tyr Leu Leu Thr Lys Asp Glu Val
                245                 250                 255

Tyr Tyr Lys Glu Gly Ile Lys Arg Leu Ser Glu Ile Leu Ser Trp Lys
            260                 265                 270

Asp Ser Lys Tyr Phe Ala Gly Asp Phe Asn Arg Ser Thr Ile Leu Ser
        275                 280                 285

Met Ser Thr Ser Ala Tyr Asp Ala Trp Tyr Asn Leu Leu Thr Pro Ala
    290                 295                 300
```

```
Glu Lys Gln Leu Leu Leu Glu Thr Ile Ser Glu Asn Ala His Lys Phe
305                 310                 315                 320

Tyr His Glu Tyr Val Asn His Leu Glu Asn Arg Ile Ala Asp Asn His
                325                 330                 335

Val Trp Gln Met Thr Phe Arg Ile Leu Asn Met Ala Ala Phe Ala Thr
                340                 345                 350

Tyr Gly Glu Leu Pro Met Ala Ser Thr Trp Val Asp Tyr Cys Tyr Asn
                355                 360                 365

Glu Trp Val Ser Arg Leu Pro Gly Leu Asn Thr Asp Gly Gly Trp His
370                 375                 380

Asn Gly Asp Ser Tyr Phe His Val Asn Leu Arg Thr Leu Ile Glu Val
385                 390                 395                 400

Pro Ala Phe Tyr Ser Arg Ile Ser Gly Phe Asp Phe Ala Asp Pro
                405                 410                 415

Trp Tyr Asn Asn Asn Ala Leu Tyr Val Ile Tyr His Gln Pro Pro Phe
                420                 425                 430

Ser Lys Ser Ala Gly His Gly Asn Ser His Glu Thr Lys Met Lys Pro
                435                 440                 445

Asn Gly Thr Arg Val Gly Tyr Ala Asp Ala Leu Ala Arg Glu Cys Asn
450                 455                 460

Asn Pro Trp Ala Ala Tyr Ala Arg Thr Ile Leu Glu Lys Glu Pro
465                 470                 475                 480

Asp Ile Met Lys Lys Ser Phe Leu Gly Lys Ala Gly Asp Leu Thr Trp
                485                 490                 495

Tyr Arg Cys Ile Thr Asp Lys Ala Leu Pro Lys Glu Glu His Ser Leu
                500                 505                 510

Ala Glu Leu Pro Met Thr Lys Val Phe Asn Glu Thr Gly Ile Ala Thr
                515                 520                 525

Met His Thr Ser Leu Gly Asp Ile Glu Lys Asn Thr Met Leu Ser Phe
530                 535                 540

Arg Ser Ser Pro Tyr Gly Ser Thr Ser His Ala Leu Ala Asn Gln Asn
545                 550                 555                 560

Ala Phe Asn Thr Phe Tyr Gly Gly Lys Ala Ile Phe Tyr Ser Ser Gly
                565                 570                 575

His Arg Thr Gly Phe Thr Asp Asp His Cys Met Tyr Ser Tyr Arg Asn
                580                 585                 590

Thr Arg Ala His Asn Ser Ile Leu Val Asn Gly Met Thr Gln Thr Ile
                595                 600                 605

Gly Thr Glu Gly Tyr Gly Trp Ile Pro Arg Trp Tyr Glu Gly Glu Lys
610                 615                 620

Ile Ser Tyr Met Val Gly Asp Ala Ser Asn Ala Tyr Gly Lys Ile Thr
625                 630                 635                 640

Ala Pro Ile Trp Leu Lys Arg Gly Glu Leu Ser Gly Thr Gln Tyr Thr
                645                 650                 655

Pro Glu Lys Gly Trp Asp Glu Asn Lys Leu Lys Met Phe Arg Arg His
                660                 665                 670

Ile Ile Gln Leu Gly Asn Thr Gly Val Tyr Val Ile Tyr Asp Glu Leu
                675                 680                 685

Glu Gly Lys Glu Ala Val Thr Trp Ser Tyr Leu Leu His Thr Val Glu
                690                 695                 700

Leu Pro Met Glu Met Gln Glu Leu Pro Asp Glu Val Lys Val Thr Gly
705                 710                 715                 720

Lys Asn Lys Asp Gly Gly Ile Ser Val Ala His Leu Phe Ser Ser Ala
```

```
                725                 730                 735
Lys Thr Glu Gln Ala Ile Val Asp Thr Phe Phe Cys Ala Pro Thr Asn
                    740                 745                 750

Trp Lys Asn Val Thr Asn Ala Gln Gly Lys Ala Val Lys Tyr Pro Asn
                755                 760                 765

His Trp His Phe Ser Ser Thr Thr Ile Pro Cys Lys Thr Ala Arg Phe
        770                 775                 780

Leu Thr Val Met Asp Thr His Gly Asn Asn Arg Ala Asp Met Lys Val
785                 790                 795                 800

Val Arg Gln Gly Asn Thr Val Gln Val Gly Asp Trp Ile Ile Thr Cys
                805                 810                 815

Asn Leu Thr Glu Lys Gly Lys Ala Ala Ile Ser Val Thr His Gln Ala
            820                 825                 830

Glu Lys Val Ser Leu Lys Tyr Asp Ala Gly Lys Lys Glu Gly Ala Thr
        835                 840                 845

Ile Ile Thr Asp Gln Val Gln Gly Lys Gln Val Asn Lys Val Leu Thr
    850                 855                 860

Asp Tyr Leu Pro Asp Phe Glu Ile
865                 870

<210> SEQ ID NO 30
<211> LENGTH: 30
<212> TYPE: DNA
<213> ORGANISM: Artificial Sequence
<220> FEATURE:
<223> OTHER INFORMATION: Primer

<400> SEQUENCE: 30
catatgatga acaacgata ttatattttc                                        30

<210> SEQ ID NO 31
<211> LENGTH: 38
<212> TYPE: DNA
<213> ORGANISM: Artificial Sequence
<220> FEATURE:
<223> OTHER INFORMATION: Primer

<400> SEQUENCE: 31
ggatcctcga gttatatctc aaaatccggt aaatagtc                              38

<210> SEQ ID NO 32
<211> LENGTH: 33
<212> TYPE: DNA
<213> ORGANISM: Artificial Sequence
<220> FEATURE:
<223> OTHER INFORMATION: Primer

<400> SEQUENCE: 32
ccatggcata tgaagaacat cttctttatt tgc                                   33

<210> SEQ ID NO 33
<211> LENGTH: 2556
<212> TYPE: DNA
<213> ORGANISM: Bacteroides thetaiotaomicron

<400> SEQUENCE: 33
cagaaaagca tcctgcgtct gagtcagcag acgctgatgc atgaagtccg cgaaacacct     60
tctccactgg gcggtcagca catagcagtc aatccgccgc gtttcatgtg gccggataag    120
ttcccccacc tcggacctgt gcttgacgga gtggaagaag aagatcacaa accggaagtg    180
acataccgca tccgtatcgc acgtgatcct gagtttaaat cggaagtaat gaccgccgaa    240
```

```
agaaactggg ctttcttcaa tcctttcaaa ctctttgaaa aagggaaatg gtattggcag    300
cacgcctacc ttgataagga cggcaaagaa gaatggtcgc ccgtctatca tttctatgtg    360
gacgagcaga cacgtacgtt caatcctccc tccttgcaag aagtgctggc gaagttctct    420
caaagccatc cccgtatcct gctcgatgcc aaagactggg atcagatcat cgagcggaac    480
aagaataatc cggaagcgca gctctatatt cagaaagcaa ggaaatgcct caatcatcca    540
ttgaaacatc tggaggagga aatcgatacc acccaagtag tcaaattgac gaacatcgta    600
caatatcgct cggcattgat tcgggaaagc cgcaagatag tagaccgcga agaagcgaac    660
atagaagcta tggtacgcgc ttatctgctg acgaaagacg aagtgtacta caaagaaggt    720
atcaaacgtc tttccgaaat tctttcgtgg aaagacagta agtacttcgc aggagatttc    780
aaccgctcca cgattctgtc catgagtact tccgcttatg atgcatggta caatctgtta    840
acgcctgccg agaaacagtt gcttctcgaa acgatcagcg aaaacgccca taagttttat    900
catgaatatg tgaatcatct ggaaaaccgt attgccgaca atcatgtatg gcagatgact    960
ttccgtattc tgaatatggc agcttttgct acatacggtg aattgccgat ggcttccact   1020
tgggtagatt attgctataa cgaatgggta tcccgtctgc cgggactcaa caccgacgga   1080
ggatggcaca acggtgactc ttatttccat gtcaaccttc gtacattgat cgaagttccc   1140
gctttctatt cacgtatcag cggtttcgat ttctttgccg atccctggta taacaacaat   1200
gcgctctatg taatctatca tcagcctccg ttctccaaat ctgcgggaca cggcaactcc   1260
catgaaacga aaatgaaacc gaacgggaca cgggtcggct atgcggatgc tttagcacgt   1320
gaatgcaata atccgtgggc agccgcctac gcacgtacca ttctggagaa agaaccggat   1380
atcatgaaaa agtctttctct tggaaaagca ggtgatctga cctggtatcg ctgcattact   1440
gacaaggcac tcccgaaaga agaacactca ttggcagagt tgccgatgac gaaagtattt   1500
aatgaaacgg gaattgctac gatgcatact tcgttggggg atatagaaaa gaacacaatg   1560
ttgtcattcc gttccagtcc atacggttca acttcgcacg cattggccaa tcagaatgca   1620
tttaatacct tctatggagg caaggcgatc ttctatagca gcggacatcg taccggtttt   1680
accgatgacc attgtatgta ttcctatcga aacacccgtg cgcacaatag tattctggtc   1740
aacggaatga ctcagactat aggaacggaa ggttacggat ggattccccg ttggtatgaa   1800
ggagaaaaga tttcgtatat ggtgggagac gcttccaatg cttacggaaa gatcacagct   1860
cctatctggt tgaaacgtgg tgaacttttcc ggcacgcagt acactcccga aaagggatgg   1920
gatgagaaca aactgaagat gttccgtcgg cacatcattc aattaggcaa tacgggagtg   1980
tatgtgattt atgatgaact ggaaggaaaa gaagcggtca catggagcta tctgctgcat   2040
acggtagaac ttccgatgga aatgcaggaa cttcctgatg aagtgaaagt tacgggaaag   2100
aataaggatg gaggcatctc tgttgctcat cttttcagtt cggcaaagac ggaacaggcc   2160
atcgtagata ccttcttctg cgctccaacc aactggaaga atgtaaccaa tgcccaagga   2220
aaagctgtga agtatcccaa tcactggcat ttttcgtcta ctaccattcc atgtaaaact   2280
gcccgttttcc tcaccgttat ggatacacat ggaaataacc gtgcggatat gaagtggtt    2340
cgccaaggca ataccgtaca agtaggcgac tggattatta cctgcaatct gacggagaaa   2400
gggaaagcgg caatcagcgt cacccatcaa gcggaaaagg tttctttgaa atacgatgcc   2460
ggcaagaagg aaggtgcgac tatcatcaca gatcaagtac aagggaaaca ggtcaataag   2520
gttctgactg actatttacc ggattttgag atataa                             2556
```

```
<210> SEQ ID NO 34
<211> LENGTH: 851
<212> TYPE: PRT
<213> ORGANISM: Bacteroides thetaiotaomicron

<400> SEQUENCE: 34

Gln Lys Ser Ile Leu Arg Leu Ser Gln Gln Thr Leu Met His Glu Val
  1               5                  10                  15

Arg Glu Thr Pro Ser Pro Leu Gly Gly Gln His Ile Ala Val Asn Pro
                 20                  25                  30

Pro Arg Phe Met Trp Pro Asp Lys Phe Pro His Leu Gly Pro Val Leu
             35                  40                  45

Asp Gly Val Glu Glu Asp His Lys Pro Glu Val Thr Tyr Arg Ile
 50                  55                  60

Arg Ile Ala Arg Asp Pro Glu Phe Lys Ser Glu Val Met Thr Ala Glu
 65                  70                  75                  80

Arg Asn Trp Ala Phe Phe Asn Pro Phe Lys Leu Phe Glu Lys Gly Lys
                 85                  90                  95

Trp Tyr Trp Gln His Ala Tyr Leu Asp Lys Asp Gly Lys Glu Glu Trp
            100                 105                 110

Ser Pro Val Tyr His Phe Tyr Val Asp Glu Gln Thr Arg Thr Phe Asn
            115                 120                 125

Pro Pro Ser Leu Gln Glu Val Leu Ala Lys Phe Ser Gln Ser His Pro
        130                 135                 140

Arg Ile Leu Leu Asp Ala Lys Asp Trp Asp Gln Ile Ile Glu Arg Asn
145                 150                 155                 160

Lys Asn Asn Pro Glu Ala Gln Leu Tyr Ile Gln Lys Ala Arg Lys Cys
                165                 170                 175

Leu Asn His Pro Leu Lys His Leu Glu Glu Ile Asp Thr Thr Gln
            180                 185                 190

Val Val Lys Leu Thr Asn Ile Val Gln Tyr Arg Ser Ala Leu Ile Arg
        195                 200                 205

Glu Ser Arg Lys Ile Val Asp Arg Glu Glu Ala Asn Ile Glu Ala Met
    210                 215                 220

Val Arg Ala Tyr Leu Leu Thr Lys Asp Glu Val Tyr Tyr Lys Glu Gly
225                 230                 235                 240

Ile Lys Arg Leu Ser Glu Ile Leu Ser Trp Lys Asp Ser Lys Tyr Phe
                245                 250                 255

Ala Gly Asp Phe Asn Arg Ser Thr Ile Leu Ser Met Ser Thr Ser Ala
            260                 265                 270

Tyr Asp Ala Trp Tyr Asn Leu Leu Thr Pro Ala Glu Lys Gln Leu Leu
        275                 280                 285

Leu Glu Thr Ile Ser Glu Asn Ala His Lys Phe Tyr His Glu Tyr Val
    290                 295                 300

Asn His Leu Glu Asn Arg Ile Ala Asp Asn His Val Trp Gln Met Thr
305                 310                 315                 320

Phe Arg Ile Leu Asn Met Ala Ala Phe Ala Thr Tyr Gly Glu Leu Pro
                325                 330                 335

Met Ala Ser Thr Trp Val Asp Tyr Cys Tyr Asn Glu Trp Val Ser Arg
            340                 345                 350

Leu Pro Gly Leu Asn Thr Asp Gly Gly Trp His Asn Gly Asp Ser Tyr
        355                 360                 365

Phe His Val Asn Leu Arg Thr Leu Ile Glu Val Pro Ala Phe Tyr Ser
    370                 375                 380

Arg Ile Ser Gly Phe Asp Phe Phe Ala Asp Pro Trp Tyr Asn Asn Asn
```

```
                385                 390                 395                 400
Ala Leu Tyr Val Ile Tyr His Gln Pro Pro Phe Ser Lys Ser Ala Gly
                    405                 410                 415

His Gly Asn Ser His Glu Thr Lys Met Lys Pro Asn Gly Thr Arg Val
                420                 425                 430

Gly Tyr Ala Asp Ala Leu Ala Arg Glu Cys Asn Asn Pro Trp Ala Ala
            435                 440                 445

Ala Tyr Ala Arg Thr Ile Leu Glu Lys Glu Pro Asp Ile Met Lys Lys
        450                 455                 460

Ser Phe Leu Gly Lys Ala Gly Asp Leu Thr Trp Tyr Arg Cys Ile Thr
465                 470                 475                 480

Asp Lys Ala Leu Pro Lys Glu His Ser Leu Ala Glu Leu Pro Met
                    485                 490                 495

Thr Lys Val Phe Asn Glu Thr Gly Ile Ala Thr Met His Thr Ser Leu
                500                 505                 510

Gly Asp Ile Glu Lys Asn Thr Met Leu Ser Phe Arg Ser Ser Pro Tyr
            515                 520                 525

Gly Ser Thr Ser His Ala Leu Ala Asn Gln Asn Ala Phe Asn Thr Phe
        530                 535                 540

Tyr Gly Gly Lys Ala Ile Phe Tyr Ser Ser Gly His Arg Thr Gly Phe
545                 550                 555                 560

Thr Asp Asp His Cys Met Tyr Ser Tyr Arg Asn Thr Arg Ala His Asn
                    565                 570                 575

Ser Ile Leu Val Asn Gly Met Thr Gln Thr Ile Gly Thr Glu Gly Tyr
                580                 585                 590

Gly Trp Ile Pro Arg Trp Tyr Glu Gly Glu Lys Ile Ser Tyr Met Val
            595                 600                 605

Gly Asp Ala Ser Asn Ala Tyr Gly Lys Ile Thr Ala Pro Ile Trp Leu
        610                 615                 620

Lys Arg Gly Glu Leu Ser Gly Thr Gln Tyr Thr Pro Glu Lys Gly Trp
625                 630                 635                 640

Asp Glu Asn Lys Leu Lys Met Phe Arg Arg His Ile Ile Gln Leu Gly
                    645                 650                 655

Asn Thr Gly Val Tyr Val Ile Tyr Asp Glu Leu Glu Gly Lys Glu Ala
                660                 665                 670

Val Thr Trp Ser Tyr Leu Leu His Thr Val Glu Leu Pro Met Glu Met
            675                 680                 685

Gln Glu Leu Pro Asp Glu Val Lys Val Thr Gly Lys Asn Lys Asp Gly
        690                 695                 700

Gly Ile Ser Val Ala His Leu Phe Ser Ser Ala Lys Thr Glu Gln Ala
705                 710                 715                 720

Ile Val Asp Thr Phe Phe Cys Ala Pro Thr Asn Trp Lys Asn Val Thr
                    725                 730                 735

Asn Ala Gln Gly Lys Ala Val Lys Tyr Pro Asn His Trp Phe Ser
                740                 745                 750

Ser Thr Thr Ile Pro Cys Lys Thr Ala Arg Phe Leu Thr Val Met Asp
            755                 760                 765

Thr His Gly Asn Asn Arg Ala Asp Met Lys Val Val Arg Gln Gly Asn
        770                 775                 780

Thr Val Gln Val Gly Asp Trp Ile Ile Thr Cys Asn Leu Thr Glu Lys
785                 790                 795                 800

Gly Lys Ala Ala Ile Ser Val Thr His Gln Ala Glu Lys Val Ser Leu
                    805                 810                 815
```

```
        Lys Tyr Asp Ala Gly Lys Lys Glu Gly Ala Thr Ile Ile Thr Asp Gln
            820                 825                 830

Val Gln Gly Lys Gln Val Asn Lys Val Leu Thr Asp Tyr Leu Pro Asp
                835                 840                 845

Phe Glu Ile
            850

<210> SEQ ID NO 35
<211> LENGTH: 30
<212> TYPE: DNA
<213> ORGANISM: Artificial Sequence
<220> FEATURE:
<223> OTHER INFORMATION: Primer

<400> SEQUENCE: 35
catatgcaga aaagcatcct gcgtctgagt                                         30

<210> SEQ ID NO 36
<211> LENGTH: 2109
<212> TYPE: DNA
<213> ORGANISM: Bacteroides thetaiotaomicron

<400> SEQUENCE: 36
atgaagaaca tcttctttat ttgcttttgt gcgctattcg catttagtgg atgcgcagac        60
gatgatgatg atctattaac cggagggaat gtagatatag atctgcttcc tgatgccaaa      120
ccaaacgatg ttgttgatcc tcaagtattc gaggctatca acctcaacta ccccggtctg      180
gaaaaagtta agaattcta cgaggcaggc aacattatt atgcagccaa tgctttattg        240
gaatactata gaacgagaac caatgttaca atccgaact tatctttaat taatgtgacg       300
atctcagaag cagagcaggc aaaagctgat tatgcactgg tagattatcg ctttcatgtt      360
aacaacttct atgaagataa ggaaaccctg aaaccctatt cagtaaaaca agacggaggt      420
ataaactggg agtattcacc gaaagatgca tctgatgaat atcagaaaca acttcatcgc      480
catcagtggt tcatccccca agccaaagct taccgtgtaa gtggagatga aaatacatt       540 caatcatgga ttgaggtata taagaattgg atagaaaaca atccgaagcc tacaacagga      600
cctaatacta cctcatggtg gcagttacag gtatctaccc gtatcggtga ccaagtacaa      660
ttgcttgaat acttcaagaa ctctgttaat tttactccgg aatggctttc tacattcttg      720
gtagaatttg cagaacaagc agactttctc gtagattatc cgtatgaatc aggaggtaac      780
atacttatat cacaagcgaa tgcattggct actgccggaa cgttaatgcc ggaatttaag      840
aatgcggaga atggatgaa tacaggatat cagatactta gcgaagaagt acaaaatcaa       900
attatgagtg acggatggca aaggaaatg tcgctccact atcatatcgg tatcgttgcg       960
gatttctacg aggcaatgaa attagcagag gcaaaccaac tctccagtaa attgccgtca     1020
gattttacag aaccactgcg taaagcagca gaagtagtga tgtacttcac atatcctaat     1080
tactttatca agggttccga taatgtggtc ccaatgttca cgactcatg gagccggaca      1140 cgtaatgtcc ttaaaaatac gaactttaag caatatgtgg aaatgttccc ggatagtgaa     1200
gaattgaaat atatgcaaac tgccggaaat ggtggaacag cacagggacg taccccccaat    1260 aatgatatga agctattcga ccaggcagga tattatgtat tacgaaatgg ttggacaccg     1320
gcttctacag tcatgatttt aagcaataac aagagtaatg atgcttctaa ttcacttagt    1380
gcttatagtc ataaccagcc agataatgga actttcgaac tttaccataa cggacgaaat    1440 tttttcccctg attcaggtgt gtgtacttat tataccagcg gtggagacaa tgacttacgt    1500
tactggttcc gtggtatcga taaacacaat actttatcaa tcggaaaaca gaatatcaaa    1560
```

-continued

```
aaggcagcag gcaaactgtt gaaatcagag gaaggagcga ctgaattagt tgtatttgag      1620
aatcaaggat atgataactt aaagcaccgt cgtgcagtct tttacgtaaa caaaaaattc      1680
tttgtattag tagatgaagg tattggaaat gcagaaggta ctattaatct aagtttcaat      1740
ctttgcgaag gcactgccag cgaagttgtt atggatacag ataaaaatgg agtccataca      1800
gcattcagca ataataataa cattatagtc cgcacttttg ccaataaagc agtaacctgt      1860
tctccattca cggggcgtat agcctatctc gtagacgggg cttacaacac acgtcaatct      1920
tataccatcg atatgaataa gagtgctgat gaaaccgcac gttacattac agttattctt      1980
ccagtcaatg gaagtactga tacgtccagt atctcagcca aattcataga tagcggatat      2040
tccgaaaaca gcgcttctgt agaagtaagt gtgaatggag agacacatac attatcttat      2100
accttataa                                                              2109
```

<210> SEQ ID NO 37
<211> LENGTH: 702
<212> TYPE: PRT
<213> ORGANISM: Bacteroides thetaiotaomicron

<400> SEQUENCE: 37

```
Met Lys Asn Ile Phe Phe Ile Cys Phe Cys Ala Leu Phe Ala Phe Ser
 1               5                  10                  15

Gly Cys Ala Asp Asp Asp Asp Leu Leu Thr Gly Gly Asn Val Asp
             20                  25                  30

Ile Asp Leu Leu Pro Asp Ala Lys Pro Asn Asp Val Val Asp Pro Gln
         35                  40                  45

Val Phe Glu Ala Ile Asn Leu Asn Tyr Pro Gly Leu Glu Lys Val Lys
     50                  55                  60

Glu Phe Tyr Glu Ala Gly Glu His Tyr Tyr Ala Ala Asn Ala Leu Leu
 65                  70                  75                  80

Glu Tyr Tyr Arg Thr Arg Thr Asn Val Thr Asn Pro Asn Leu Ser Leu
                 85                  90                  95

Ile Asn Val Thr Ile Ser Glu Ala Glu Gln Ala Lys Ala Asp Tyr Ala
            100                 105                 110

Leu Val Asp Tyr Arg Phe His Val Asn Asn Phe Tyr Glu Asp Lys Glu
        115                 120                 125

Thr Leu Lys Pro Tyr Ser Val Lys Gln Asp Gly Gly Ile Asn Trp Glu
    130                 135                 140

Tyr Ser Pro Lys Asp Ala Ser Asp Glu Tyr Gln Lys Gln Leu His Arg
145                 150                 155                 160

His Gln Trp Phe Ile Pro Gln Ala Lys Ala Tyr Arg Val Ser Gly Asp
                165                 170                 175

Glu Lys Tyr Ile Gln Ser Trp Ile Glu Val Tyr Lys Asn Trp Ile Glu
            180                 185                 190

Asn Asn Pro Lys Pro Thr Thr Gly Pro Asn Thr Thr Ser Trp Trp Gln
        195                 200                 205

Leu Gln Val Ser Thr Arg Ile Gly Asp Gln Val Gln Leu Leu Glu Tyr
    210                 215                 220

Phe Lys Asn Ser Val Asn Phe Thr Pro Glu Trp Leu Ser Thr Phe Leu
225                 230                 235                 240

Val Glu Phe Ala Glu Gln Ala Asp Phe Leu Val Asp Tyr Pro Tyr Glu
                245                 250                 255

Ser Gly Gly Asn Ile Leu Ile Ser Gln Ala Asn Ala Leu Ala Thr Ala
            260                 265                 270
```

```
Gly Thr Leu Met Pro Glu Phe Lys Asn Ala Glu Lys Trp Met Asn Thr
            275                 280                 285

Gly Tyr Gln Ile Leu Ser Glu Glu Val Gln Asn Gln Ile Met Ser Asp
        290                 295                 300

Gly Trp His Lys Glu Met Ser Leu His Tyr His Ile Gly Ile Val Ala
305                 310                 315                 320

Asp Phe Tyr Glu Ala Met Lys Leu Ala Glu Ala Asn Gln Leu Ser Ser
                325                 330                 335

Lys Leu Pro Ser Asp Phe Thr Glu Pro Leu Arg Lys Ala Ala Glu Val
                340                 345                 350

Val Met Tyr Phe Thr Tyr Pro Asn Tyr Phe Ile Lys Gly Ser Asp Asn
            355                 360                 365

Val Val Pro Met Phe Asn Asp Ser Trp Ser Arg Thr Arg Asn Val Leu
        370                 375                 380

Lys Asn Thr Asn Phe Lys Gln Tyr Val Glu Met Phe Pro Asp Ser Glu
385                 390                 395                 400

Glu Leu Lys Tyr Met Gln Thr Ala Gly Asn Gly Gly Thr Ala Gln Gly
                405                 410                 415

Arg Thr Pro Asn Asn Asp Met Lys Leu Phe Asp Gln Ala Gly Tyr Tyr
            420                 425                 430

Val Leu Arg Asn Gly Trp Thr Pro Ala Ser Thr Val Met Ile Leu Ser
        435                 440                 445

Asn Asn Lys Ser Asn Asp Ala Ser Asn Ser Leu Ser Ala Tyr Ser His
450                 455                 460

Asn Gln Pro Asp Asn Gly Thr Phe Glu Leu Tyr His Asn Gly Arg Asn
465                 470                 475                 480

Phe Phe Pro Asp Ser Gly Val Cys Thr Tyr Tyr Thr Ser Gly Gly Asp
                485                 490                 495

Asn Asp Leu Arg Tyr Trp Phe Arg Gly Ile Asp Lys His Asn Thr Leu
            500                 505                 510

Ser Ile Gly Lys Gln Asn Ile Lys Lys Ala Ala Gly Lys Leu Leu Lys
        515                 520                 525

Ser Glu Glu Gly Ala Thr Glu Leu Val Val Phe Glu Asn Gln Gly Tyr
530                 535                 540

Asp Asn Leu Lys His Arg Arg Ala Val Phe Tyr Val Asn Lys Lys Phe
545                 550                 555                 560

Phe Val Leu Val Asp Glu Gly Ile Gly Asn Ala Glu Gly Thr Ile Asn
                565                 570                 575

Leu Ser Phe Asn Leu Cys Glu Gly Thr Ala Ser Glu Val Val Met Asp
            580                 585                 590

Thr Asp Lys Asn Gly Val His Thr Ala Phe Ser Asn Asn Asn Asn Ile
        595                 600                 605

Ile Val Arg Thr Phe Ala Asn Lys Ala Val Thr Cys Ser Pro Phe Thr
610                 615                 620

Gly Arg Ile Ala Tyr Leu Val Asp Gly Ala Tyr Asn Thr Arg Gln Ser
625                 630                 635                 640

Tyr Thr Ile Asp Met Asn Lys Ser Ala Asp Glu Thr Ala Arg Tyr Ile
                645                 650                 655

Thr Val Ile Leu Pro Val Asn Gly Ser Thr Asp Thr Ser Ser Ile Ser
            660                 665                 670

Ala Lys Phe Ile Asp Ser Gly Tyr Ser Glu Asn Ser Ala Ser Val Glu
        675                 680                 685

Val Ser Val Asn Gly Glu Thr His Thr Leu Ser Tyr Thr Leu
690                 695                 700
```

<210> SEQ ID NO 38
<211> LENGTH: 2052
<212> TYPE: DNA
<213> ORGANISM: Bacteroides thetaiotaomicron

<400> SEQUENCE: 38

```
gacgatgatg atgatctatt aaccggaggg aatgtagata tagatctgct tcctgatgcc      60
aaaccaaacg atgttgttga tcctcaagta ttcgaggcta tcaacctcaa ctaccccggt     120
ctggaaaaag ttaaagaatt ctacgaggca ggcgaacatt attatgcagc caatgctttta    180 ttggaatact atagaacgag aaccaatgtt acaaatccga acttatcttt aattaatgtg     240
acgatctcag aagcagagca ggcaaaagct gattatgcac tggtagatta tcgctttcat     300
gttaacaact tctatgaaga taaggaaacc ctgaaaccct attcagtaaa acaagacgga     360
ggtataaact gggagtattc accgaaagat gcatctgatg aatatcagaa acaacttcat     420
cgccatcagt ggttcatccc ccaagccaaa gcttaccgtg taagtggaga tgagaaatac     480
attcaatcat ggattgaggt atataagaat tggatagaaa acaatccgaa gcctacaaca     540
ggacctaata ctacctcatg gtggcagtta caggtatcta cccgtatcgg tgaccaagta     600
caattgcttg aatacttcaa gaactctgtt aattttactc cggaatggct ttctacattc     660
ttggtagaat ttgcagaaca agcagacttt ctcgtagatt atccgtatga atcaggaggt     720
aacatactta tatcacaagc gaatgcattg gctactgccg gaacgttaat gccggaattt     780
aagaatgcgg agaaatggat gaatacagga tatcagatac ttagcgaaga agtacaaaat     840
caaattatga gtgacggatg gcacaaggaa atgtcgctcc actatcatat cggtatcgtt     900
gcggatttct acgaggcaat gaaattagca gaggcaaacc aactctccag taaattgccg     960
tcagatttta cagaaccact gcgtaaagca gcagaagtag tgatgtactt cacatatcct    1020
aattacttta tcaagggttc cgataatgtg gtcccaatgt tcaacgactc atggagccgg    1080
acacgtaatg tccttaaaaa tacgaacttt aagcaatatg tggaaatgtt cccggatagt    1140
gaagaattga aatatatgca aactgccgga aatggtggaa cagcacaggg acgtacccec    1200 aataatgata tgaagctatt cgaccaggca ggatatattg tattacgaaa tggttggaca    1260
ccggcttcta cagtcatgat tttaagcaat aacaagagta atgatgcttc taattcactt    1320
agtgcttata gtcataacca gccagataat ggaactttcg aactttacca taacggacga    1380 aatttttttcc ctgattcagg tgtgtgtact tattatacca gcggtggaga caatgactta    1440
cgttactggt tccgtggtat cgataaacac aatactttat caatcggaaa acagaatatc    1500
aaaaaggcag caggcaaact gttgaaatca gaggaaggag cgactgaatt agttgtatttt   1560 gagaatcaag gatatgataa cttaaagcac cgtcgtgcag tcttttacgt aaacaaaaaa    1620
ttctttgtat tagtagatga aggtattgga aatgcagaag gtactattaa tctaagttttc  1680 aatctttgcg aaggcactgc cagcgaagtt gttatggata cagataaaaa tggagtccat    1740
acagcattca gcaataataa taacattata gtccgcactt ttgccaataa agcagtaacc    1800
tgttctccat tcacggggcg tatagcctat ctcgtagacg gggcttacaa cacacgtcaa    1860
tcttatacca tcgatatgaa taagagtgct gatgaaaccg cacgttacat tacagttatt    1920
cttccagtca atggaagtac tgatacgtcc agtatctcag ccaaattcat agatagcgga    1980
tattccgaaa acagcgcttc tgtagaagta agtgtgaatg gagagacaca tacattatct    2040
tataccttat aa                                                        2052
```

```
<210> SEQ ID NO 39
<211> LENGTH: 683
<212> TYPE: PRT
<213> ORGANISM: Bacteroides thetaiotaomicron

<400> SEQUENCE: 39

Asp Asp Asp Asp Asp Leu Leu Thr Gly Gly Asn Val Asp Ile Asp Leu
 1               5                  10                  15

Leu Pro Asp Ala Lys Pro Asn Asp Val Val Asp Pro Gln Val Phe Glu
             20                  25                  30

Ala Ile Asn Leu Asn Tyr Pro Gly Leu Glu Lys Val Lys Glu Phe Tyr
         35                  40                  45

Glu Ala Gly Glu His Tyr Tyr Ala Ala Asn Ala Leu Leu Glu Tyr Tyr
     50                  55                  60

Arg Thr Arg Thr Asn Val Thr Asn Pro Asn Leu Ser Leu Ile Asn Val
 65                  70                  75                  80

Thr Ile Ser Glu Ala Glu Gln Ala Lys Ala Asp Tyr Ala Leu Val Asp
                 85                  90                  95

Tyr Arg Phe His Val Asn Asn Phe Tyr Glu Asp Lys Glu Thr Leu Lys
            100                 105                 110

Pro Tyr Ser Val Lys Gln Asp Gly Gly Ile Asn Trp Glu Tyr Ser Pro
        115                 120                 125

Lys Asp Ala Ser Asp Glu Tyr Gln Lys Gln Leu His Arg His Gln Trp
130                 135                 140

Phe Ile Pro Gln Ala Lys Ala Tyr Arg Val Ser Gly Asp Glu Lys Tyr
145                 150                 155                 160

Ile Gln Ser Trp Ile Glu Val Tyr Lys Asn Trp Ile Glu Asn Asn Pro
                165                 170                 175

Lys Pro Thr Thr Gly Pro Asn Thr Thr Ser Trp Gln Leu Gln Val
            180                 185                 190

Ser Thr Arg Ile Gly Asp Gln Val Gln Leu Leu Glu Tyr Phe Lys Asn
        195                 200                 205

Ser Val Asn Phe Thr Pro Glu Trp Leu Ser Thr Phe Leu Val Glu Phe
    210                 215                 220

Ala Glu Gln Ala Asp Phe Leu Val Asp Tyr Pro Tyr Glu Ser Gly Gly
225                 230                 235                 240

Asn Ile Leu Ile Ser Gln Ala Asn Ala Leu Ala Thr Ala Gly Thr Leu
                245                 250                 255

Met Pro Glu Phe Lys Asn Ala Glu Lys Trp Met Asn Thr Gly Tyr Gln
            260                 265                 270

Ile Leu Ser Glu Glu Val Gln Asn Gln Ile Met Ser Asp Gly Trp His
        275                 280                 285

Lys Glu Met Ser Leu His Tyr His Ile Gly Ile Val Ala Asp Phe Tyr
    290                 295                 300

Glu Ala Met Lys Leu Ala Glu Ala Asn Gln Leu Ser Ser Lys Leu Pro
305                 310                 315                 320

Ser Asp Phe Thr Glu Pro Leu Arg Lys Ala Glu Val Val Met Tyr
                325                 330                 335

Phe Thr Tyr Pro Asn Tyr Phe Ile Lys Gly Ser Asp Asn Val Val Pro
            340                 345                 350

Met Phe Asn Asp Ser Trp Ser Arg Thr Arg Asn Val Leu Lys Asn Thr
        355                 360                 365

Asn Phe Lys Gln Tyr Val Glu Met Phe Pro Asp Ser Glu Glu Leu Lys
    370                 375                 380

Tyr Met Gln Thr Ala Gly Asn Gly Gly Thr Ala Gln Gly Arg Thr Pro
```

```
                385                 390                 395                 400
Asn Asn Asp Met Lys Leu Phe Asp Gln Ala Gly Tyr Tyr Val Leu Arg
                    405                 410                 415
Asn Gly Trp Thr Pro Ala Ser Thr Val Met Ile Leu Ser Asn Asn Lys
                420                 425                 430
Ser Asn Asp Ala Ser Asn Ser Leu Ser Ala Tyr Ser His Asn Gln Pro
            435                 440                 445
Asp Asn Gly Thr Phe Glu Leu Tyr His Asn Gly Arg Asn Phe Phe Pro
        450                 455                 460
Asp Ser Gly Val Cys Thr Tyr Tyr Thr Ser Gly Gly Asp Asn Asp Leu
465                 470                 475                 480
Arg Tyr Trp Phe Arg Gly Ile Asp Lys His Asn Thr Leu Ser Ile Gly
                485                 490                 495
Lys Gln Asn Ile Lys Lys Ala Ala Gly Lys Leu Leu Lys Ser Glu Glu
                500                 505                 510
Gly Ala Thr Glu Leu Val Val Phe Glu Asn Gln Gly Tyr Asp Asn Leu
            515                 520                 525
Lys His Arg Arg Ala Val Phe Tyr Val Asn Lys Lys Phe Phe Val Leu
        530                 535                 540
Val Asp Glu Gly Ile Gly Asn Ala Glu Gly Thr Ile Asn Leu Ser Phe
545                 550                 555                 560
Asn Leu Cys Glu Gly Thr Ala Ser Glu Val Val Met Asp Thr Asp Lys
                565                 570                 575
Asn Gly Val His Thr Ala Phe Ser Asn Asn Asn Ile Ile Val Arg
                580                 585                 590
Thr Phe Ala Asn Lys Ala Val Thr Cys Ser Pro Phe Thr Gly Arg Ile
            595                 600                 605
Ala Tyr Leu Val Asp Gly Ala Tyr Asn Thr Arg Gln Ser Tyr Thr Ile
        610                 615                 620
Asp Met Asn Lys Ser Ala Asp Glu Thr Ala Arg Tyr Ile Thr Val Ile
625                 630                 635                 640
Leu Pro Val Asn Gly Ser Thr Asp Thr Ser Ser Ile Ser Ala Lys Phe
                645                 650                 655
Ile Asp Ser Gly Tyr Ser Glu Asn Ser Ala Ser Val Glu Val Ser Val
                660                 665                 670
Asn Gly Glu Thr His Thr Leu Ser Tyr Thr Leu
            675                 680
```

<210> SEQ ID NO 40
<211> LENGTH: 33
<212> TYPE: DNA
<213> ORGANISM: Artificial Sequence
<220> FEATURE:
<223> OTHER INFORMATION: Primer

<400> SEQUENCE: 40
ctcgagttat aaggtataag ataatgtatg tgt                              33

<210> SEQ ID NO 41
<211> LENGTH: 30
<212> TYPE: DNA
<213> ORGANISM: Artificial Sequence
<220> FEATURE:
<223> OTHER INFORMATION: Primer

<400> SEQUENCE: 41
catatgcaaa cactgatgcc actcaccgaa                                 30

What is claimed is:

1. A method of specifically cleaving a heparin or a heparan sulfate, comprising:
   selecting an isolated *B. thetaiotaomicron* HSGAG lyase polypeptide I, or a functional fragment thereof, that cleaves a glycosidic linkage between a glucosamine having a sulfate at position 3 and a sulfated uronic acid of the heparin or heparan sulfate, wherein the *B. thetaiotaomicron* HSGAG lyase I polypeptide comprises
   a) an amino acid sequence which is at least 90% identical to the amino acid sequence of SEQ ID NO:2;
   b) the amino acid sequence of SEQ ID NO:2, 4 or 23; and
   c) an amino acid sequence which differs by at least 1 amino acid but not more than 15 amino acids from the amino acid sequence of SEQ ID NO:2, and
   contacting the heparin or the heparan sulfate with the *B. thetaiotaomicron* HSGAG lyase polypeptide I, to thereby cleave the heparin or heparan sulfate.

2. The method of claim 1, further comprising contacting the heparin or heparan sulfate with an isolated *B. thetaiotaomicron* HSGAG lyase II polypeptide, or functional fragment thereof.

3. The method of claim 1, wherein the *B. thetaiotaomicron* HSGAG lyase I polypeptide is encoded by a nucleotide sequence selected from the group consisting of:
   a) a nucleic acid molecule comprising a fragment of at least 800 nucleotides of the nucleotide sequence of SEQ ID NO:1, 3 or 22;
   b) a nucleic acid molecule which encodes a polypeptide comprising the amino acid sequence of SEQ ID NO:2, 4 or 23; and
   c) a nucleic acid molecule which encodes a fragment of a polypeptide comprising the amino acid sequence of SEQ ID NO:2, 4 or 23, wherein the fragment comprises at least 300 contiguous amino acids of SEQ ID NO:2, 4 or 23.

4. The method of claim 1 or 3, wherein the *B. thetaiotaomicron* HSGAG lyase I cleaves a heparin at one or more glycosidic linkages of 2-O sulfated uronic acids.

5. The method of claim 1, wherein the heparin or heparan sulfate is cleaved into di-, tri-, tetra-, penta-, hexa-, octa-, deca- saccharides, and combinations thereof.

6. The method of claim 1, further comprising contacting the heparin or heparan sulfate with one or more HLGAG degrading enzyme other than the *B. thetaiotaomicron* HSGAG lyase I polypeptide.

7. The method of claim 6, wherein the HLGAG degrading enzyme is selected from *Flavobacterium heparinum* heparinase I, *Flavobacterium heparinum* heparinase II, *Flavobacterium heparinum* heparinase III, *Flavobacterium heparinum* heparinase IV, heparanase, sulfatase, delta 4,5 glucuronidase and functional fragments thereof.

8. The method of claim 1, further comprising determining if a structural signature is absent or present in the cleaved heparin or heparin sulfate.

9. The method of claim 8, further comprising comparing the absence or presence of the structural signature or the amount of the structural signature of the heparin or heparin sulfate to a preselected value.

10. The method of claim 9, wherein the preselected value is the absence, presence or amount of the structural signature present in a commercially available heparin or heparin sulfate.

11. The method of claim 10, wherein the commercially available heparin is selected from: unfractionated heparin, enoxaparin, dalteparin, certoparin, ardeparin, nadroparin, parnaparin, reviparin, tinzaparin, and Fondaparinux.

12. The method of claim 9, further comprising selecting or discarding the heparin or heparin sulfate as a result of the determination.

13. The method of claim 8, wherein the structural signature is determined by one or more of mass spectroscopy, NMR spectroscopy, gel electrophoresis, capillary electrophoresis, reverse-phase column chromatography, and ion-pair HPLC.

14. The method of claim 10, wherein the structural signature is one or more of the following structures:

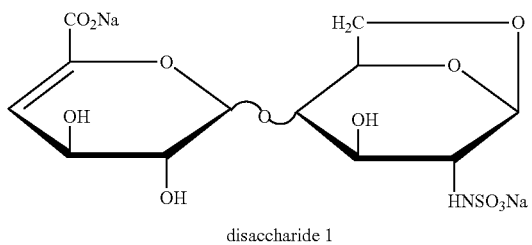

disaccharide 1

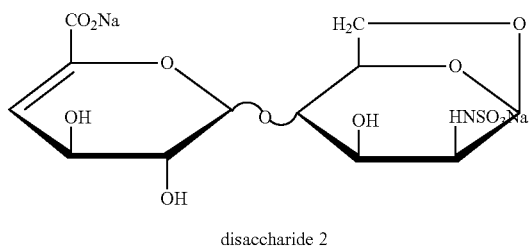

disaccharide 2

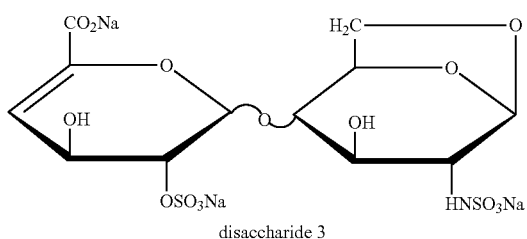

disaccharide 3

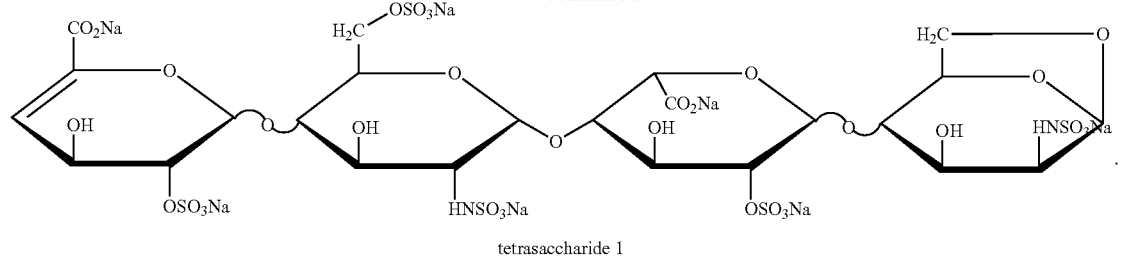
tetrasaccharide 1
* * * * *